(12) United States Patent
Weiner et al.

(10) Patent No.: US 10,548,971 B2
(45) Date of Patent: Feb. 4, 2020

(54) MERS-COV VACCINE

(71) Applicants: The Trustees of the University of Pennsylvania, Philadelphia, PA (US); Inovio Pharmaceuticals, Inc., Plymouth Meeting, PA (US)

(72) Inventors: David Weiner, Merion, PA (US); Karuppiah Muthumani, Cherry Hill, NJ (US); Niranjan Y. Sardesai, Blue Bell, PA (US)

(73) Assignees: THE TRUSTEES OF THE UNIVERSITY OF PENNSYLVANIA, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 0 days.

(21) Appl. No.: 16/022,839

(22) Filed: Jun. 29, 2018

(65) Prior Publication Data

US 2019/0022213 A1    Jan. 24, 2019

Related U.S. Application Data

(63) Continuation of application No. 15/039,672, filed as application No. PCT/US2014/067537 on Nov. 26, 2014, now Pat. No. 10,016,497.

(60) Provisional application No. 61/910,153, filed on Nov. 29, 2013.

(51) Int. Cl.
| | | |
|---|---|---|
| *A61K 39/215* | (2006.01) | |
| *A61K 39/12* | (2006.01) | |
| *C12N 7/00* | (2006.01) | |
| *A61K 39/00* | (2006.01) | |

(52) U.S. Cl.
CPC ............ *A61K 39/215* (2013.01); *A61K 39/12* (2013.01); *C12N 7/00* (2013.01); *A61K 2039/53* (2013.01); *C12N 2770/20034* (2013.01)

(58) Field of Classification Search
None
See application file for complete search history.

(56) References Cited

U.S. PATENT DOCUMENTS

| | | |
|---|---|---|
| 2009/0069256 A1 | 3/2009 | Smith |
| 2016/0206729 A1 | 7/2016 | Smith |

FOREIGN PATENT DOCUMENTS

| | | |
|---|---|---|
| WO | 2010017542 A1 | 2/2010 |
| WO | 2013083847 A2 | 6/2013 |

OTHER PUBLICATIONS

Van Boheemen S, et al. 2012. Genomic characterization of a newly discovered coronavirus associated with acute respiratory distress syndrome in humans. mBio 3(6): e00473-12. doi:10.1128/mBio.00473-12.*
Lokugamage et al. Chimeric coronavirus-like particles carrying severe acute respiratory syndrome coronavirus (SCoV) S protein protect mice against challenge with SCoV. Vaccine (2008) 26, 797-808.*
Zhou et al. Immunogenicity difference between the SARS coronavirus and the bat SARS-like coronavirus spike (S) proteins. Biochemical and Biophysical Research Communications 387 (2009) 326-329.*
Gen Bank: JX869059.2. Human betacoronavirus 2c EMC/2012, complete genome. Date Dec. 4, 2012.*
"Human betacoronavirus 2c Jordan-N3/2012, complete genome", Database GenBank, (Mar. 25, 2013), Database accession No. KC776174, XP002764824, 12 pages.
Corrected Notice of Allowability dated Mar. 15, 2018 for U.S. Appl. No. 15/039,672 (pp. 1-2).
Corrected Notice of Allowability dated Mar. 26, 2018 for U.S. Appl. No. 15/039,672 (pp. 1-3).
Cotten et al., "Full-genome deep sequencing and phylogenetic analysis of novel human betacoronavirus," Human betacoronavirus 2c England-Qatar/2012, complete genome, Accession No. KC667074.1, XP-002764825, 11 pages.
Cotten et al., "Spread, Circulation, and Evolution of the Middle East Respiratory Syndrome Coronavirus," mBio, 2014, 5(1):e01062-13.
Cotten et al., "Transmission and evolution of the Middle East respiratory syndrome coronavirus in Saudi Arabia: a descriptive genomic study", Lancet, 2013, 382:1993-2002.
Cotten M, "Middle East respiratory syndrome coronavirus isolate Al-HASA_4_2013, complete genome.", Database Genbank, (Jun. 10, 2013), Database accession No. KF186564.1, XP055295837, 17 pages.
Falzarano et al., "Interferon-a2b and ribavirin treatment improves outcome in MERS-CoV-infected rhesus macaques", Mat Med, vol. 19(10): pp. 1313-1317 (2013).
Gen Bank: AFS88936. S protein, Human betacoronavirus 2c EMC/2012. Date Dec. 4, 2012, 2 pages.
Notice of Allowance dated Mar. 5, 2018 for U.S. Appl. No. 15/039,672 (pp. 1-8).
Song F, et al., 'Middle East Respiratory Syndrome Coronavirus Spike Protein Delivered by Modified Vaccinia Virus Ankara Efficiently Induces Virus-Neutralizing Antibodies,' Journal of Virology, (2013) vol. 87, No. 21, pp. 11950-11954.

* cited by examiner

*Primary Examiner* — Nianxiang Zou
(74) *Attorney, Agent, or Firm* — Riverside Law LLP

(57) ABSTRACT

Disclosed herein is a vaccine comprising a Middle East Respiratory Syndrome coronavirus (MERS-CoV) antigen. The antigen can be a consensus antigen. The consensus antigen can be a consensus spike antigen. Also disclosed herein is a method of treating a subject in need thereof, by administering the vaccine to the subject.

13 Claims, 39 Drawing Sheets
Specification includes a Sequence Listing.

MERS-CoV Consensus Spike Antigen – Nucleotide Sequence
ATGGACTGGACTTGGATTCTGTTCCTGGTCGCCGCCGCAACTCGCGTGCATAGCTAC
GTGGATGTCGGCCCAGACTCTGTGAAGAGTGCTTGCATCGAGGTCGATATTCAGCAG
ACATTCTTTGACAAGACTTGGCCTCGACCAATCGACGTGAGCAAAGCCGACGGCAT
CATCTACCCCCAGGGAAGGACTTATAGTAACATCACCATTACATACCAGGGCCTGTT
CCCTTATCAGGGCGACCACGGAGATATGTACGTGTATTCCGCCGGACATGCTACCGG
GACCACACCACAGAAACTGTTTGTGGCAAATTATTCTCAGGACGTGAAGCAGTTCGC
CAACGGGTTTGTGGTCAGAATCGGCGCCGCTGCAAACTCCACTGGCACCGTGATCAT
TTCCCCCTCTACCAGTGCCACAATCCGGAAAATCTACCCTGCTTTTATGCTGGGCAG
CTCCGTGGGAAACTTCTCTGATGGGAAGATGGGCCGCTTCTTTAATCACACCCTGGT
GCTGCTGCCAGACGGATGCGGGACACTGCTGAGGGCCTTCTACTGTATCCTGGAGCC
CAGAAGCGGAAATCACTGCCCTGCTGGGAACTCATACACCAGCTTTGCCACTTATCA
TACCCCTGCTACAGACTGTTCCGATGGCAATTATAACCGGAATGCCTCCCTGAACTC
TTTCAAGGAATACTTTAATCTGCGCAACTGCACATTCATGTACACTTATAATATCACC
GAGGATGAAATTCTGGAGTGGTTCGGGATCACACAGACTGCTCAGGGCGTGCACCT
GTTTTCTAGTCGCTACGTCGATCTGTATGGCGGAAACATGTTCCAGTTTGCCACCCTG
CCAGTGTACGACACAATTAAGTACTATAGCATCATTCCCCATAGTATCCGATCAATT
CAGAGCGACAGGAAGGCTTGGGCCGCTTTCTACGTGTATAAACTGCAGCCCCTGAC
CTTCCTGCTGGATTTTTCTGTGGACGGATACATCAGGAGAGCCATTGATTGCGGGTT
TAACGACCTGAGCCAGCTGCACTGTTCCTATGAATCTTTCGATGTGGAGTCCGGGGT
GTACTCTGTCTCAAGCTTTGAGGCTAAGCCATCAGGGAGCGTGGTCGAGCAGGCAG
AAGGCGTGGAGTGCGACTTCAGTCCCCTGCTGTCAGGCACACCCCTCAGGTGTACA
ATTTCAAAAGACTGGTCTTTACTAACTGTAATTACAACCTGACCAAGCTGCTGAGTC
TGTTCTCAGTGAACGACTTTACCTGCAGCCAGATCTCCCCTGCAGCCATTGCCAGCA
ATTGTTATTCCTCTCTGATCCTGGATTACTTCTCCTATCCCCTGTCTATGAAAAGTGA
CCTGTCAGTGAGTTCAGCAGGCCCTATCTCTCAGTTTAATTACAAGCAGTCCTTCTCT
AACCCCACTTGCCTGATTCTGGCCACCGTGCCTCACAACCTGACTACCATCACAAAG
CCACTGAAATACTCCTATATTAACAAGTGCAGCAGACTGCTGTCCGACGATCGGACT
GAAGTGCCTCAGCTGGTCAATGCCAACCAGTACTCTCCATGCGTGAGCATCGTCCCC
TCAACCGTGTGGGAAGACGGAGATTACTATCGGAAGCAGCTGAGCCCCCTGGAGGG
CGGCGGCTGGCTGGTGGCAAGTGGGTCAACAGTCGCCATGACTGAGCAGCTGCAGA
TGGGCTTCGGAATCACCGTGCAGTACGGCACCGATACAAATTCTGTCTGTCCTAAGC
TGGAATTTGCTAACGACACAAAAATTGCAAGTCAGCTGGGCAATTGCGTGGAGTAC
TCTCTGTATGGAGTGAGTGGGAGAGGCGTCTTCCAGAACTGTACAGCCGTGGGCGTC
CGACAGCAGAGGTTCGTGTACGATGCTTATCAGAACCTGGTCGGCTACTATTCCGAC
GATGGAAATTACTATTGCCTGCGAGCATGCGTGAGCGTCCCAGTGTCCGTCATCTAC
GACAAGGAAACTAAAACCCACGCAACCCTGTTCGGCTCAGTGGCCTGCGAGCATAT
TAGCTCCACCATGAGCCAGTATAGCAGATCCACACGGTCCATGCTGAAACGGCGCG
ACTCTACATACGGACCCCTGCAGACTCCTGTGGGGTGCGTGCTGGGCCTGGTGAACT
CTAGTCTGTTCGTCGAAGATTGCAAGCTGCCACTGGGACAGTCTCTGTGCGCACTGC
CAGACACACCCAGTACACTGACTCCACGCAGCGTGCGATCCGTCCCAGGAGAGATG
AGACTGGCAAGCATCGCCTTCAATCACCCTATTCAGGTGGATCAGCTGAACTCAAGC
TACTTTAAGCTGTCAATCCCAACAAACTTCAGCTTTGGCGTGACTCAGGAGTATATC
CAGACAACTATTCAGAAGGTGACCGTCGACTGCAAACAGTACGTGTGCAATGGATT
CCAGAAATGCGAACAGCTGCTGCGGGAGTATGGGCAGTTTTGTTCCAAGATCAATC
AGGCACTGCATGGCGCCAACCTGCGCCAGGACGATAGTGTGCGAAACCTGTTCGCC

FIG. 8A

TCAGTCAAGTCCTCTCAGAGTTCACCTATCATTCCAGGGTTCGGCGGCGACTTCAAC
CTGACCCTGCTGGAACCCGTGAGCATCAGTACCGGCAGCAGGAGCGCCAGAAGCGC
AATCGAGGATCTGCTGTTTGACAAAGTGACCATTGCCGACCCAGGATACATGCAGG
GGTATGACGATTGCATGCAGCAGGGACCAGCATCCGCTCGCGATCTGATCTGTGCTC
AGTACGTGGCAGGGTATAAGGTCCTGCCACCCCTGATGGACGTGAACATGGAAGCT
GCATATACTAGCTCCCTGCTGGGGAGCATTGCAGGAGTGGGATGGACCGCTGGACT
GTCTAGTTTCGCCGCTATCCCATTTGCTCAGAGCATTTTCTACAGGCTGAACGGCGTG
GGAATCACTCAGCAGGTCCTGTCCGAGAATCAGAAGCTGATTGCCAACAAGTTCAA
CCAGGCCCTGGGAGCTATGCAGACCGGGTTTACCACAACTAACGAAGCTTTCCGCA
AAGTGCAGGACGCAGTCAACAATAACGCACAGGCCCTGTCCAAGCTGGCTTCTGAG
CTGAGTAATACATTCGGAGCAATCTCCGCCTCTATTGGGGATATCATTCAGAGGCTG
GACGTGCTGGAGCAGGATGCCCAGATCGACCGGCTGATTAATGGACGCCTGACCAC
ACTGAACGCTTTTGTGGCACAGCAGCTGGTCCGAAGTGAATCAGCAGCCCTGTCTGC
CCAGCTGGCTAAGGACAAAGTGAACGAGTGCGTCAAGGCTCAGTCAAAACGGAGCG
GCTTTTGTGGGCAGGGCACCCACATCGTGAGCTTCGTGGTCAATGCACCTAACGGCC
TGTACTTTATGCACGTGGGATACTATCCAAGCAACCATATCGAGGTGGTCTCCGCTT
ATGGCCTGTGCGATGCTGCAAATCCTACAAACTGTATTGCACCAGTGAACGGATACT
TCATCAAAACTAACAACACCAGGATTGTGGACGAATGGTCATACACTGGCTCAAGC
TTTTATGCACCCGAGCCTATCACCTCCCTGAACACAAAGTACGTGGCCCCACATGTC
ACCTATCAGAATATCTCCACAAACCTGCCTCCACCCCTGCTGGGCAATTCTACCGGA
ATTGACTTCCAGGATGAACTGGACGAGTTCTTTAAGAATGTGAGCACATCCATCCCC
AACTTTGGAAGCCTGACTCAGATTAACACTACCCTGCTGGATCTGACCTACGAGATG
CTGAGTCTGCAGCAGGTGGTCAAGGCCCTGAATGAATCATACATCGACCTGAAAGA
GCTGGGGAATTATACATACTATAACAAGTGGCCCTGGTACATCTGGCTGGGGTTCAT
TGCAGGACTGGTGGCTCTGGCACTGTGCGTCTTCTTTATCCTGTGCTGTACTGGATGC
GGGACCAACTGTATGGGCAAGCTGAAATGTAATCGGTGTTGTGATCGCTACGAAGA
ATACGACCTGGAGCCCCATAAAGTGCATGTCCACTAATGA (SEQ ID NO:1)

FIG. 8A (con't)

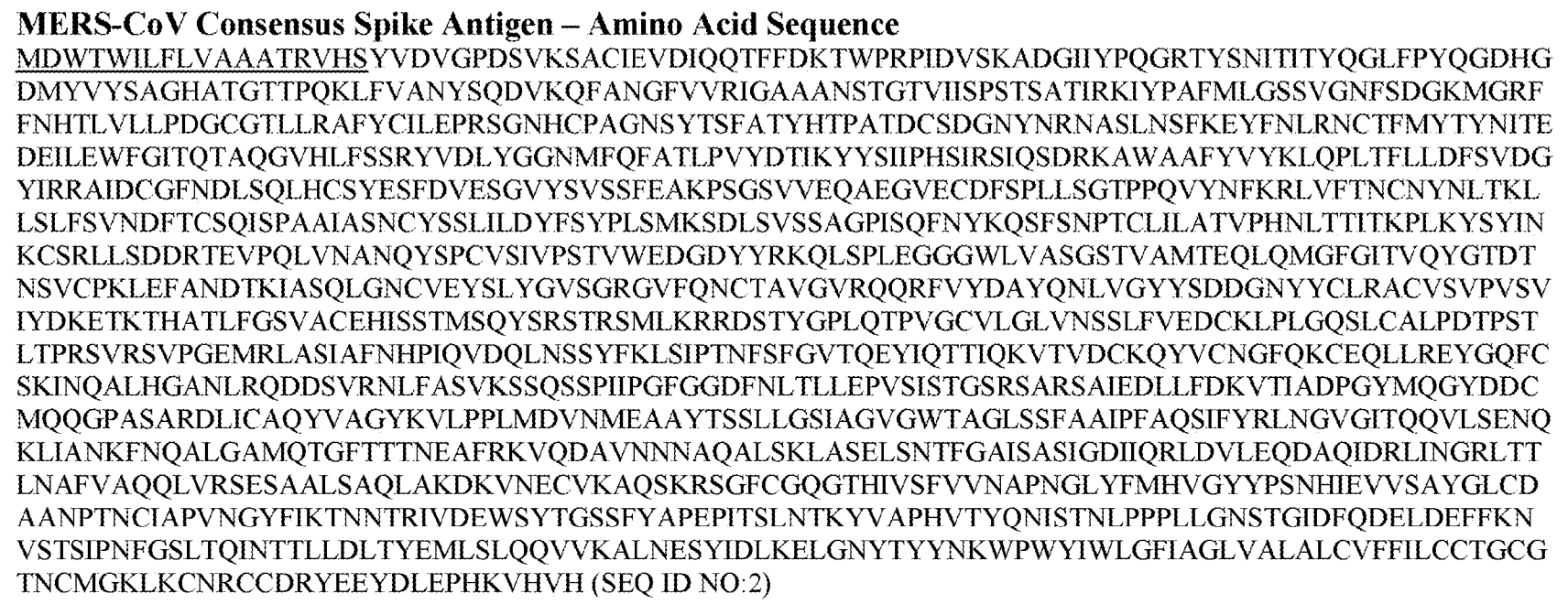

MERS-CoV Consensus Spike Antigen – Amino Acid Sequence

MDWTWILFLVAAATRVHSYVDVGPDSVKSACIEVDIQQTFFDKTWPRPIDVSKADGIIYPQGRTYSNITITYQGLFPYQGDHG
DMYVYSAGHATGTTPQKLFVANYSQDVKQFANGFVVRIGAAANSTGTVIISPSTSATIRKIYPAFMLGSSVGNFSDGKMGRF
FNHTLVLLPDGCGTLLRAFYCILEPRSGNHCPAGNSYTSFATYHTPATDCSDGNYNRNASLNSFKEYFNLRNCTFMYTYNITE
DEILEWFGITQTAQGVHLFSSRYVDLYGGNMFQFATLPVYDTIKYYSIIPHSIRSIQSDRKAWAAFYVYKLQPLTFLLDFSVDG
YIRRAIDCGFNDLSQLHCSYESFDVESGVYSVSSFEAKPSGSVVEQAEGVECDFSPLLSGTPPQVYNFKRLVFTNCNYNLTKL
LSLFSVNDFTCSQISPAAIASNCYSSLILDYFSYPLSMKSDLSVSSAGPISQFNYKQSFSNPTCLILATVPHNLTTITKPLKYSYIN
KCSRLLSDDRTEVPQLVNANQYSPCVSIVPSTVWEDGDYYRKQLSPLEGGGWLVASGSTVAMTEQLQMGFGITVQYGTDT
NSVCPKLEFANDTKIASQLGNCVEYSLYGVSGRGVFQNCTAVGVRQQRFVYDAYQNLVGYYSDDGNYYCLRACVSVPVSV
IYDKETKTHATLFGSVACEHISSTMSQYSRSTRSMLKRRDSTYGPLQTPVGCVLGLVNSSLFVEDCKLPLGQSLCALPDTPST
LTPRSVRSVPGEMRLASIAFNHPIQVDQLNSSYFKLSIPTNFSFGVTQEYIQTTIQKVTVDCKQYVCNGFQKCEQLLREYGQFC
SKINQALHGANLRQDDSVRNLFASVKSSQSSPIIPGFGGDFNLTLLEPVSISTGSRSARSAIEDLLFDKVTIADPGYMQGYDDC
MQQGPASARDLICAQYVAGYKVLPPLMDVNMEAAYTSSLLGSIAGVGWTAGLSSFAAIPFAQSIFYRLNGVGITQQVLSENQ
KLIANKFNQALGAMQTGFTTTNEAFRKVQDAVNNNAQALSKLASELSNTFGAISASIGDIIQRLDVLEQDAQIDRLINGRLTT
LNAFVAQQLVRSESAALSAQLAKDKVNECVKAQSKRSGFCGQGTHIVSFVVNAPNGLYFMHVGYYPSNHIEVVSAYGLCD
AANPTNCIAPVNGYFIKTNNTRIVDEWSYTGSSFYAPEPITSLNTKYVAPHVTYQNISTNLPPPLLGNSTGIDFQDELDEFFKN
VSTSIPNFGSLTQINTTLLDLTYEMLSLQQVVKALNESYIDLKELGNYTYYNKWPWYIWLGFIAGLVALALCVFFILCCTGCG
TNCMGKLKCNRCCDRYEEYDLEPHKVHVH (SEQ ID NO:2)

FIG. 8B

MERS-CoV Consensus Spike Antigen ΔCD – Nucleotide Sequence

ATGGACTGGACTTGGATTCTGTTCCTGGTCGCCGCCGCAACTCGCGTGCAATAGCTGCGTGGATGTCGGCGGCCAGACTCTG
TGAAGAGAGTGCTTGCATCGAGGTCGATATTCAGCAGGTCGATAAGACTTGGCTTCGACCCAATCGACGTGAGCAA
AGCCGACGGCATCATCTACCCCCAGGAAGGACTTATAGTAACATCACCATTACACCAGGGCCTGTTCCTTATCAG
GGCGACCACCGGAGATATGTACGTGTATTCCCGGACATGCTACCCGGACATGGGCGCCGTGCAAACTCCACTGGCACCGTGA
TATTCTCAGGACGTGAAGCAGTTCGCCACAGTGCCACCAGTGCCAAATCCGGATGCCAAATCGCAAATCGCACTCTGT
TCATTCCCCCCTCTACCAGTGCCACAGTCCGGAATCGGGCCGTCCGTGAATCCACTGGCACCAGTGCCAAATCTTCT
GATGGAAGATGGGCCGCTTCTTTATCACACCCTGGTGCTGCCAGAGATGCGGGACAACTGCGAGGGCCTCTCT
ACTGTATCCTGAGCTACCAGAAGCGGAAATCACTGCCCTCGGAACTCATCACCAGCTTTGCCACTATCATACCCC
TGCTACAGACTGTTCCGATGGCAATTATAACCGGAGAATGCCCCTGAACTCTTTCAAGGAATACTTTAATCTGGCAAC
TGCACATTCATGTACACTACTATATATCCACCGAGGATGTGGCGGAAACATGTTCCAGTTGCCACCTGCCAGTACGACACA
TGCACCTGTTTTCTAGTCGCTACGTCGATTCCCATAGTCATCATTCCCCATAGTACTCGCAGACGCTTGGGCCCGCTTTCCTACGTGT
ATTAAGTACTATAGCATCATTCCCATAGTATCGATCAATTCAGAGCGACAGGAAGGCTTGGCCCGCTTTCCTACGTGT
ATAAACTGCAGCCCCTGAGCCACTGTCCACTGTGTTGATGAATCTTTCGATGTGGAGTCGCGGGTACTCTGTCTCACGTTTGAGCTA
CGACCTGAGCCAGCCATCTGCACTGTCCCTGTGTTGATGAATCTTTCGATGTGGAGTCGGGGTACTCTGTCTCACGTTTGAGCTA
AGCCATCAGGAGCGTGGTCAACTGTCTTTACTAACGGACTCAGTCCCTGCTGTCAGGCACACCCCTC
AGTGTACAATTTCAAAGACTGTCTTTACTAACTGTAATTACAACCTGACCAGCAATTGTATTCTCTCCTGATTACTTCTCCT
CGACTTTACCTGCACTGCAGCCAGATCCCCTGCAGCCATGTCAGTGAGCCCTATCTCTCAGTTGATTACTCTCCT
ATCCCCTGTCTATGAAAAGTGACTTGGCCGTGTCTGTGCTCCAACAACCTGACTACTGAGTGCCTCAATCCACTGAAATACTCCTATATTA
AACCCCACTGCTGATTCGGACCAGACTGCTGTCCGACGATCGGACTGATCGGACTGAGTGCCTCAATGCAACCAGTACTCCATGCGT
ACAAGTGCAGCAGACTGTCTGCTGTCCGACGATCGGAAGACGGAAGATTACTATCGGAAGCAGCTGAGCCTGGAGGCGGCTGG
GAGCATCGTCCCTCAACGGTGTGCAAGTGGTGCAACAGTGCCAGGAGCCTGGAGCCTGGCAAAGCTGAGGCCTGGCAATGCACCCGTCAGTACGGCAC
GCTGGTGGCAAGGTCAACAGTGCGCCAGCACCGTGCGCCAAGTGGGCAAGTCAGGAAATTGCAAGTCAGGTGGGCAATTGCGTGGAGG
CGATACAAATTCGTCTGTCCTAAGCTGGAATTTGCTAACGACACAAAATTGCAAGTCAGTACAGCCGGTGCGACAGCAGAGGTTCGTGT
TACTTCTCTGTATGGAGTGAGTGAGACCTGGTCTACTATTCCGAGAACTGTACAGCCCTGTTCCGGCCTGCGGGACCCCTGCAGACTCT
ACGATGCTTATCAGAACCTGGTCGGTACTATTCCGAGAACGATGGAAAATTACTATTGCCTGCGAGCATGCGGAGCGTCCC
AGTGCTCCGTCATCTACGACGAGGAAACTAAAACCCACGCAAACCCTGTTCCGGCCTGCGAGCATATTAGCTCC
ACCATGAGCCAGTATAGCAGATCCACACGGTCTGTCCATGCGAAAACGGCGACTCTCAGTTCGTGAAGATTGCAAGTGCCACTGGACAGTCTCTGCG
GTGGGGTGCGTGGCGTGCAACAGTGCCAGCACCAGCAGCGCGCGCAACGTCTAGTCTGTCGTCAAGCTTCGACTGCAAGATGCCACTGGCACTGGCACAGTCTCTGCC
CACTGCCAGACACACCCAGTACTGACTGACAAGCTTTAACTGCAAGATGCCACTGGCACAACGTCATCCCAACAACTTCAGCTTTGCC
CCTTCAATCAATGAACTATTCAGGTGACTGCAAAACAGTACGTGACCCCGTGCAAACAGTAACAGTACGTCGAAACGTAACAGTACGTCGAAACAGTACGTCAATCCCACAACTTCAGCTTTGCC
GTGACTCAGGAGGTATATCCAGAACAACTATCAGAAAGGTGACCGTCGACTGCAAAACAGTACGTGACTACGTCGAAATGCAATGATCCAG

FIG. 8C

```
AAATGGCGAACAGCTGCTGCGGGAGTATGGGCAGTTTGTTCCAAGATCAATCAGGCACTGCATGGCGCCAACCTGCGC
CAGGACGATAGTGTGCGAAACCTGTTCGCCCTCAGTCAAGTCCTCTCAGAGTTCACCTATCATTCCAGGTTCGGCGGCG
ACTTCAACCTGACCCTGCTGAACCCGTGAGCATCAGTAGTACCGGCAGCAGGAGCGCCAGAAGCGCAATCGAGGATCGC
TGTTTGACAAAGTGACCATTGCCGACCCAGGATACATGCAGGGTATGACGATTGCAGCAGGGACCAGCAGCATCCG
CTCGCGATCTGATCTGTGCTCAGTACGTGGCAGGGTATAAGGTCCTGCCACCCTGATGACGTGAACATGGAAGCTGC
ATATACTAGTCCCTGTGGGGAGCATTGCAGGAGTGGGATGGACCGGTGGACTGTCTAGTTTCGCCGCTATCCCATTT
GCTCAGAGCATTTTCTACAGGCCTGAACGCGCTGTGGGAATCACTCAGCAGGTCCTGTCCGAGAATCAGAAGCTGATTGCC
AACAAGTTCAACCAGGCCCTGGAGTATGCAGACGGGTTTACCACACAACTAACGAAGCTTTCCGCAAAGTGCAGGAC
GCAGTCAACAATAACGCACAGCCCTGTCCAAGCTGGCTTCTGAGCTGAGTAATACATTCGGAGCAATCTCCGCCTCTA
TTGGGGATATCATTCAGAGAGGCTGGAGCAGGATGCGGCTGATTAATGACGGCTGACCA
CACTGAAGCGCTTTTGTGGCACAGCAGCTGGTTCCGAAGTGAATCAGCAGCCCTGTCTGCCCAGCTGGCTAAGGACAAAG
ATGCACCTAACGGGCCTGTACTTTATGCACGTGGGGATACTATCCAAGCAACATATCGAGGTGGTCTCCGCTTATGCCT
TGAACGAGTGCGTCAAGGCTCAGTCAAAACGGAGCGGCTTTTGTGGGCAGGGCACCCACATCGTGAGCTTCGTGGTCA
GTGCTGCTGCAAATCCTACTTTATGCACCAGTGAACGGATACTTCATCAAACTAACACCAGATTGTG
GACGAATGGTCATACACTGGCTCAAGCTTTATGCACCCGAGCCTATCACCTCCCTGAACACAAAGTACGTGGCCCAC
ATGTCACCTATCAGAATATCTCCACAAACCTGCCTCACCCTGCTGGGCAATTCTACCGGCAATTTGACTTCCAGGATGA
ACTGGACGAGTTCTTTAAGAATGTGAGCACATCCCCAACTTTGGAAGCCTGACTCAGATTAACACTACCCTGCTG
GATCTGACCTACGAGATGCTGAGTCTGCAGCAGACTGGGGTCAAGGCCCTGAATGAATCATACATGCGACCTGAAAGAGCTG
GGGAATTATACATACTATAACAAGTGGCCCTGGTACTCGGATGCGGGACCAACTGTATGGGCAAGCTGTATGGGTGCACTGT
GCGTCTTCTTTATCTAATGACTGTGCTGTACTGATGCGGGAGCCCATAAAGTGCATGTCCACTAATGA (SEQ ID NO:3)
```

FIG. 8C (con't)

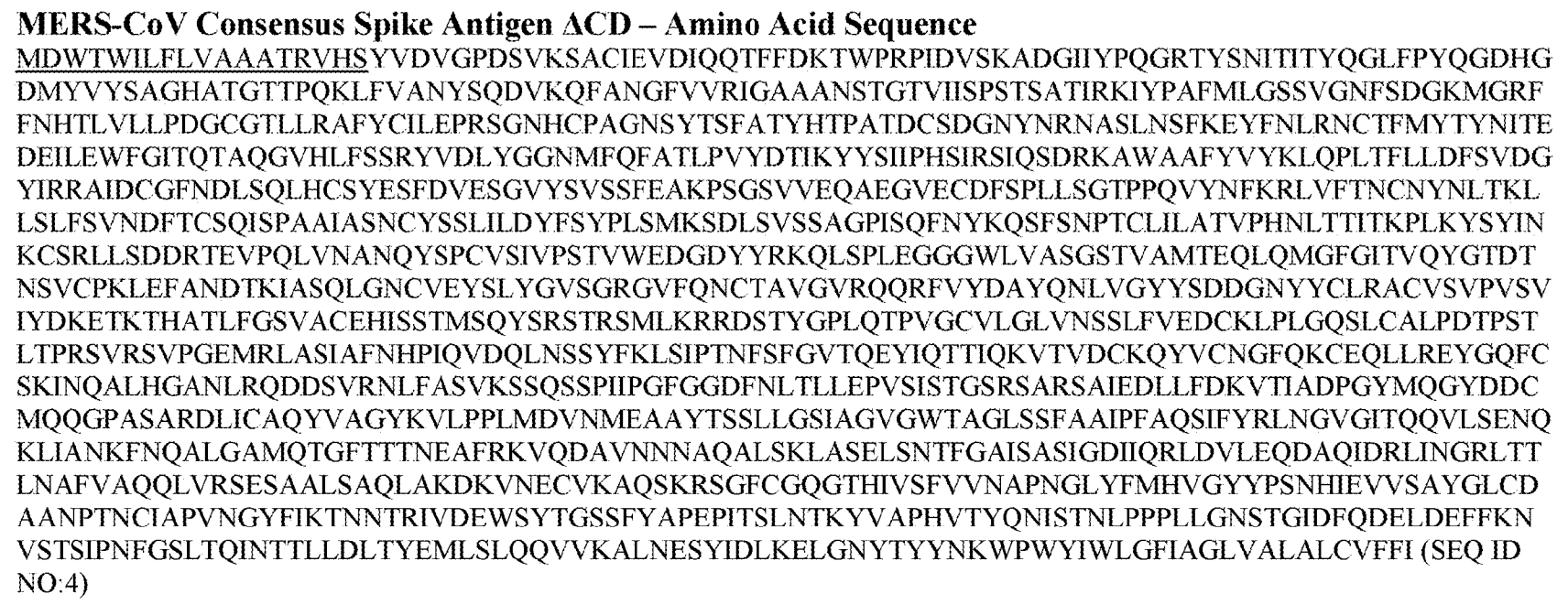

MERS-CoV Consensus Spike Antigen ΔCD – Amino Acid Sequence

MDWTWILFLVAAATRVHSYVDVGPDSVKSACIEVDIQQTFFDKTWPRPIDVSKADGIIYPQGRTYSNITITYQGLFPYQGDHG
DMYVYSAGHATGTTPQKLFVANYSQDVKQFANGFVVRIGAAANSTGTVIISPSTSATIRKIYPAFMLGSSVGNFSDGKMGRF
FNHTLVLLPDGCGTLLRAFYCILEPRSGNHCPAGNSYTSFATYHTPATDCSDGNYNRNASLNSFKEYFNLRNCTFMYTYNITE
DEILEWFGITQTAQGVHLFSSRYVDLYGGNMFQFATLPVYDTIKYYSIIPHSIRSIQSDRKAWAAFYVYKLQPLTFLLDFSVDG
YIRRAIDCGFNDLSQLHCSYESFDVESGVYSVSSFEAKPSGSVVEQAEGVECDFSPLLSGTPPQVYNFKRLVFTNCNYNLTKL
LSLFSVNDFTCSQISPAAIASNCYSSLILDYFSYPLSMKSDLSVSSAGPISQFNYKQSFSNPTCLILATVPHNLTTITKPLKYSYIN
KCSRLLSDDRTEVPQLVNANQYSPCVSIVPSTVWEDGDYYRKQLSPLEGGGWLVASGSTVAMTEQLQMGFGITVQYGTDT
NSVCPKLEFANDTKIASQLGNCVEYSLYGVSGRGVFQNCTAVGVRQQRFVYDAYQNLVGYYSDDGNYYCLRACVSVPVSV
IYDKETKTHATLFGSVACEHISSTMSQYSRSTRSMLKRRDSTYGPLQTPVGCVLGLVNSSLFVEDCKLPLGQSLCALPDTPST
LTPRSVRSVPGEMRLASIAFNHPIQVDQLNSSYFKLSIPTNFSFGVTQEYIQTTIQKVTVDCKQYVCNGFQKCEQLLREYGQFC
SKINQALHGANLRQDDSVRNLFASVKSSQSSPIIPGFGGDFNLTLLEPVSISTGSRSARSAIEDLLFDKVTIADPGYMQGYDDC
MQQGPASARDLICAQYVAGYKVLPPLMDVNMEAAYTSSLLGSIAGVGWTAGLSSFAAIPFAQSIFYRLNGVGITQQVLSENQ
KLIANKFNQALGAMQTGFTTTNEAFRKVQDAVNNNAQALSKLASELSNTFGAISASIGDIIQRLDVLEQDAQIDRLINGRLTT
LNAFVAQQLVRSESAALSAQLAKDKVNECVKAQSKRSGFCGQGTHIVSFVVNAPNGLYFMHVGYYPSNHIEVVSAYGLCD
AANPTNCIAPVNGYFIKTNNTRIVDEWSYTGSSFYAPEPITSLNTKYVAPHVTYQNISTNLPPPLLGNSTGIDFQDELDEFFKN
VSTSIPNFGSLTQINTTLLDLTYEMLSLQQVVKALNESYIDLKELGNYTYYNKWPWYIWLGFIAGLVALALCVFFI (SEQ ID
NO:4)

| Matrix Setup | Pool 16 | Pool 17 | Pool 18 | Pool 19 | Pool 20 | Pool 21 | Pool 22 | Pool 23 | Pool 24 | Pool 25 | Pool 26 | Pool 27 | Pool 28 | Pool 29 | Pool 30 | Pool 31 |
|---|---|---|---|---|---|---|---|---|---|---|---|---|---|---|---|---|
| Pool 1 | 2 | 3 | 4 | 5 | 6 | 7 | 8 | 9 | 10 | 11 | 12 | 13 | 14 | 15 | 16 | 17 |
| Pool 2 | 18 | 19 | 20 | 21 | 22 | 23 | 24 | 25 | 26 | 27 | 28 | 29 | 30 | 31 | 32 | 33 |
| Pool 3 | 34 | 35 | 36 | 37 | 38 | 39 | 40 | 41 | 42 | 43 | 44 | 45 | 46 | 47 | 48 | 49 |
| Pool 4 | 50 | 51 | 52 | 53 | 54 | 55 | 56 | 57 | 58 | 59 | 60 | 61 | 62 | 63 | 64 | 65 |
| Pool 5 | 66 | 67 | 68 | 69 | 70 | 71 | 72 | 73 | 74 | 75 | 76 | 77 | 78 | 79 | 80 | 81 |
| Pool 6 | 82 | 83 | 84 | 85 | 86 | 87 | 88 | 89 | 90 | 91 | 92 | 93 | 94 | 95 | 96 | 97 |
| Pool 7 | 98 | 99 | 100 | 101 | 102 | 103 | 104 | 105 | 106 | 107 | 108 | 109 | 110 | 111 | 112 | 113 |
| Pool 8 | 114 | 115 | 116 | 117 | 118 | 119 | 120 | 121 | 122 | 123 | 124 | 125 | 126 | 127 | 128 | 129 |
| Pool 9 | 130 | 131 | 132 | 133 | 134 | 135 | 136 | 137 | 138 | 139 | 140 | 141 | 142 | 143 | 144 | 145 |
| Pool 10 | 146 | 147 | 148 | 149 | 150 | 151 | 152 | 153 | 154 | 155 | 156 | 157 | 158 | 159 | 160 | 161 |
| Pool 11 | 162 | 163 | 164 | 165 | 166 | 167 | 168 | 169 | 170 | 171 | 172 | 173 | 174 | 175 | 176 | 177 |
| Pool 12 | 178 | 179 | 180 | 181 | 182 | 183 | 184 | 185 | 186 | 187 | 188 | 189 | 190 | 191 | 192 | 193 |
| Pool 13 | 194 | 195 | 196 | 197 | 198 | 199 | 200 | 201 | 202 | 203 | 204 | 205 | 206 | 207 | 208 | 209 |
| Pool 14 | 210 | 211 | 212 | 213 | 214 | 215 | 216 | 217 | 218 | 219 | 220 | 221 | 222 | 223 | 224 | 225 |
| Pool 15 | 226 | 227 | xxx | xxx | xxx | xxx | xxx | xxx | xxx | xxx | xxx | xxx | xxx | xxx | xxx | xxx |

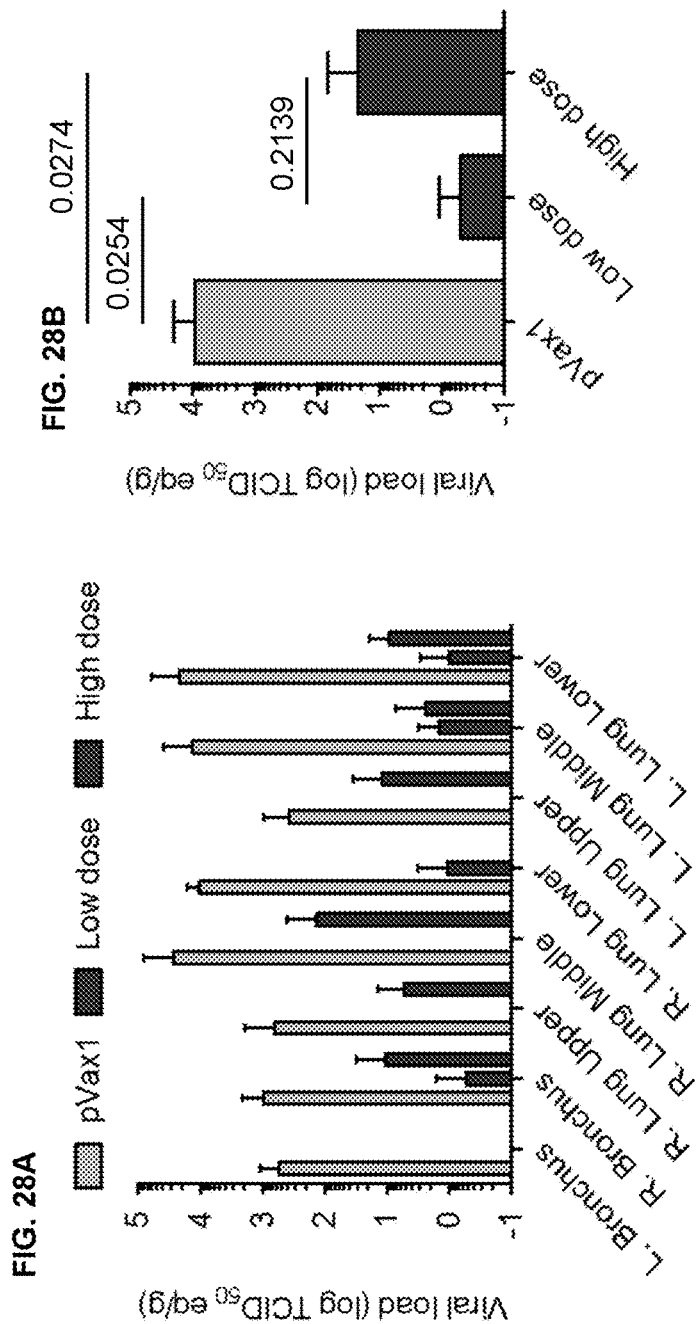

MERS-COV VACCINE

CROSS-REFERENCE TO RELATED APPLICATIONS

The present application is a continuation of U.S. patent application Ser. No. 15/039,672, filed May 26, 2016, now allowed, which is a U.S. national phase application filed under 35 U.S.C. § 371 claiming benefit to International Patent Application No. PCT/US2014/067537, filed Nov. 26, 2014, which is entitled to priority under 35 U.S.C § 119(e) to U.S. Provisional Patent Application No. 61/910,153, filed Nov. 29, 2013, each of which applications are incorporated by reference herein in their entireties.

TECHNICAL FIELD

The present invention relates to a vaccine for Middle East Respiratory Syndrome coronavirus (MERS-CoV) and a method of administering the vaccine.

BACKGROUND

Coronaviruses (CoV) are a family of viruses that are common worldwide and cause a range of illnesses in humans from the common cold to severe acute respiratory syndrome (SARS). Coronaviruses can also cause a number of diseases in animals. Human coronaviruses 229E, OC43, NL63, and HKU1 are endemic in the human population.

In 2012, a novel coronavirus (nCoV) emerged in Saudi Arabia and is now known as Middle East Respiratory Syndrome coronavirus (MERS-CoV) (FIG. 1). MERS-CoV can be classified as a beta coronavirus (FIG. 2, starred MERS-CoV strain HCoV-EMC/2012). Subsequent cases of MERS-CoV infection have been reported elsewhere in the Middle East (e.g., Qatar and Jordan) and more recently in Europe. Infection with MERS-CoV presented as severe acute respiratory illness with symptoms of fever, cough, and shortness of breath. About half of reported cases of MERS-CoV infection have resulted in death and a majority of reported cases have occurred in older to middle age men. Only a small number of reported cases involved subjects with mild respiratory illness. Human to human transmission of MERS-CoV is possible, but very limited at this time.

Accordingly, a need remains in the art for the development of a safe and effective vaccine that is applicable to MERS-CoV, thereby providing protection against and promoting survival of MERS-CoV infection.

SUMMARY

The present invention is directed to an immunogenic composition. In one embodiment, the invention is directed to a vaccine comprising a nucleic acid molecule, wherein the nucleic acid molecule can comprise a nucleic acid sequence having at least about 90% identity over an entire length of the nucleic acid sequence set forth in SEQ ID NO:1 or the nucleic acid molecule can comprise a nucleic acid sequence having at least about 90% identity over an entire length of the nucleic acid sequence set forth in SEQ ID NO:3.

The present invention is also directed to a vaccine comprising a nucleic acid molecule, wherein the nucleic acid molecule can encode a peptide comprising an amino acid sequence having at least about 90% identity over an entire length of the amino acid sequence set forth in SEQ ID NO:2 or the nucleic acid molecule can encode a peptide comprising an amino acid sequence having at least about 90% identity over an entire length of the amino acid sequence set forth in SEQ ID NO:4.

The present invention is further directed to a nucleic acid molecule comprising the nucleic acid sequence set forth in SEQ ID NO:1.

The present invention is further directed to a nucleic acid molecule comprising the nucleic acid sequence set forth in SEQ ID NO:3.

The present invention is further directed to a peptide comprising the amino acid sequence set forth in SEQ ID NO:2.

The present invention is further directed to a peptide comprising the amino acid sequence set forth in SEQ ID NO:4.

The present invention is further directed to a vaccine comprising an antigen, wherein the antigen is encoded by SEQ ID NO:1 or SEQ ID NO:3.

The present invention is also directed to a vaccine comprising a peptide, wherein the peptide can comprise an amino acid sequence having at least about 90% identity over an entire length of the amino acid sequence set forth in SEQ ID NO:2 or the peptide can comprise an amino acid sequence having at least about 90% identity over an entire length of the amino acid sequence set forth in SEQ ID NO:4.

The present invention is further directed to a method of inducing an immune response against a Middle East Respiratory Syndrome coronavirus (MERS-CoV) in a subject in need thereof. The method can comprise administering one or more of the above vaccines, nucleic acid molecules, or peptides to the subject.

The present invention is further directed to a method of protecting a subject in need thereof from infection with a Middle East Respiratory Syndrome coronavirus (MERS-CoV). The method can comprise administering one or more of the above vaccines, nucleic acid molecules, or peptides to the subject.

The present invention is further directed to a method of treating a subject in need thereof against Middle East Respiratory Syndrome coronavirus (MERS-CoV). The method can comprise administering one or more of the above vaccines, nucleic acid molecules, or peptides to the subject.

BRIEF DESCRIPTION OF THE DRAWINGS

FIG. 4A shows a schematic illustrating the MERS-HCoV-WT construct; and FIG. 4B shows an image of a stained gel.

FIG. 8A shows a nucleotide sequence encoding a MERS-CoV consensus spike antigen; FIG. 8B shows the amino acid sequence of the MERS-CoV consensus spike antigen;

FIG. 8C shows a nucleotide sequence encoding a MERS-CoV consensus spike antigen that lacks the cytoplasmic domain (MERS-CoV consensus spike antigen ΔCD); and FIG. 8D shows the amino acid sequence of the MERS-CoV consensus spike antigen ΔCD.

FIG. 12 shows a matrix of peptide pools.

FIG. 15 shows a graph plotting immunization group vs. spot forming unit per $10^6$ cells (SFU/$10^6$ cells).

FIG. 19, comprising FIG. 19A provides dendograms showing the phylogenetic relationships between the MERS-HCoV viral isolates and Spike vaccine strains at the amino acid level. A rooted neighbor joining tree was generated from amino acid sequence alignments of Spike protein with the consensus vaccine displayed as (★) and (❖) denotes the MERS-viral strain used to test the Nab assay. The shaded area represents reported cases from the 2012-2013 outbreaks. Parenthesis indicated the specific clades. The tree was drawn to scale (scale bar, 0.1 percent difference). FIG. 19B provides a schematic diagram of Spike-Wt gene inserts used in codon optimized DNA vaccines. Spike-Wt and SpikeΔCD-DNA vaccines were constructed. Different Spike protein domains were indicated. FIG. 19C shows that expression of protein was detected by Western blot. The expression of Spike-Wt and SpikeΔCD-Spike protein was analyzed two days post transfection by Western blotting using sera from the MERS-Spike-Wt DNA vaccinated mice at 1:100 dilutions. DNA construct transfected and amount of cell lysates loaded as indicated. Arrow indicated the Spike protein. FIG. 19D shows an immune fluorescence assay in Vero cells, which showed the Spike-Wt and SpikeΔCD protein expression using the sera (1:100) from DNA immunized mice.

FIG. 20, comprising FIG. 20A provides a schematic representation of MERS-HCoV-Spike pesudovirus. FIG. 20B shows the determination of viral infectivity: Vero cells were incubated with MERS-Spike pseudo-typed with Luciferase reporter backbone. Luciferase reporter activity was then assayed at the indicated times to produce a time course of expression. Curves were fitted to the data by non-linear regression analysis and the best fit was a straight line. FIG. 20C shows the detection of MERS-HCoV-Spike pseudovirus infectivity in different cell lines. MERS-Spike pseudoviruses and the negative control VSV-G virus were used for the infection. The data were expressed as mean relative luciferase units (RLU)±standard deviation (SD) of 3 parallel wells in 96-well culture plates. The experiment was repeated three times, and similar results were obtained.

FIG. 21, comprising FIG. 21A shows that groups of C57/BL6 mice (n=9/group) were immunized three times, each 2 weeks apart with 25 μg of Spike-Wt and Spike ΔCD DNA vaccine as indicated. Samples were collected a week after the third immunization. FIG. 21B shows that spike-specific T-lymphocyte responses were assessed by IFN-γ ELISpot assays using 6 peptide pools covering the Spike protein. Values represented mean responses in each group one week after the third immunization. Error bars indicated standard errors. FIG. 21C and FIG. 21D show the characterization of MERS-Spike-specific dominant epitopes. Secretion of IFN-γ by splenocytes from MERS-Spike-specific immune responses using matrix pooling of peptides. The results were expressed as the number of IFN-γ secreting cells/$10^6$ spleen cells (mean±SD for three mice per group) after subtracting values without peptide stimulation. Similar results were obtained in two separate experiments.

FIG. 22, comprising FIG. 22A shows the serum anti-IgG responses in mice measured by ELISA with as indicated serum dilution against MERS-Spike as coating antigen. Pooled serum from individual groups of mice (one week after the 3rd immunization) was serially diluted and MERS-Spike-specific total IgG was measured by ELISA. Each curve represented the OD value of each group of 9 mice receiving Spike-Wt DNA vaccine, SpikeΔCD-Spike DNA vaccine or empty DNA vector as indicated. Each data point was the average absorbance from nine mice. FIG. 22B shows the endpoint titer for the Spike-Wt immunized mice sera were calculated at the indicated time points. FIG. 22C shows a western blot analysis of immunized sera binding to recombinant Spike protein at indicated concentrations (μg). Pooled sera from the Spike-Wt immunized mice was used as the primary antibody at 1:100 dilution. FIG. 22D shows the neutralizing antibody responses detected by the viral infection assay.

Sera, at one week after the third immunization, were collected from the immunized mice. Neutralizing antibody titers were measured at 50% inhibition ($IC_{50}$) of virus infection to target cells. Data shown were the geometric mean titers of each group with standard deviations. The statistical differences between each testing group were determined and p values were indicated. FIG. 22E shows the neutralization of the infectivity of MERS-Spike-pseudotyped viruses by antisera obtained from mice after receiving three injections of Spike-Wt DNA or pVax1 DNA. The $IC_{50}$ was defined as the reciprocal of the antiserum dilution at which virus entry is 50% inhibited (dashed line). Data from 4 mice per each group were shown.

FIG. 23, comprising FIG. 23A shows the study design, vaccine and challenge regimen in rhesus monkeys. Three groups (low, high and control) of rhesus monkeys (n=4/each group) were immunized with MERS-Spike DNA at 0, 3, and 6 weeks (wks) as indicated. IFN-γ ELISpot, intracellular cytokine staining and antibody binding and Nab assay were performed from the 3rd immunization samples. Biopsies were performed following MERS-Challenge. FIG. 23B shows an ELISPOT analysis of cells from MERS-Spike DNA-immunized monkeys. PBMCs were isolated from each of DNA-immunized monkeys and were used for ELISPOT assay to detect IFN-γ-producing cells responding to pools of MERS-Spike peptides for 24 hours as described in Example 9. Frequencies of MERS-Spike specific IFN-γ-secreting cells/$10^6$ PBMCs were determined by ELISpot assay. Results were presented as mean±SEM. FIG. 23C shows the frequency of vaccine induced cytokine (IFN-γ, IL-2, or TNF-α) producing $CD4^+$ and $CD8^+$ T cells. Macaques PBMC's (n=4) were isolated after the final DNA immunization and were stimulated with pooled MERS-Spike peptide ex-vivo. Cells were stained for intracellular production of IFN-γ, TNF-α, and IL-2, and then analyzed by multi parameter flow cytometry.

FIG. 24, comprising FIG. 24A and FIG. 24B show MERS-Specific antibodies in serum binding and IgG specific end point titers at various times post-immunization. Serum was collected after each vaccination and endpoint titers calculated by ELISA. FIG. 24C and FIG. 24D show the effect of DNA vaccinations and characterization of the neutralizing antibody response. Blood samples were obtained from the animals prior to each immunization and two weeks after the final vaccination. The sera were tested for neutralizing antibody. Neutralization with live virus (FIG. 24C) or MERS-pseudovirus (FIG. 24D). Serially diluted immunized sera were tested with MERS-virus. For the pseudovirus neutralization assay, an anti-CHIKV monkey serum was used as a negative antibody control, and VSV-G pseudotyped virus was used as pseudovirus control for neutralization specificity. Samples were tested by PRNT50 assay with MERS virus.

FIG. 25, comprising FIG. 25A and FIG. 25B provide scatter plots depicting MERS-specific $CD4^+$ T and $CD8^+$ T cells releasing IFN-γ, TNF-α, IL-2 and dual IFN-γ/TNF-α cytokines. FIG. 25C and FIG. 25D provide column graph shows multifunctional subpopulations of single-, double- and triple-positive $CD4^+$ and $CD8^+$ T cells releasing the cytokines IFN-γ, TNF-α, and IL-2. The pie charts show the proportion of each cytokine subpopulation. Data represented mean±SEM of three mice per group.

FIG. 26, comprising FIG. 26A shows MERS-HCoV-Spike mouse sera neutralized MERS in vitro and blocks syncytia formation. Vero cells, which were uninfected, represented a negative control, whereas the positive control represented those cells infected with MERS-HCoV pseudovirus. Arrow indicated the syncytia formation. Syncytia formation was observed under the microscope 36 hours post infection. FIG. 26B shows MERS-Spike pseudoviruses pre-incubated in the presence of either pVax-1 or MERS-Spike immunized sera at 1:100 dilutions and added to the Vero cells. Two days post infection, the percentage of cell death was measured by the Annexin V/PI staining. Bar graph indicated the infection of MERS-pseudovirus values from the FACS data for a single experiment carried out in triplicate. Similar results were obtained in three independent experiments.

FIG. 27, comprising

FIG. 28, comprising FIG. 28A through FIG. 28B, shows results from MERS challenge post-vaccination and pathobiology. FIG. 28A shows the mean viral load determined by qRT-PCR from individual tissues collected at necropsy. FIG. 28B shows the mean viral load of all lung lobes combined is indicated in the inset. Log TCID50 eq/g, log TCID50 equivalents per gram tissue; one sample per tissue per animal from three animals per group were analyzed.

DETAILED DESCRIPTION OF THE INVENTION

Figure 1:
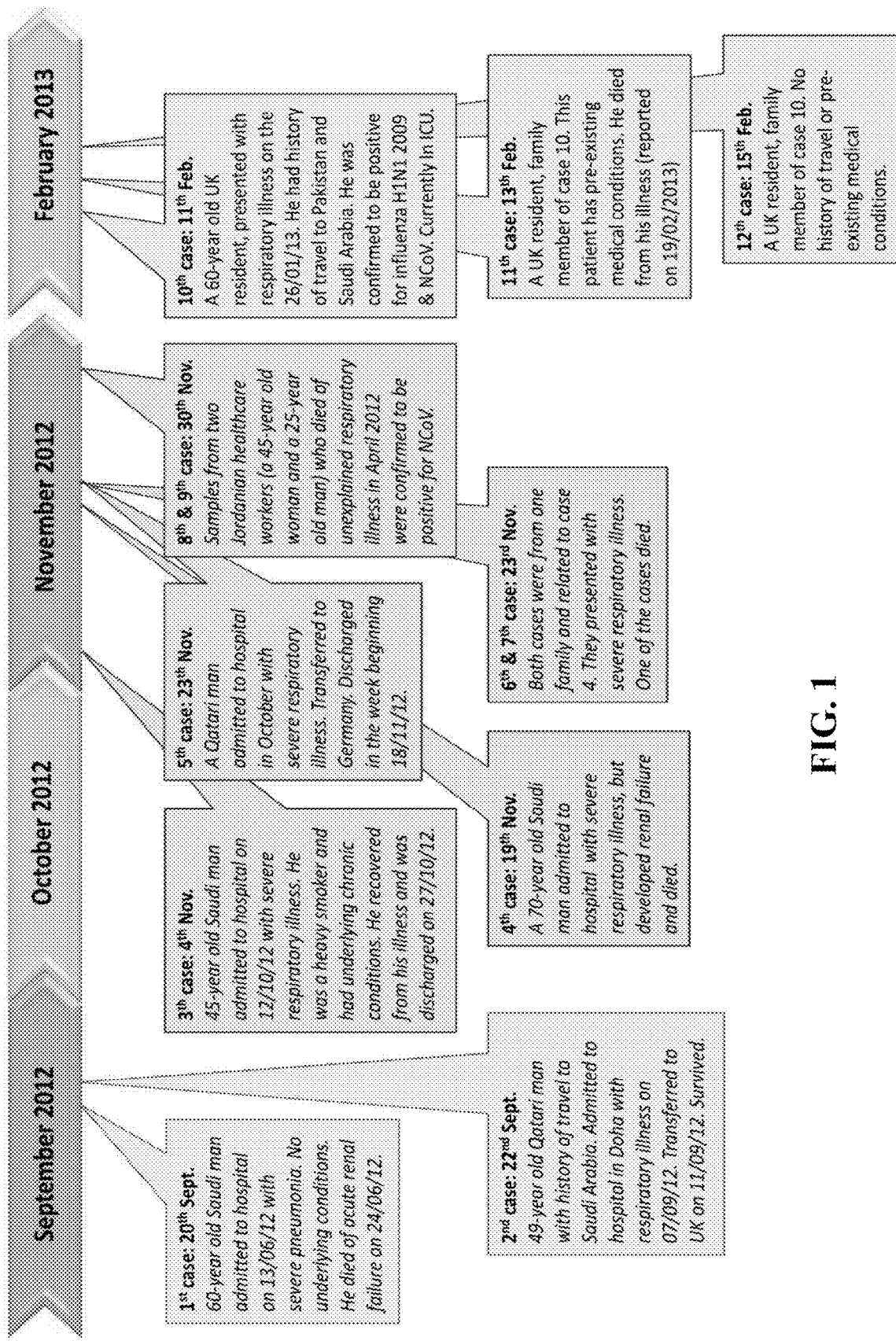
FIG. 1 shows a timeline illustrating the emergence of MERS-CoV.
Figure 2:
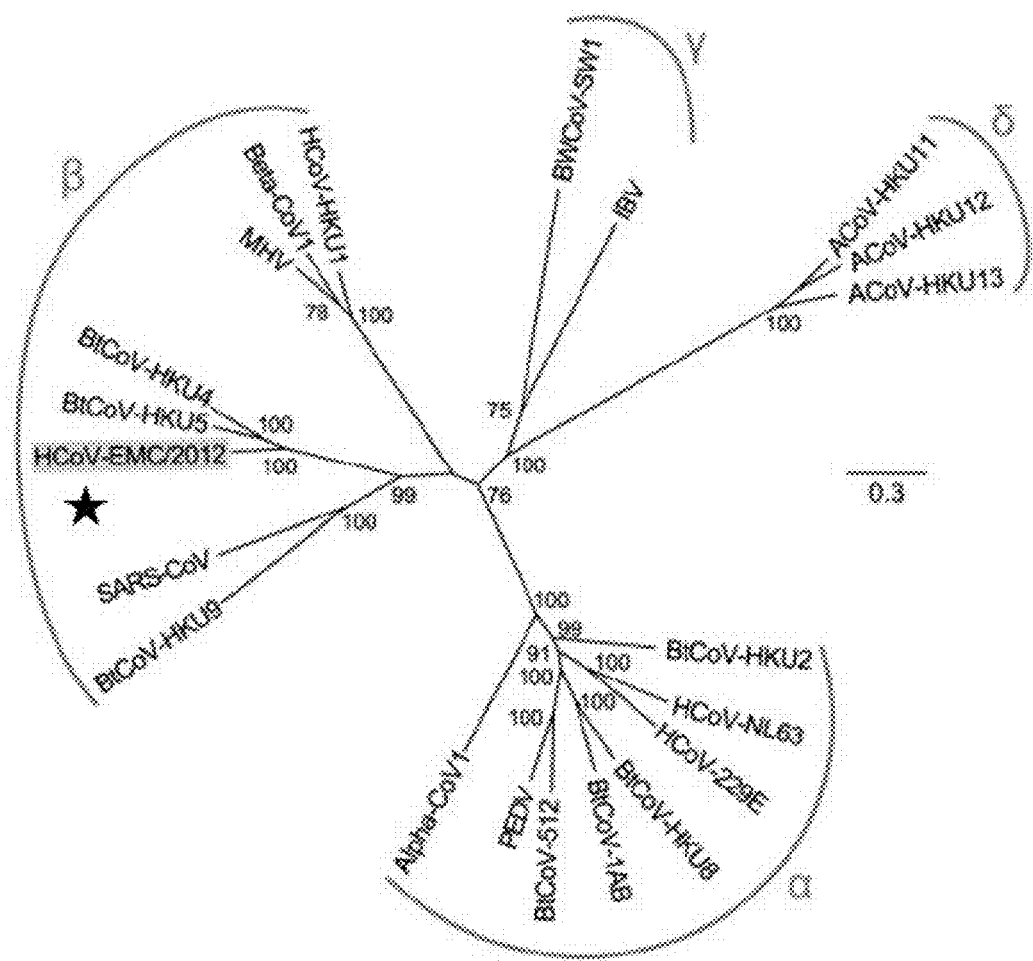
FIG. 2 shows a phylogenetic tree depicting the relationship between the indicated coronaviruses.

The present invention relates to a vaccine comprising a Middle East Respiratory Syndrome coronavirus (MERS-CoV) antigen. MERS-CoV is a new and highly pathogenic virus, only emerging in 2012, and thus, the vaccine described herein is one of the first vaccines to target MERS-CoV. Accordingly, the vaccine provides a treatment for this new and pathogenic virus, for which prior treatment did not exist and potential for a pandemic remains.

The MERS-CoV antigen can be a MERS-CoV consensus spike antigen. The MERS-CoV consensus spike antigen can be derived from the sequences of spike antigens from strains of MERS-CoV, and thus, the MERS-CoV consensus spike antigen is unique. The MERS-CoV consensus spike antigen can lack a cytoplasmic domain. Accordingly, the vaccine of the present invention is widely applicable to multiple strains of MERS-CoV because of the unique sequences of the MERS-CoV consensus spike antigen. These unique sequences allow the vaccine to be universally protective against multiple strains of MERS-CoV, including genetically diverse variants of MERS-CoV.

The vaccine can be used to protect against and treat any number of strains of MERS-CoV. The vaccine can elicit both humoral and cellular immune responses that target the MERS-CoV spike antigen. The vaccine can elicit neutralizing antibodies and immunoglobulin G (IgG) antibodies that are reactive with the MERS-CoV spike antigen. The vaccine can also elicit CD8+ and CD4+ T cell responses that are reactive to the MERS-CoV spike antigen and produce interferon-gamma (IFN-γ), tumor necrosis factor alpha (TNF-α), and interleukin-2 (IL-2).

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein means any molecule added to the vaccine described herein to enhance the immunogenicity of the antigen.

"Antibody" as used herein means an antibody of classes IgG, IgM, IgA, IgD or IgE, or fragments, fragments or derivatives thereof, including Fab, F(ab')$_2$, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to generate consensus sequences (or consensus antigens).

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein means a nucleic acid sequence or a portion thereof that encodes a polypeptide capable of eliciting an immune response in a mammal. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length wild type strain MERS-CoV antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a MERS-CoV protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that wants to or is in need of being immunized with the herein described vaccine. The mammal can be a human, chimpanzee, dog, cat, horse, cow, mouse, or rat.

"Substantially identical" as used herein can mean that a first and second amino acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more amino acids. Substantially identical can also mean that a first nucleic acid sequence and a second nucleic acid sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides.

"Treatment" or "treating," as used herein can mean protecting of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. VACCINE

Provided herein are immunogenic compositions, such as vaccines, comprising a Middle East Respiratory Syndrome coronavirus (MERS-CoV) antigen, a fragment thereof, a variant thereof, or a combination thereof. The vaccine can be used to protect against any number of strains of MERS-CoV, thereby treating, preventing, and/or protecting against MERS-CoV based pathologies. The vaccine can significantly induce an immune response of a subject administered the vaccine, thereby protecting against and treating MERS-CoV infection.

The vaccine can be a DNA vaccine, a peptide vaccine, or a combination DNA and peptide vaccine. The DNA vaccine can include a nucleic acid sequence encoding the MERS-CoV antigen. The nucleic acid sequence can be DNA, RNA, cDNA, a variant thereof, a fragment thereof, or a combination thereof. The nucleic acid sequence can also include additional sequences that encode linker, leader, or tag sequences that are linked to the MERS-CoV antigen by a peptide bond. The peptide vaccine can include a MERS-CoV antigenic peptide, a MERS-CoV antigenic protein, a variant thereof, a fragment thereof, or a combination thereof. The combination DNA and peptide vaccine can include the above described nucleic acid sequence encoding the MERS-CoV antigen and the MERS-CoV antigenic peptide or protein, in which the MERS-CoV antigenic peptide or protein and the encoded MERS-CoV antigen have the same amino acid sequence.

The vaccine can induce a humoral immune response in the subject administered the vaccine. The induced humoral immune response can be specific for the MERS-CoV antigen. The induced humoral immune response can be reactive with the MERS-CoV antigen. The humoral immune response can be induced in the subject administered the vaccine by about 1.5-fold to about 16-fold, about 2-fold to about 12-fold, or about 3-fold to about 10-fold. The humoral immune response can be induced in the subject administered the vaccine by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold.

The humoral immune response induced by the vaccine can include an increased level of neutralizing antibodies associated with the subject administered the vaccine as compared to a subject not administered the vaccine. The neutralizing antibodies can be specific for the MERS-CoV antigen. The neutralizing antibodies can be reactive with the MERS-CoV antigen. The neutralizing antibodies can provide protection against and/or treatment of MERS-CoV infection and its associated pathologies in the subject administered the vaccine.

The humoral immune response induced by the vaccine can include an increased level of IgG antibodies associated with the subject administered the vaccine as compared to a subject not administered the vaccine. These IgG antibodies can be specific for the MERS-CoV antigen. These IgG antibodies can be reactive with the MERS-CoV antigen. Preferably, the humoral response is cross-reactive against two or more strains of the MERS-CoV. The level of IgG antibody associated with the subject administered the vaccine can be increased by about 1.5-fold to about 16-fold, about 2-fold to about 12-fold, or about 3-fold to about 10-fold as compared to the subject not administered the vaccine. The level of IgG antibody associated with the subject administered the vaccine can be increased by at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 15.5-fold, or at least about 16.0-fold as compared to the subject not administered the vaccine.

The vaccine can induce a cellular immune response in the subject administered the vaccine. The induced cellular immune response can be specific for the MERS-CoV antigen. The induced cellular immune response can be reactive to the MERS-CoV antigen. Preferably, the cellular response is cross-reactive against two or more strains of the MERS-CoV. The induced cellular immune response can include eliciting a CD8$^+$ T cell response. The elicited CD8$^+$ T cell response can be reactive with the MERS-CoV antigen. The elicited CD8$^+$ T cell response can be polyfunctional. The induced cellular immune response can include eliciting a CD8$^+$ T cell response, in which the CD8$^+$ T cells produce interferon-gamma (IFN-$\gamma$), tumor necrosis factor alpha (TNF-$\alpha$), interleukin-2 (IL-2), or a combination of IFN-$\gamma$ and TNF-$\alpha$.

The induced cellular immune response can include an increased CD8$^+$ T cell response associated with the subject administered the vaccine as compared to the subject not administered the vaccine. The CD8$^+$ T cell response associated with the subject administered the vaccine can be increased by about 2-fold to about 30-fold, about 3-fold to about 25-fold, or about 4-fold to about 20-fold as compared to the subject not administered the vaccine. The CD8$^+$ T cell response associated with the subject administered the vaccine can be increased by at least about 1.5-fold, at least about 2.0-fold, at least about 3.0-fold, at least about 4.0-fold, at least about 5.0-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, at least about 15.0-fold, at least about 16.0-fold, at least about 17.0-fold, at least about 18.0-fold, at least about 19.0-fold, at least about 20.0-fold, at least about 21.0-fold, at least about 22.0-fold, at least about 23.0-fold, at least about 24.0-fold, at least about 25.0-fold, at least about 26.0-fold, at least about 27.0-fold, at least about 28.0-fold, at least about 29.0-fold, or at least about 30.0-fold as compared to the subject not administered the vaccine.

The induced cellular immune response can include an increased frequency of CD3$^+$CD8$^+$ T cells that produce IFN-$\gamma$. The frequency of CD3$^+$CD8$^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3$^+$CD8$^+$ T cells that produce TNF-$\alpha$. The frequency of CD3$^+$CD8$^+$TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, or 14-fold as compared to the subject not administered the vaccine.

The induced cellular immune response can include an increased frequency of CD3$^+$CD8$^+$ T cells that produce IL-2. The frequency of CD3$^+$CD8$^+$IL-2$^+$ T cells associated with the subject administered the vaccine can be increased by at least about 0.5-fold, 1.0-fold, 1.5-fold, 2.0-fold, 2.5-fold, 3.0-fold, 3.5-fold, 4.0-fold, 4.5-fold, or 5.0-fold as compared to the subject not administered the vaccine.

The induced cellular immune response can include an increased frequency of CD3$^+$CD8$^+$ T cells that produce both IFN-$\gamma$ and TNF-$\alpha$. The frequency of CD3$^+$CD8$^+$IFN-$\gamma^+$TNF-$\alpha^+$ T cells associated with the subject administered the vaccine can be increased by at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 110-fold, 120-fold, 130-fold, 140-fold, 150-fold, 160-fold, 170-fold, or 180-fold as compared to the subject not administered the vaccine.

The cellular immune response induced by the vaccine can include eliciting a CD4$^+$ T cell response. The elicited CD4$^+$ T cell response can be reactive with the MERS-CoV antigen. The elicited CD4$^+$ T cell response can be polyfunctional. The induced cellular immune response can include eliciting a CD4$^+$ T cell response, in which the CD4$^+$ T cells produce IFN-$\gamma$, TNF-$\alpha$, IL-2, or a combination of IFN-$\gamma$ and TNF-$\alpha$.

The induced cellular immune response can include an increased frequency of CD3$^+$CD4$^+$ T cells that produce IFN-$\gamma$. The frequency of CD3$^+$CD4$^+$IFN-$\gamma^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold as compared to the subject not administered the vaccine.

The induced cellular immune response can include an increased frequency of CD3$^+$CD4$^+$ T cells that produce TNF-$\alpha$. The frequency of CD3$^+$CD4$^+$TNF-$\alpha^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, or 22-fold as compared to the subject not administered the vaccine.

The induced cellular immune response can include an increased frequency of CD3$^+$CD4$^+$ T cells that produce IL-2. The frequency of CD3$^+$CD4$^+$IL-2$^+$ T cells associated with the subject administered the vaccine can be increased by at least about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 26-fold, 27-fold, 28-fold, 29-fold, 30-fold, 31-fold, 32-fold, 33-fold, 34-fold, 35-fold, 36-fold, 37-fold, 38-fold, 39-fold, 40-fold, 45-fold, 50-fold, 55-fold, or 60-fold as compared to the subject not administered the vaccine.

The induced cellular immune response can include an increased frequency of CD3$^+$CD4$^+$ T cells that produce both IFN-$\gamma$ and TNF-$\alpha$. The frequency of CD3$^+$CD4$^+$IFN-$\gamma^+$TNF-$\alpha^+$ associated with the subject administered the vaccine can be increased by at least about 2-fold, 2.5-fold, 3.0-fold, 3.5-fold, 4.0-fold, 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold, 10.5-fold, 11.0-fold, 11.5-fold, 12.0-fold, 12.5-fold, 13.0-fold, 13.5-fold, 14.0-fold, 14.5-fold, 15.0-fold, 15.5-fold, 16.0-fold, 16.5-fold, 17.0-fold, 17.5-fold, 18.0-fold, 18.5-fold, 19.0-fold, 19.5-fold, 20.0-fold, 21-fold, 22-fold, 23-fold 24-fold, 25-fold, 26-fold, 27-fold, 28-fold, 29-fold, 30-fold, 31-fold, 32-fold, 33-fold, 34-fold, or 35-fold as compared to the subject not administered the vaccine.

The vaccine of the present invention can have features required of effective vaccines such as being safe so the vaccine itself does not cause illness or death; is protective against illness resulting from exposure to live pathogens such as viruses or bacteria; induces neutralizing antibody to prevent invention of cells; induces protective T cells against intracellular pathogens; and provides ease of administration, few side effects, biological stability, and low cost per dose.

The vaccine can further induce an immune response when administered to different tissues such as the muscle or skin. The vaccine can further induce an immune response when administered via electroporation, or injection, or subcutaneously, or intramuscularly.

a. Middle East Respiratory Syndrome Coronavirus (MERS-CoV) Antigen

As described above, the vaccine comprises a MERS-CoV antigen, a fragment thereof, a variant thereof, or a combination thereof. Coronaviruses, including MERS-CoV, are encapsulated by a membrane and have a type 1 membrane glycoprotein known as spike (S) protein, which forms protruding spikes on the surface of the coronavirus. The spike protein facilitates binding of the coronavirus to proteins located on the surface of a cell, for example, the metalloprotease amino peptidase N, and mediates cell-viral membrane fusion. In particular, the spike protein contains an S1 subunit that facilitates binding of the coronavirus to cell surface proteins. Accordingly, the S1 subunit of the spike protein controls which cells are infected by the coronavirus. The spike protein also contains a S2 subunit, which is a transmembrane subunit that facilitates viral and cellular membrane fusion. Accordingly, the MERS-CoV antigen can comprise a MERS-CoV spike protein, a S1 subunit of a MERS-CoV spike protein, or a S2 subunit of a MERS-CoV spike protein.

Upon binding cell surface proteins and membrane fusion, the coronavirus enters the cell and its singled-stranded RNA genome is released into the cytoplasm of the infected cell. The singled-stranded RNA genome is a positive strand and thus, can be translated into a RNA polymerase, which produces additional viral RNAs that are minus strands. Accordingly, the MERS-CoV antigen can also be a MERS-CoV RNA polymerase.

The viral minus RNA strands are transcribed into smaller, subgenomic positive RNA strands, which are used to translate other viral proteins, for example, nucleocapsid (N) protein, envelope (E) protein, and matrix (M) protein. Accordingly, the MERS-CoV antigen can comprise a MERS-CoV nucleocapsid protein, a MERS-CoV envelope protein, or a MERS-CoV matrix protein.

The viral minus RNA strands can also be used to replicate the viral genome, which is bound by nucleocapsid protein. Matrix protein, along with spike protein, is integrated into the endoplasmic reticulum of the infected cell. Together, the nucleocapsid protein bound to the viral genome and the membrane-embedded matrix and spike proteins are budded into the lumen of the endoplasmic reticulum, thereby encasing the viral genome in a membrane. The viral progeny are then transported by golgi vesicles to the cell membrane of the infected cell and released into the extracellular space by endocytosis.

In some embodiments, the MERS-CoV antigen can be a MERS-CoV spike protein, a MERS-CoV RNA polymerase, a MERS-CoV nucleocapsid protein, a MERS-CoV envelope protein, a MERS-CoV matrix protein, a fragment thereof, a variant thereof, or a combination thereof. The MERS-CoV antigen can be a consensus antigen derived from two or more MERS-CoV spike antigens, two or more MERS-CoV RNA polymerases, two or more MERS-CoV nucleocapsid proteins, two or more envelope proteins, two or more matrix proteins, or a combination thereof. The MERS-CoV consensus antigen can be modified for improved expression. Modification can include codon optimization, RNA optimization, addition of a kozak sequence for increased translation initiation, and/or the addition of an immunoglobulin leader sequence to increase the immunogenicity of the MERS-CoV antigen. In some embodiments the MERS-CoV antigen includes an IgE leader, which can be the amino acid sequence set forth in SEQ ID NO:6 and encoded by the nucleotide sequence set forth in SEQ ID NO:5.

(1) MERS-CoV Spike Antigen

The MERS-CoV antigen can be a MERS-CoV spike antigen, a fragment thereof, a variant thereof, or a combination thereof. The MERS-CoV spike antigen is capable of eliciting an immune response in a mammal against one or more MERS-CoV strains. The MERS-CoV spike antigen can comprise an epitope(s) that makes it particularly effective as an immunogen against which an anti-MERS-CoV immune response can be induced.

The MERS-CoV spike antigen can be a consensus sequence derived from two or more strains of MERS-CoV. The MERS-CoV spike antigen can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the MERS-CoV spike antigen. The MERS-CoV consensus spike antigen can comprise a signal peptide such as an immunoglobulin signal peptide, for example, but not limited to, an immunoglobulin E (IgE) or immunoglobulin (IgG) signal peptide. In some embodiments, the MERS-CoV consensus spike antigen can comprise a hemagglutinin (HA) tag. The MERS-CoV consensus spike antigen can be designed to elicit stronger and broader cellular and/or humoral immune responses than a corresponding codon optimized spike antigen.

The MERS-CoV consensus spike antigen can be the nucleic acid sequence SEQ ID NO:1, which encodes SEQ ID NO:2 (FIGS. 8A and 8B). In some embodiments, the MERS-CoV consensus spike antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence set forth in SEQ ID NO:1. In other embodiments, the MERS-CoV consensus spike antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

The MERS-CoV consensus spike antigen can be the amino acid sequence SEQ ID NO:2. In some embodiments, the MERS-CoV consensus spike antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:2.

Immunogenic fragments of SEQ ID NO:2 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of SEQ ID NO:2. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:2 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:1. Immunogenic fragments can be at least 60%, at least 65%, at least 70%, at least 75%, at least 80%, at least 85%, at least 90%, at least 95%, at least 96%, at least 97%, at least 98% or at least 99% of SEQ ID NO:1. Immunogenic fragments can be at least 95%, at least 96%, at least 97% at least 98% or at least 99% homologous to fragments of SEQ ID NO:1. In some embodiments, immunogenic fragments include sequences that encode a leader sequence, such as for example an immunoglobulin leader, such as the IgE leader. In some embodiments, fragments are free of coding sequences that encode a leader sequence.

(a) MERS-CoV Spike Antigen Lacking a Cytoplasmic Domain

The MERS-CoV antigen can be a MERS-CoV spike antigen lacking a cytoplasmic domain (i.e., also referred to herein as "MERS-CoV spike antigen ΔCD"), a fragment thereof, a variant thereof, or a combination thereof. The MERS-CoV spike antigen ΔCD is capable of eliciting an immune response in a mammal against one or more MERS-CoV strains. The MERS-CoV spike antigen ΔCD can comprise an epitope(s) that makes it particularly effective as an immunogen against which an anti-MERS-CoV immune response can be induced.

The MERS-CoV spike antigen ΔCD can be a consensus sequence derived from two or more strains of MERS-CoV. The MERS-CoV spike antigen ΔCD can comprise a consensus sequence and/or modification(s) for improved expression. Modification can include codon optimization, RNA optimization, addition of a kozak sequence for increased translation initiation, and/or the addition of an immunoglobulin leader sequence to increase the immunogenicity of the MERS-CoV spike antigen ΔCD. The MERS-CoV consensus spike antigen ΔCD can comprise a signal peptide such as an immunoglobulin signal peptide, for example, but not limited to, an immunoglobulin E (IgE) or immunoglobulin (IgG) signal peptide. In some embodiments, the consensus spike antigen ΔCD can comprise a hemagglutinin (HA) tag. The MERS-CoV consensus spike antigen ΔCD can be designed to elicit stronger and broader cellular and/or humoral immune responses than a corresponding codon optimized spike antigen ΔCD.

The MERS-CoV consensus spike antigen ΔCD can be the nucleic acid sequence SEQ ID NO:3, which encodes SEQ ID NO:4 (FIGS. 8C and 8D). In some embodiments, the MERS-CoV consensus spike antigen ΔCD can be the nucleic acid sequence having at least about 90%, 91%, 92%, 93%, 94%, 95%, 96%, 97%, 98%, 99% or 100% identity over an entire length of the nucleic acid sequence set forth in SEQ ID NO:3. In other embodiments, the MERS-CoV consensus spike antigen ΔCD can be the nucleic acid sequence that encodes the amino acid sequence having at least about 90%, 91%, 92%, 93%, 94%, 95%, 96%, 97%, 98%, 99%, or 100% identity over an entire length of the amino acid sequence set forth in SEQ ID NO:4.

The MERS-CoV consensus spike antigen ΔCD can be the amino acid sequence SEQ ID NO:4. In some embodiments, the MERS-CoV consensus spike antigen ΔCD can be the amino acid sequence having at least about 90%, 91%, 92%, 93%, 94%, 95%, 96%, 97%, 98%, 99%, or 100% identity over an entire length of the amino acid sequence set forth in SEQ ID NO:4.

Immunogenic fragments of SEQ ID NO:4 can be provided. Immunogenic fragments can comprise at least 60%, at least 65%, at least 70%, at least 75%, at least 80%, at least 85%, at least 90%, at least 95%, at least 96%, at least 97%, at least 98% or at least 99% of SEQ ID NO:4. In some embodiments, immunogenic fragments include a leader sequence, such as for example an immunoglobulin leader, such as the IgE leader. In some embodiments, immunogenic fragments are free of a leader sequence.

Immunogenic fragments of proteins with amino acid sequences homologous to immunogenic fragments of SEQ ID NO:4 can be provided. Such immunogenic fragments can comprise at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:4. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, immunogenic fragments include a leader sequence, such as for example an immunoglobulin leader, such as the IgE leader. In some embodiments, immunogenic fragments are free of a leader sequence.

Some embodiments relate to immunogenic fragments of SEQ ID NO:3. Immunogenic fragments can be at least 60%, at least 65%, at least 70%, at least 75%, at least 80%, at least 85%, at least 90%, at least 95%, at least 96%, at least 97%, at least 98% or at least 99% of SEQ ID NO:3. Immunogenic fragments can be at least 95%, at least 96%, at least 97% at least 98% or at least 99% homologous to fragments of SEQ ID NO:3. In some embodiments, immunogenic fragments include sequences that encode a leader sequence, such as for example an immunoglobulin leader, such as the IgE leader. In some embodiments, fragments are free of coding sequences that encode a leader sequence.

b. Vector

The vaccine can comprise one or more vectors that include a nucleic acid encoding the antigen. The one or more vectors can be capable of expressing the antigen. The vector can have a nucleic acid sequence containing an origin of replication. The vector can be a plasmid, bacteriophage, bacterial artificial chromosome or yeast artificial chromosome. The vector can be either a self-replicating extrachromosomal vector or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be a circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be perM2. The LEC can be perNP. perNP and perMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

c. Excipients and Other Components of the Vaccine

The vaccine may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in an alternative plasmid or are delivered as proteins in combination with the plasmid above in the vaccine. The adjuvant may be selected from the group consisting of: α-interferon(IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. METHOD OF VACCINATION

Also provided herein is a method of treating, protecting against, and/or preventing disease in a subject in need thereof by administering the vaccine to the subject. Administration of the vaccine to the subject can induce or elicit an immune response in the subject. The induced immune response can be used to treat, prevent, and/or protect against disease, for example, pathologies relating to MERS-CoV infection. The induced immune response provided the subject administered the vaccine resistance to one or more MERS-CoV strains.

The induced immune response can include an induced humoral immune response and/or an induced cellular immune response. The humoral immune response can be induced by about 1.5-fold to about 16-fold, about 2-fold to about 12-fold, or about 3-fold to about 10-fold. The induced humoral immune response can include IgG antibodies and/or neutralizing antibodies that are reactive to the antigen. The induced cellular immune response can include a $CD8^+$ T cell response, which is induced by about 2-fold to about 30-fold, about 3-fold to about 25-fold, or about 4-fold to about 20-fold.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

a. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second.

Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

4. KIT

Provided herein is a kit, which can be used for treating a subject using the method of vaccination described above. The kit can comprise the vaccine.

The kit can also comprise instructions for carrying out the vaccination method described above and/or how to use the kit. Instructions included in the kit can be affixed to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

The present invention has multiple aspects, illustrated by the following non-limiting examples.

5. EXAMPLES

Example 1

MERS-CoV Consensus Spike Antigen

Figure 3:
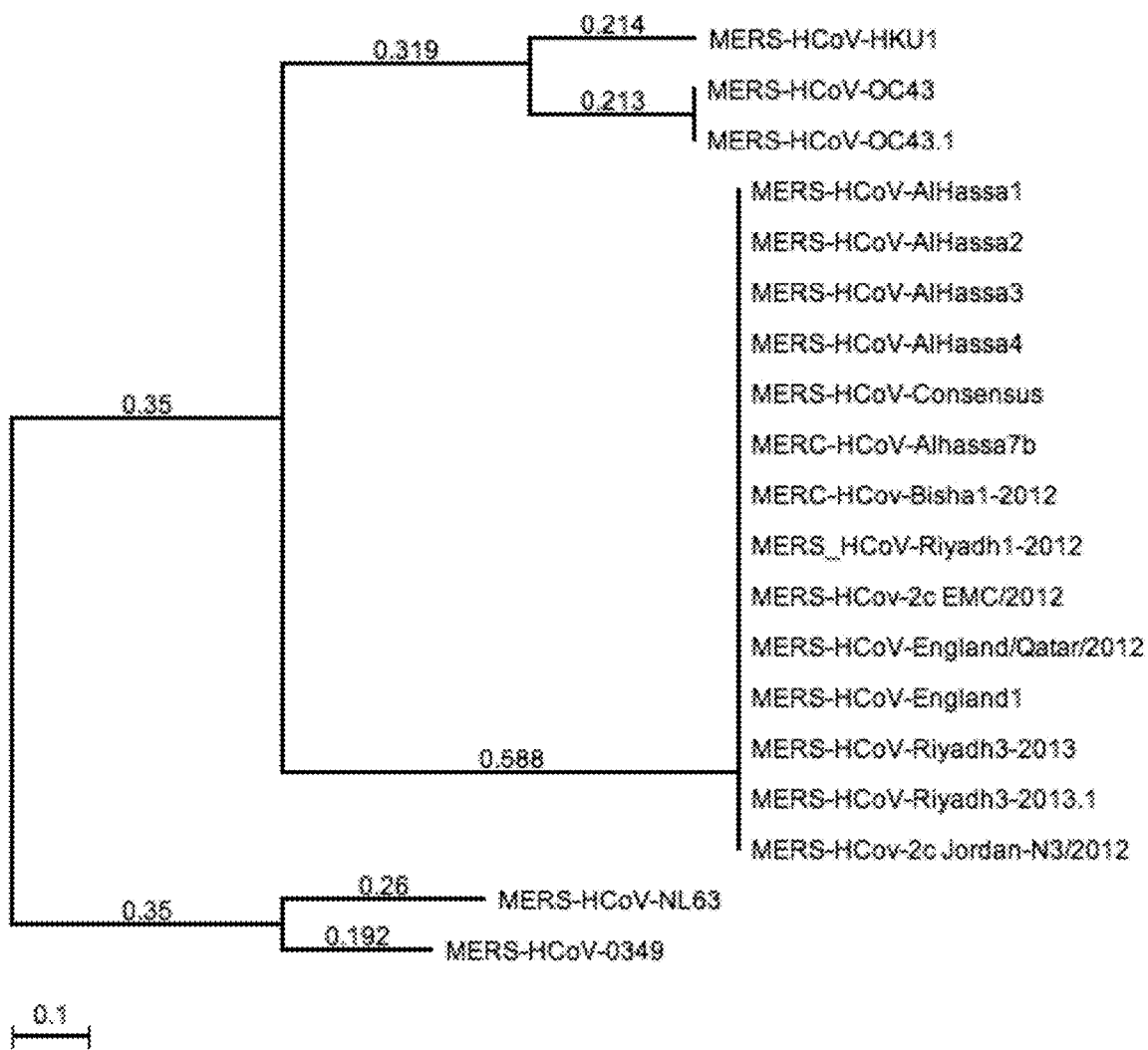
FIG. 3 shows a phylogenetic tree depicting the relationship between the indicated MERS-CoV and a MERS-CoV consensus spike antigen.

As described elsewhere herein, multiple strains of MERS-CoV exist as shown in FIG. 3 and a consensus spike antigen was created to account for variance between these multiple strains of MERS-CoV. Accordingly, the MERS-CoV consensus spike antigen was derived from the respective spike antigens of the viruses listed in FIG. 3. Phylogenetic analysis was performed based upon the spike antigen and placed the MERS-CoV consensus spike antigen relative to its component spike antigens (FIG. 3, label "MERS-HCoV-Consensus" represented the MERS-CoV consensus spike antigen). The MERS-CoV consensus spike antigen also contained an N-terminal immunoglobulin E (IgE) leader sequence. The nucleic acid and amino acid sequences comprising the MERS-CoV consensus spike antigen are shown in FIGS. 8A and 8B, respectively. In FIG. 8A, underlining indicates the nucleotides that encode the IgE leader sequence. In FIG. 8B, underlining indicates the IgE leader sequence.

Figures 4A, 4B:
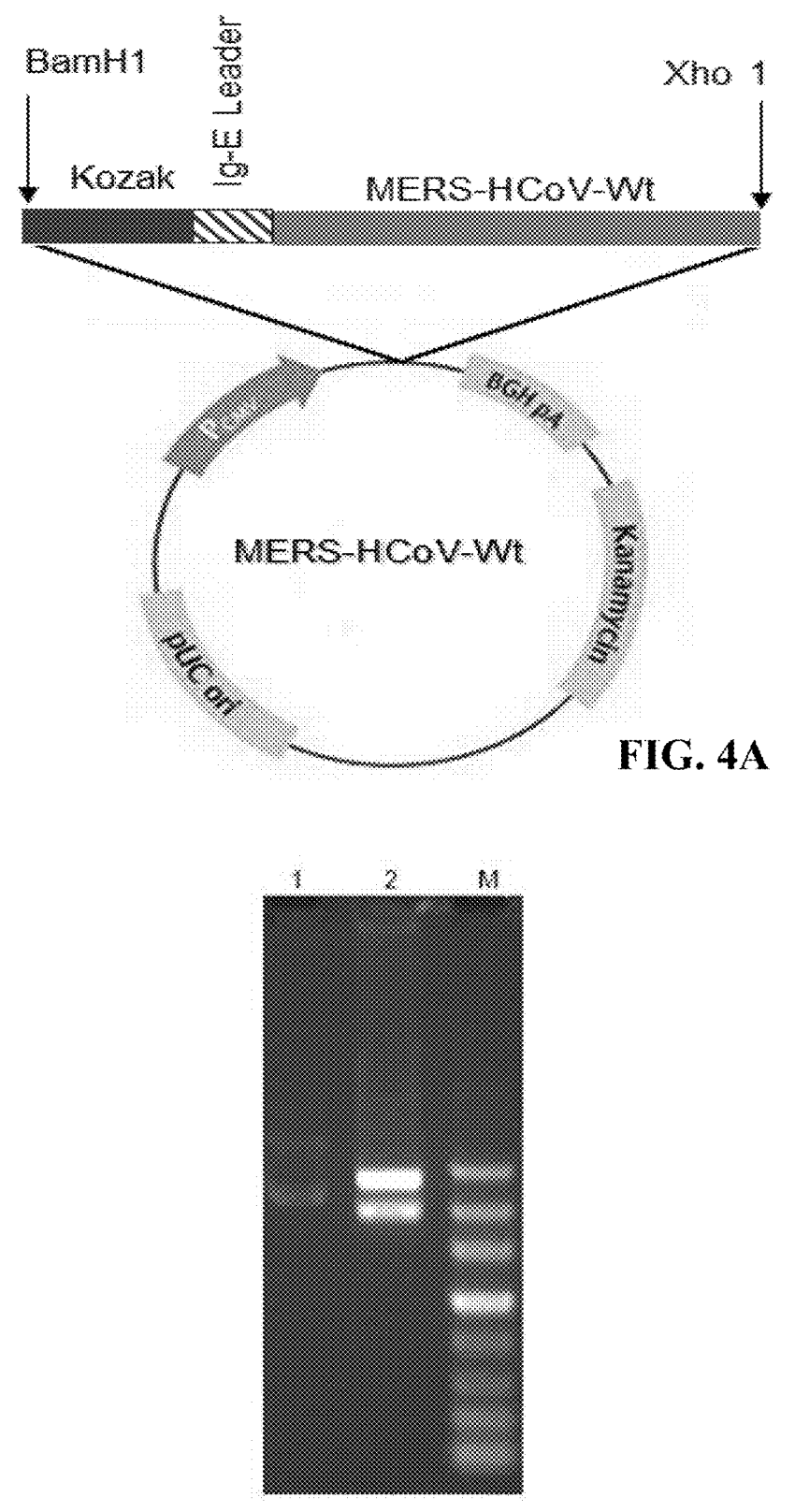

A kozak sequence was placed on the 5' end of the nucleic acid sequence encoding the MERS-CoV consensus spike antigen and the resulting nucleic acid sequence was inserted between the BamHI and XhoI sites of the pVAX1 vector (Life Technologies, Carlsbad, Calif.) (FIG. 4A, resulting construct named MERS-HCoV-WT). Correct insertion of this nucleic acid sequence into the pVAX1 vector was confirmed by BamHI and XhoI digestion, followed by gel electrophoresis (FIG. 4B). In FIG. 4B, Lane M indicated the marker, lane 1 was undigested MERS-HCoV-WT construct, and lane 2 was digested MERS-HCoV-WT construct. Digestion yielded the expected fragment sizes, indicating that the MERS-HCoV-WT construct included the pVAX1 vector and the inserted nucleic acid sequence (i.e., the nucleic acid sequence containing the kozak sequence and encoding the MERS-CoV consensus spike antigen).

Construction and characterization of this MERS-HCoV-WT construct is also described below in Examples 9 and 10.

Example 2

MERS-CoV Consensus Spike Antigen Lacking a Cytoplasmic Domain

Figure 5:
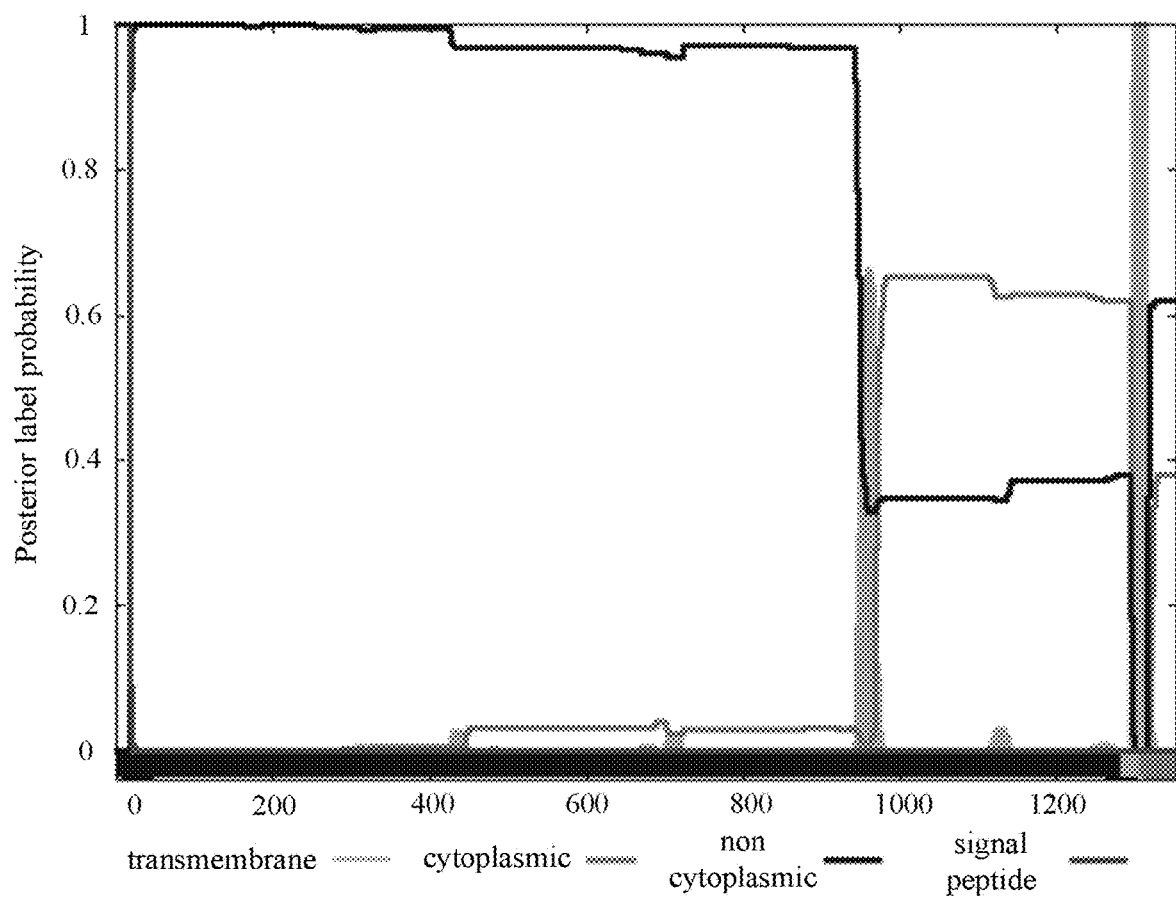
FIG. 5 shows a graph generated by the web-based software Phobius.
Figure 6:
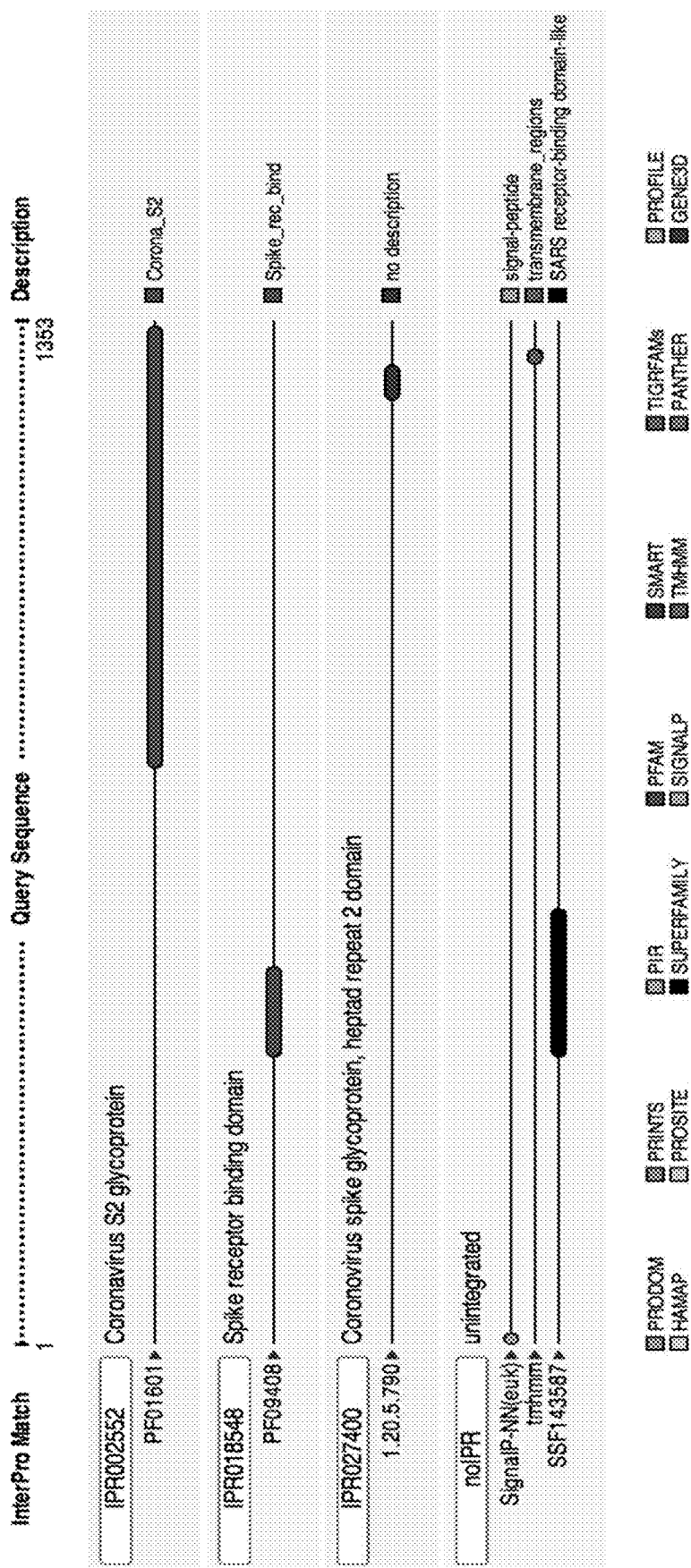
FIG. 6 shows a schematic generated by the web-based software InterProS can.

The spike antigen from coronaviruses is a type 1 membrane glycoprotein that has a transmembrane domain, which in turn, defines cytoplasmic and non-cytoplasmic domains of the spike antigen. To determine the location of the cytoplasmic domain in the MERS-CoV spike antigen, web-based software was used to predict the location of domains within various MERS-CoV spike antigens. In particular, the web-based software Phobius and InterProScan were employed in this analysis. Representative results from the Phobius and InterProScan analysis are shown in FIGS. 5 and 6, respectively.

From this domain analysis of the MERS-CoV spike antigens, a second MERS-CoV consensus spike antigen was generated, which lacked the cytoplasmic domain. In particular, the nucleic acid sequence encoding the MERS-CoV consensus spike antigen (described in Example 1, FIG. 8A, SEQ ID NO:1) was modified to insert two stop codons such that the translated protein did not contain the cytoplasmic domain (i.e., MERS-CoV consensus spike antigen ΔCD).

Figure 7A:
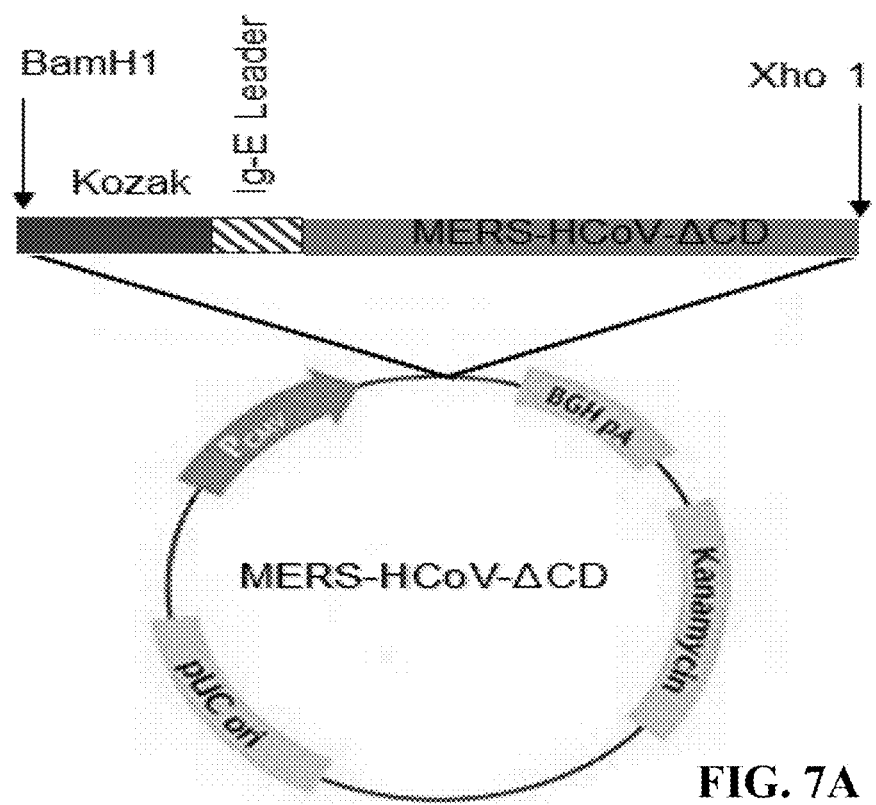
FIG. 7A shows a schematic illustrating the MERS-HCoV-ΔCD construct.

The nucleic acid and amino acid sequences of the MERS-CoV consensus spike antigen ΔCD are shown in FIGS. 8C and 8D, respectively. In FIG. 8C, underlining indicates the nucleotides that encode the IgE leader sequence and double underlining indicates the two inserted stop codons (relative to SEQ ID NO:1 that prevented translation of the cytoplasmic domain). In FIG. 8D, underlining indicates the IgE leader sequence. A schematic illustrating the resulting construct, MERS-HCoV-ΔCD, is shown in FIG. 7A.

Figure 7B:
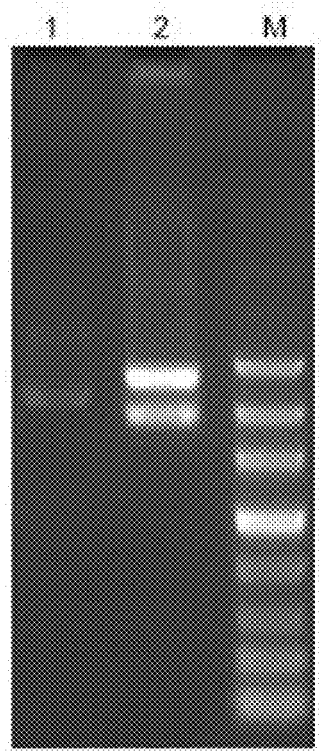
FIG. 7B shows an image of a stained gel.

The MERS-HCoV-ΔCD construct was digested with BamHI and XhoI, followed by gel electrophoresis, to confirm the insert was present in the pVAX1 vector (FIG. 7B). In FIG. 7B, Lane M indicated the marker, lane 1 was undigested MERS-HCoV-ΔCD construct, and lane 2 was digested MERS-HCoV-ΔCD construct. Digestion yielded the expected fragment sizes, indicating that the MERS-HCoV-ΔCD construct included the pVAX1 vector and the inserted nucleic acid sequence (i.e., the nucleic acid sequence containing the kozak sequence and encoding the MERS-CoV consensus spike antigen ΔCD).

Construction and characterization of this MERS-HCoV-ΔCD construct is also described below in Examples 9 and 10.

Example 3

Expression and Humoral Response

The above described MERS-HCoV-WT and MERS-HCoV-ΔCD constructs were examined to determine that the respective antigens were expressed within cells and recognizable by antibody. The MERS-HCoV-WT and MERS-HCoV-ΔCD constructs, along with pVAX1, were transfected into 293T cells. pVAX1 served as a control.

Figure 9:
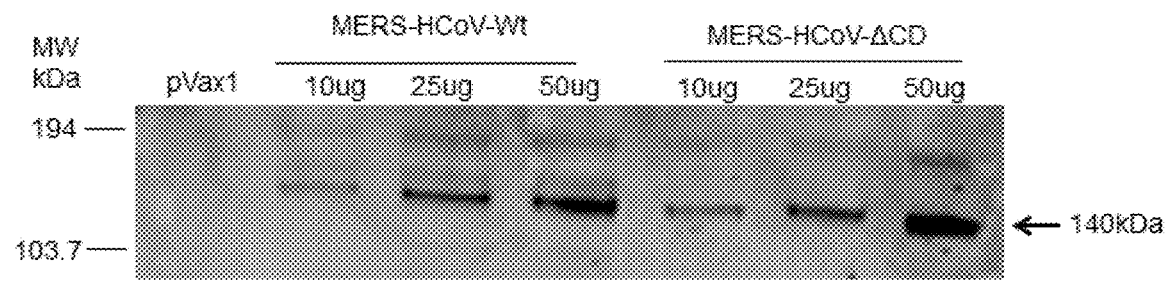
FIG. 9 shows an immunoblot.

Cell lysates were prepared two days post transfection and run on a 5-15% SDS gel. In particular, 10 μg, 25 μg, and 50 μg of cell lysate were loaded into separate wells for the cell lysates obtained from the 293T cells transfected with either the MERS-HCoV-WT or MERS-HCoV-ΔCD construct. Immunoblot analysis was then performed using sera from mice immunized with the MERS-HCoV-WT construct. No protein bands were detected in the cell lysates obtained from 293T cells transfected with pVAX1 (FIG. 9, lane labeled pVAX1). For both the MERS-HCoV-WT and MERS-HCoV-ΔCD constructs, protein bands were detected that corresponded to the predicted molecular weights of the respective antigens, thereby confirming expression of the respective antigens from the MERS-HCoV-WT and MERS-HCoV-ΔCD constructs (FIG. 9).

The immunoblot also indicated that the sera from the mice immunized with the MERS-HCoV-WT construct recognized both the MERS-CoV consensus spike antigen and the MERS-CoV consensus spike antigen ΔCD, but not other proteins in the cell lysates (as evidenced by no observed bands in the cell lysate obtained from 293T cells transfected with pVAX1). Accordingly, this sera was specific to the consensus spike antigens. The immunoblot further indicated that the MERS-HCoV-WT construct was immunogenic and produced a strong humoral response.

Example 4

Immunization Schedule for Examples 5-7

Figure 10:
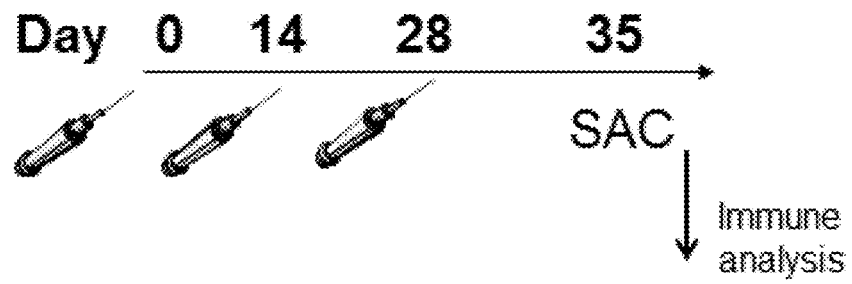
FIG. 10 shows a schematic illustrating an immunization regimen.

C57/BL6 mice were immunized with pVAX1, MERS-HCoV-WT construct, or MERS-HCoV-ΔCD following the immunization regimen illustrated in FIG. 10. On day 0, each mouse was given its respective vaccine intramuscularly (IM), followed by electroporation. In particular, each mouse was anesthetized with tribromoethanol-avertin and the hair located in the area of the tibialis anterior (TA) muscle was shaved using a small animal clipper to expose the skin. The vaccine was administered in a final volume of 30 to 50 µL via IM injection. A sterile CELLECTRA 3P ID array was then inserted through the skin into the muscle surrounding the IM injection site. The CELLECTRA 3P ID array included three 26 gauge needle-electrodes that were 3 mm in length and held together by molded plastic. The needle-electrodes were attached to the CELLECTRA electroporation device with the CELLECTRA 3P application. After insertion of the array into the muscle, a brief electric pulse was delivered and the immunized mice were placed into their respective cages and carefully observed until consciousness was regained. The above immunization procedure was repeated on day 14 and day 28. Accordingly, the immunization on day 0 was a priming immunization and the immunizations on days 14 and 28 were boost immunizations. At day 35, the mice were sacrificed and immune analysis as described below in Examples 5-7 was performed.

Example 5

IgG Antibody Response

To further examine the humoral immune response induced by the MERS-HCoV-WT and MERS-HCoV-ΔCD constructs, mice were immunized as described above in Example 4. A pre-bleed was obtained before initiation of the immunization regimen and bleeds were also obtained on day 21 and day 35 of the immunization regimen. The pre-bleed and bleeds were obtained via a retro orbital method.

The pre-bleed, day 21 bleed, and day 35 bleed from the mice immunized with the MERS-HCoV-WT construct were examined to determine the level of IgG antibodies that were immunoreactive with peptides derived from the full-length consensus spike antigen. Specifically, sera from the pre-bleed and each bleed were diluted 1:50 and added to ELISA plates that were coated with mixed peptide pools. The mixed peptide pools contained peptides derived from different portions of the full-length consensus spike antigen. Specifically, the mixed peptide pools were an equal mixture of the 6 linear peptide pools 1-6 described below in Example 6 and FIG. 15.

Figure 11A:
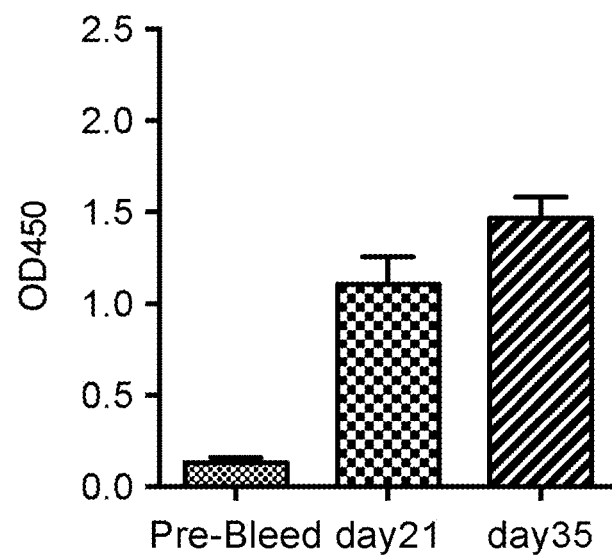
FIG. 11A and FIG. 11B show graphs plotting bleed vs. OD450.

As shown in FIG. 11A, the MERS-HCoV-WT construct elicited high levels of IgG antibody that were immunoreactive with peptides derived from the full-length consensus spike antigen. The data in FIG. 11A are from the sera of 4 mice and represented the mean±standard error of the mean (SEM). These data indicated (via comparison of the pre-bleed and bleeds) that the MERS-HCoV-WT construct induced an about 4-fold to about 6-fold increase in the level of IgG antibody that recognized the peptides derived from the full-length consensus spike antigen.

The pre-bleed, day 21 bleed, and day 35 bleed from mice immunized with the MERS-HCoV-ΔCD construct were also examined to determine the level of IgG antibodies that were immunoreactive with peptides derived from the full-length consensus spike antigen. Sera from the pre-bleed and each bleed were diluted 1:50 and added to ELISA plates that were coated with mixed peptide pools. The mixed peptide pools contained peptides derived from different portions of the full-length consensus spike antigen. Specifically, the mixed peptide pools were an equal mixture of the 6 linear peptide pools 1-6 described below in Example 6 and FIG. 15.

Figure 11B:
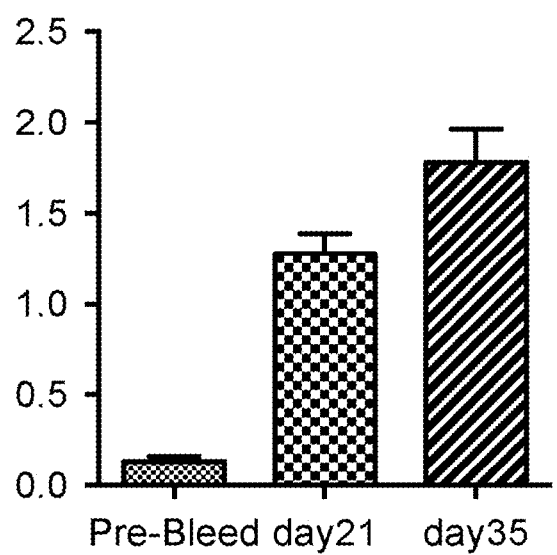

As shown in FIG. 11B, the MERS-HCoV-ΔCD construct elicited high levels of IgG antibody that were immunoreactive with the peptides derived from the full-length consensus spike antigen. The data in FIG. 11B are from the sera of 4 mice and represented mean±SEM. These data indicated (via comparison of the pre-bleed and bleeds) that the MERS-HCoV-ΔCD construct induced an about 6-fold to about 8-fold increase in the level of IgG antibody that recognized the peptides derived from the full-length consensus spike antigen.

In summary, the data in FIGS. 11A and 11B indicated that both the MERS-HCoV-WT and MERS-HCoV-ΔCD constructs elicited high levels of IgG antibodies that were immunoreactive with the peptides derived from the full-length consensus spike antigen. These data also indicated that the MERS-HCoV-ΔCD construct elicited higher levels of immunoreactive IgG antibody than the MERS-HCoV-WT construct. Accordingly, the MERS-HCoV-ΔCD construct was more immunogenic than the MERS-HCoV-WT construct as measured by IgG antibody response.

Example 6

CD8+ T Cell Response

As described above, the MERS-HCoV-WT and MERS-HCoV-ΔCD constructs each induced a significant humoral immune response directed towards the MERS-CoV spike antigen. To determine if the MERS-HCoV-WT and MERS-CoV-ΔCD constructs also induced a cellular immune response, mice were immunized as described above in Example 4. After sacrifice on day 35 of the immunization regimen, the antigen-specific response of CD8+ T cells was analyzed using an interferon-gamma (IFN-γ) ELISpot assay with a matrix of peptide pools covering the amino acid sequence of the full-length consensus MERS-CoV spike antigen. The matrix of peptide pools is shown in FIG. 12 and also facilitated identification of the dominant epitope(s) recognized by the CD8+ T cell response that was induced by the MERS-HCoV-WT and MERS-HCoV-ΔCD constructs. This matrix of peptide pools was derived from a peptide scan over the entire length of the MERS-HCoV-WT spike antigen and the peptides were 15-mers with 11 amino acid overlap.

Figure 13:
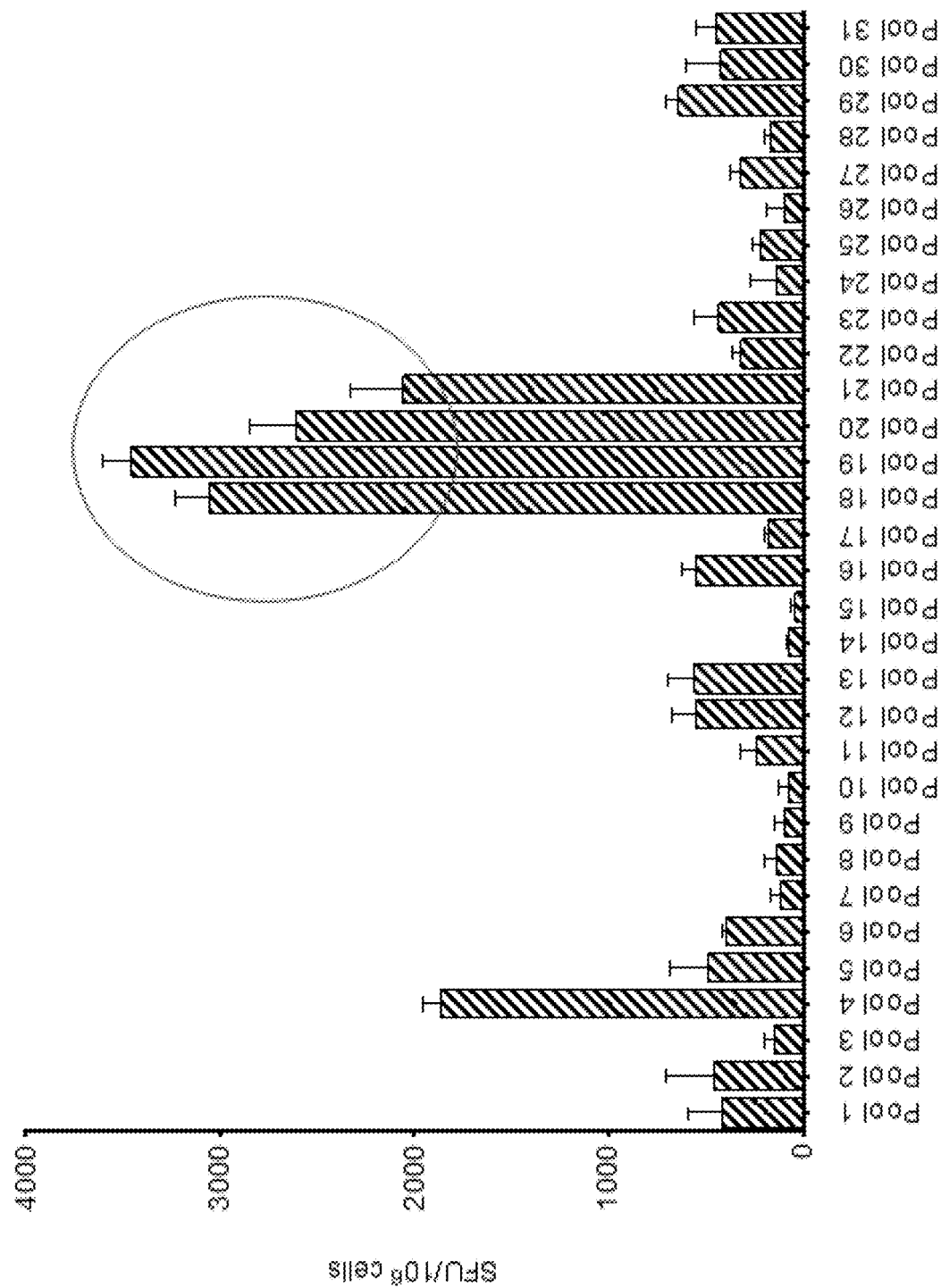
FIG. 13 shows a graph plotting peptide pool vs. spot forming unit per $10^6$ cells (SFU/$10^6$ cells).
Figure 14:
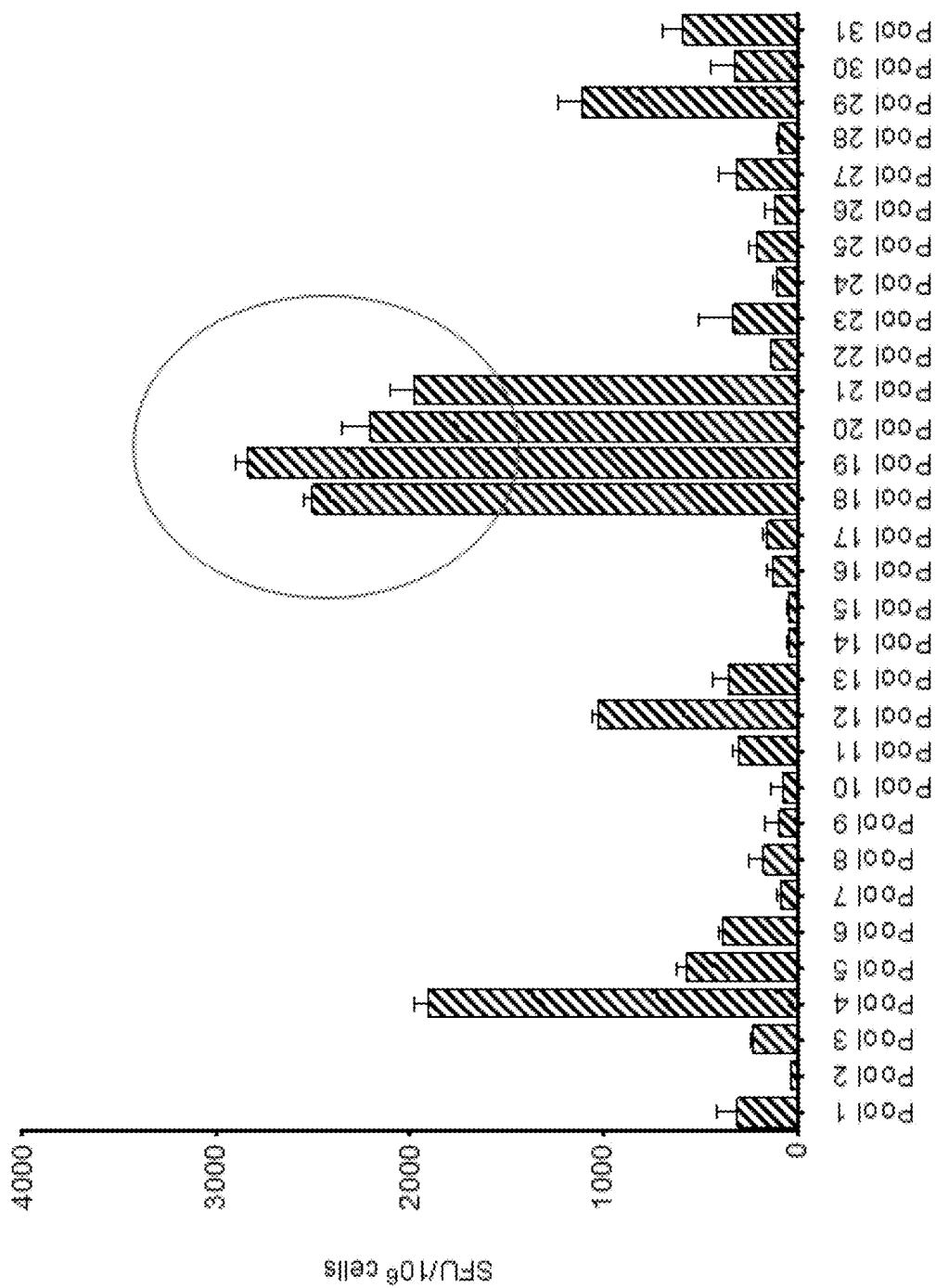
FIG. 14 shows a graph plotting peptide pool vs. spot forming unit per $10^6$ cells (SFU/$10^6$ cells).

The results of the IFN-γ ELISpot assay with this matrix of peptide pools are shown in FIGS. 13 and 14 for the MERS-HCoV-WT and MERS-HCoV-ΔCD constructs, respectively. In both FIGS. 13 and 14, the data represented mean±SEM. Both constructs induced a significant CD8+ T cell response, in which the dominant epitope resided in pools 18, 19, 20, and 21 (FIGS. 13 and 14, circled bars). Another epitope resided in pool 4. Accordingly, these data indicated that the MERS-HCoV-WT and MERS-HCoV-ΔCD constructs induced a strong cellular immune response that was reactive to a subset of spike antigen peptides.

To further examine the CD8+ T cell response, mice were immunized with 25 μg of pVAX1, MERS-HCoV-WT construct, or MERS-HCoV-ΔCD construct following the immunization regimen described in Example 4 above. Immunization with pVAX1 served as a control. After sacrifice on day 35 of the immunization regimen, the antigen-specific response of CD8+ T cells isolated from three groups of mice was examined using the IFN-γ ELISpot assay. In particular, the CD8+ T cells were stimulated with 6 different peptide pools. These peptide pools 1-6 covered the peptides shown in the matrix of FIG. 12.

Figure 15:
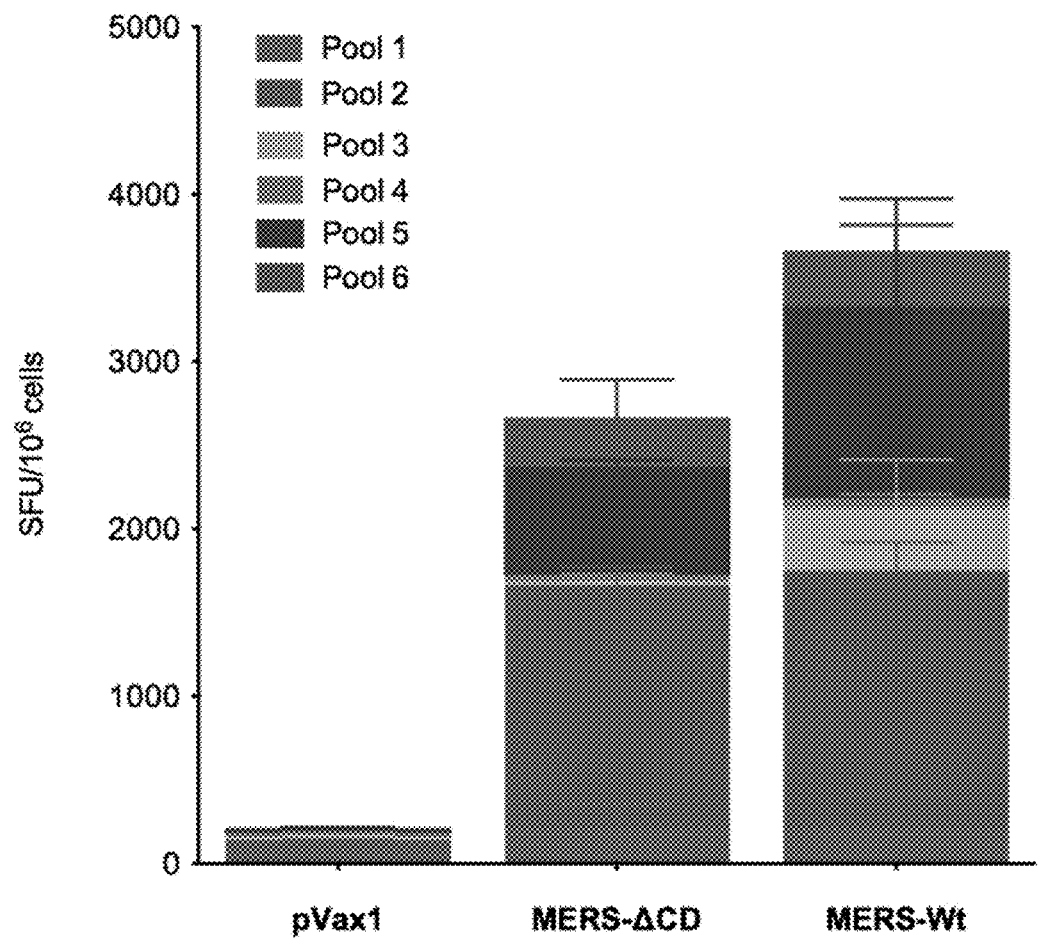

As shown in FIG. 15, the magnitude of the cellular immune response induced by the MERS-HCoV-WT and MERS-HCoV-ΔCD constructs varied depending on the peptide pool used to stimulate the CD8+ T cells isolated from the respective mice. For both the MERS-HCoV-WT and MERS-HCoV-ΔCD constructs, peptide pool 1 elicited a CD8+ T cell response similar to the control pVAX1, thereby indicating that peptide pool 1 did not contain an epitope that stimulated the CD8+ T cells. Peptide pools 1-6 elicited similar responses from the CD8+ T cells isolated from mice immunized with pVAX1.

Peptide pools 2, 3, and 4 elicited comparable responses from the CD8+ T cells isolated from mice vaccinated with MERS-HCoV-WT or MERS-HCoV-ΔCD construct. Additionally, the CD8+ T cell response to peptide pools 2, 3, and 4 was significantly higher when the mice were immunized with either the MERS-HCoV-WT or MERS-HCoV-ΔCD construct as compared to the pVAX1 control (FIG. 15). In particular, the CD8+ T cell response to peptide pools 2, 3, and 4 was about 7-fold higher when the mice were immunized with the MERS-HCoV-ΔCD construct as compared to the control pVAX1. The CD8+ T cell response to peptide pools 2, 3, and 4 was about 7.5-fold, about 9-fold, and about 10-fold higher, respectively, when the mice were immunized with the MERS-HCoV-WT construct as compared to the control pVAX1. Accordingly, these data indicated that the MERS-HCoV-WT and MERS-HCoV-ΔCD constructs, unlike the control pVAX1, induced a significant CD8+ T cell response to peptides contained within peptide pools 2, 3, and 4.

Peptide pools 5 and 6 elicited a greater response from the CD8+ T cells isolated from mice immunized with the MERS-HCoV-WT or MERS-HCoV-ΔCD construct as compared to peptide pools 1, 2, 3, and 4 (FIG. 15). Additionally, the CD8+ T cell response to peptide pools 5 and 6 was significantly higher when the mice were immunized with either the MERS-HCoV-WT or MERS-HCoV-ΔCD construct as compared to the control pVAX1. In particular, the CD8+ T cell response to peptide pools 5 and 6 was about 9-fold and about 11-fold higher, respectively, when the mice were immunized with the MERS-HCoV-ΔCD construct as compared to the control pVAX1. The CD8+ T cell response to peptide pools 5 and 6 was about 13-fold and about 15-fold higher, respectively, when the mice were immunized with the MERS-HCoV-WT as compared to the control pVAX1. Accordingly, these data indicated that the MERS-HCoV-WT and MERS-HCoV-ΔCD constructs, unlike the control pVAX1, induced a significant CD8+ T cell response to peptides contained within peptide pools 5 and 6.

In summary, the above data indicated that immunization with the MERS-HCoV-WT and MERS-HCoV-ΔCD constructs induced a significant cellular immune response that was specific and reactive to a subset of spike antigen peptides.

Example 7

Polyfunctional Cellular Immune Response

As described above, the MERS-HCoV-WT and MERS-HCoV-ΔCD constructs induced a CD8+ T cell response that was reactive and specific to the MERS-CoV spike antigen. To further examine the cellular immune response induced by the MERS-HCoV-WT and MERS-HCoV-ΔCD constructs, the functionality of the T cells after immunization was examined. In particular, mice were immunized with pVAX1, MERS-HCoV-WT construct, or MERS-HCoV-ΔCD construct following the immunization regimen described above in Example 4. At day 35 of the immunization regimen, splenocytes were isolated from the sacrificed mice. The isolated splenocytes were stimulated in vitro with a peptide pool containing peptides derived from the full-length consensus MERS-CoV spike antigen. The peptide pool and the splenocytes were incubated together for 5 hours. Cells were then stained for intracellular production of IFN-γ, tumor necrosis factor alpha (TNF-α), and interleukin-2 (IL-2) and sorted by fluoresecence-activated cell sorting (FACS).

FIGS. 16A, 16B, 16C, and 16D show the measured frequency of CD3+CD4+ T cells producing IFN-γ, TNF-α, IL-2, or both IFN-γ and TNF-α, respectively, in the stimulated splenocyte populations. The data in FIGS. 16A-16D represented, for each group, splenocytes isolated from 3 mice. The data in FIGS. 16A-16D also represented mean±SEM. The frequency of CD3+CD4+ T cells producing IFN-γ, TNF-α, IL-2, or both IFN-γ and TNF-α was significantly increased in the MERS-HCoV-WT and MERS-HCoV-ΔCD groups as compared to the control pVAX1 group.

Figure 16A:
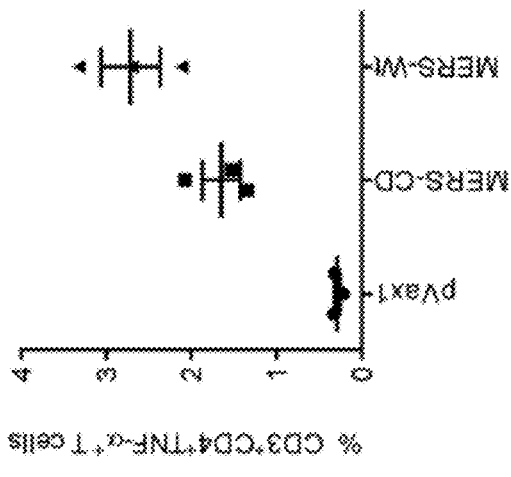
FIG. 16A shows a graph plotting immunization group vs. percent $CD3^+CD4^+IFN\text{-}\gamma^+$ T cells.
Figure 16B:
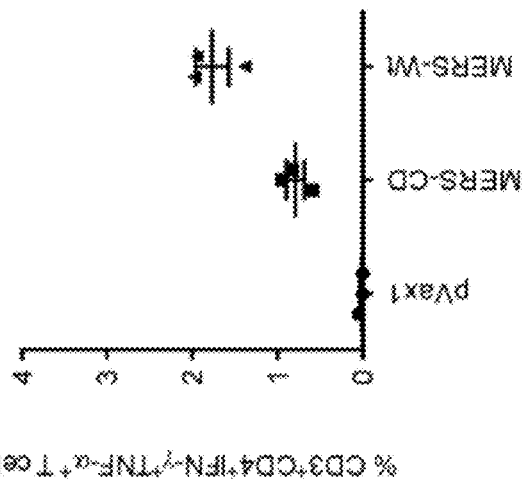
FIG. 16B shows a graph plotting immunization group vs. percent $CD3^+CD4^+TNF\text{-}\alpha^+$ T cells.
Figure 16C:
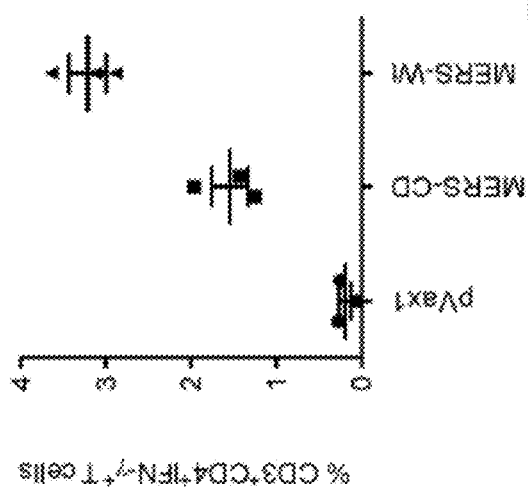
FIG. 16C shows a graph plotting immunization group vs. percent $CD3^+CD4^+IL\text{-}2^+$ T cells.
Figure 16D:
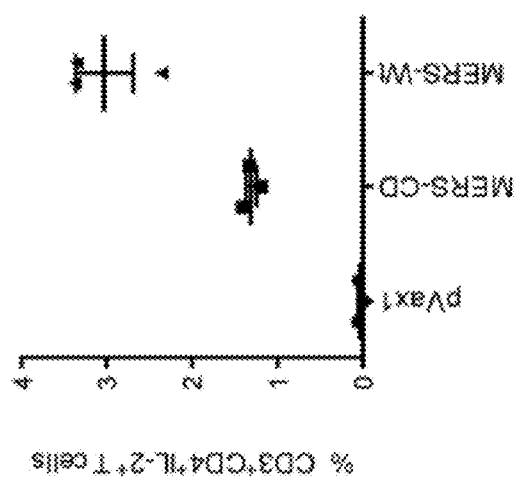
FIG. 16D shows a graph plotting immunization group vs. percent $CD3^+CD4^+IFN\text{-}\gamma^+TNF\text{-}\alpha^+$ T cells.

In particular, the frequency of CD3+CD4+IFN-γ+ T cells was about 6-fold and about 13-fold greater in the splenoctye populations isolated from mice immunized with the MERS-HCoV-ΔCD and MERS-HCoV-WT constructs, respectively, as compared to the control pVAX1 (FIG. 16A). The frequency of CD3+CD4+TNF-α+ T cells was about 6-fold and about 11-fold greater in the splenocyte populations isolated from mice immunized with the MERS-HCoV-ΔCD and MERS-HCoV-WT constructs, respectively, as compared to the control pVAX1 (FIG. 16B). The frequency of CD3+CD4+IL-2+ T cells was about 12.5-fold and about 30-fold greater in the splenocyte populations isolated from mice immunized with the MERS-HCoV-ΔCD and MERS-HCoV-WT constructs, respectively, as compared to the control pVAX1 (FIG. 16C). The frequency of CD3+CD4+IFN-γ+TNF-α+ T cells was about 7.5-fold and about 17.5-fold greater in the splenocyte populations isolated from mice immunized with the MERS-HCoV-ΔCD and MERS-HCoV-WT constructs, respectively, as compared to the control pVAX1 (FIG. 16D). Accordingly, these data indicated that the MERS-HCoV-WT and MERS-HCoV-ΔCD constructs, unlike the control pVAX1, induced a polyfunctional T cell response, in which increased numbers of CD3+CD4+ T cells produced IFN-γ, TNF-α, IL-2, or both IFN-γ and TNF-α.

FIGS. 17A, 17B, 17C, and 17D show the measured frequency of CD3$^+$CD8$^+$ T cells producing IFN-$\gamma$, TNF-$\alpha$, IL-2, or both IFN-$\gamma$ and TNF-$\alpha$, respectively, in the stimulated splenocyte populations. The data in FIGS. 17A-17D represented, for each group, splenocytes isolated from 4 mice. The data in FIGS. 17A-17D also represented mean±SEM. The frequency of CD3$^+$CD8$^+$ T cells producing IFN-$\gamma$, TNF-$\alpha$, IL-2, or both IFN-$\gamma$ and TNF-$\alpha$ was significantly increased in the MERS-HCoV-WT and MERS-HCoV-$\Delta$CD groups as compared to the control pVAX1.

Figure 17A:
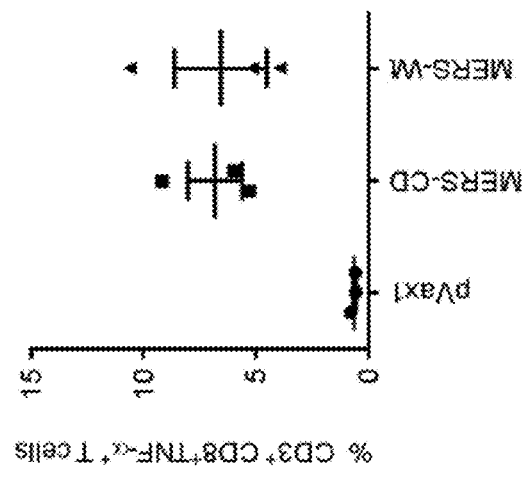
FIG. 17A shows a graph plotting immunization group vs. percent $CD3^+CD8^+IFN\text{-}\gamma^+$ T cells.
Figure 17B:
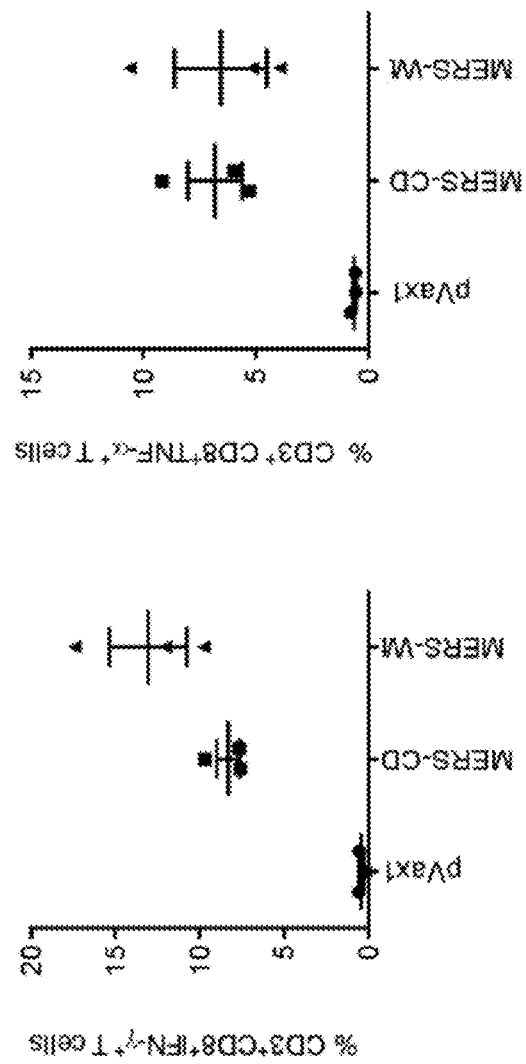
FIG. 17B shows a graph plotting immunization group vs. percent $CD3^+CD8^+TNF\text{-}\alpha^+$ T cells.
Figure 17C:
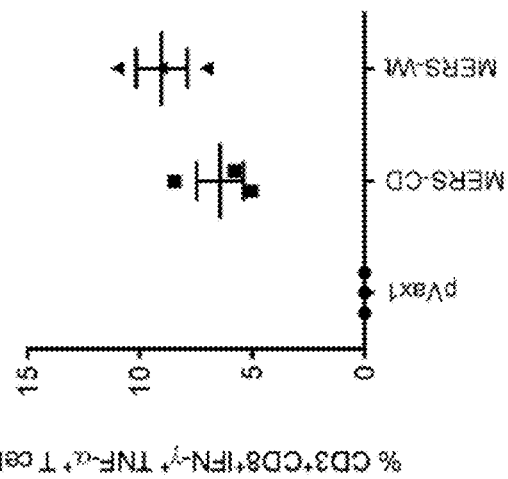
FIG. 17C shows a graph plotting immunization group vs. percent $CD3^+CD8^+IL\text{-}2^+$ T cells.
Figure 17D:
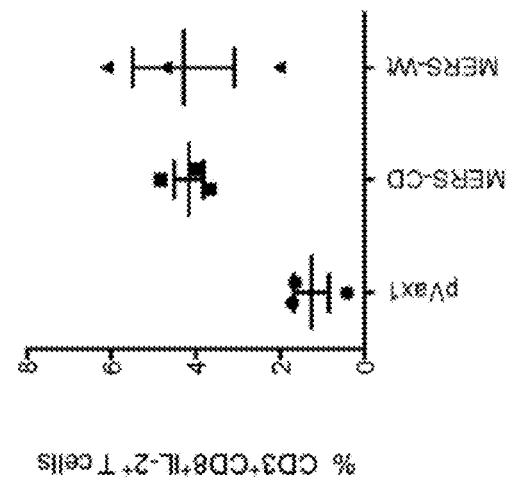
FIG. 17D shows a graph plotting immunization group vs. percent $CD3^+CD8^+IFN\text{-}\gamma^+TNF\text{-}\alpha^+$ T cells.

In particular, the frequency of CD3$^+$CD8$^+$IFN-$\gamma^+$ T cells was about 8-fold and about 13-fold greater in the splenoctye populations isolated from mice immunized with the MERS-HCoV-$\Delta$CD and MERS-HCoV-WT constructs, respectively, as compared to the control pVAX1 (FIG. 17A). The frequency of CD3$^+$CD8$^+$TNF-$\alpha^+$ T cells was about 7-fold greater in the splenocyte populations isolated from mice immunized with the MERS-HCoV-$\Delta$CD or MERS-HCoV-WT construct as compared to the control pVAX1 (FIG. 17B). The frequency of CD3$^+$CD8$^+$IL-2$^+$ T cells was about 2.5-fold greater in the splenocyte populations isolated from mice immunized with the MERS-HCoV-$\Delta$CD or MERS-HCoV-WT construct as compared to the control pVAX1 (FIG. 17C). The frequency of CD3$^+$CD8$^+$IFN-$\gamma^+$TNF-$\alpha^+$ T cells was about 50-fold and about 90-fold greater in the splenocyte populations isolated from mice immunized with the MERS-HCoV-$\Delta$CD and MERS-HCoV-WT constructs, respectively, as compared to the control pVAX1 (FIG. 17D). Accordingly, these data indicated that the MERS-HCoV-WT and MERS-HCoV-$\Delta$CD constructs, unlike the control pVAX1, induced a polyfunctional T cell response, in which increased numbers of CD3$^+$CD8$^+$ T cells produced IFN-$\gamma$, TNF-$\alpha$, IL-2, or both IFN-$\gamma$ and TNF-$\alpha$.

In summary, the above data indicated that the MERS-HCoV-WT and MERS-HCoV-$\Delta$CD constructs significantly induced polyfunctional CD3$^+$CD4$^+$ and CD3$^+$CD8$^+$ T cells that produced IFN-$\gamma$, TNF-$\alpha$, IL-2, or both IFN-$\gamma$ and TNF-$\alpha$. The MERS-HCoV-WT and MERS-HCoV-$\Delta$CD constructs supported greater polyfunctionality of both CD3$^+$CD4$^+$ and CD3$^+$CD8$^+$ T cells than the control pVAX1. Accordingly, the consensus constructs were capable of eliciting a polyfunctional cellular immune response that was reactive to the MERS-CoV spike antigen.

Example 8

Neutralizing Antibodies

As described above in Example 5, the MERS-HCoV-WT and MERS-HCoV-$\Delta$CD constructs induced a humoral immune response. To further examine the induced humoral immune response, the level of neutralizing antibodies associated with mice immunized with pVAX1, MERS-HCoV-WT construct, or MERS-HCoV-$\Delta$CD construct was examined. Specifically, sera were diluted in minimal essential medium and incubated with 50 µl of DMEM containing 100 infectious HCoV-EMC/2012 (Human Coronavirus Erasmus Medical Center/2012) particles per well at 37° C. After 90 minutes, the virus-serum mixture was added to a monolayer of Vero cells (100,000 cells per well) in a 96-well flat bottom plate and incubated for 5 days at 37° C. in a 5% CO$_2$ incubator. The titer of neutralizing antibody for each sample was reported as the highest dilution with which less than 50% of the cells showed CPE. Values were reported as reciprocal dilutions. All the samples were run in duplicate so that the final result was taken as the average of the two samples.

The results are shown below in Table 1. Immunization with the MERS-HCoV-WT and MERS-HCoV-$\Delta$CD constructs, unlike the control pVAX1, induced significant levels of neutralizing antibodies that were reactive to the MERS-CoV spike antigen.

TABLE 1

Titer of Neutralizing Antibodies.

| Mouse Number | Replicate 1 | Replicate 2 | Average Reciprocal Dilutions |
|---|---|---|---|
| MERS-HCoV-WT Mouse 1 | 320 | 320 | 320 |
| MERS-HCoV-WT Mouse 2 | 2560 | 2560 | 2560 |
| MERS-HCoV-WT Mouse 3 | 320 | 640 | 480 |
| MERS-HCoV-WT Mouse 4 | 480 | 480 | 480 |
| MERS-HCoV-WT Mouse 5 | 1610 | 1610 | 1610 |
| MERS-HCoV-WT Mouse 6 | 1280 | 640 | 960 |
| MERS-HCoV-WT Mouse 7 | 320 | 160 | 240 |
| MERS-HCoV-WT Mouse 8 | 640 | 320 | 480 |
| MERS-HCoV-WT Mouse 9 | 320 | 640 | 480 |
| MERS-HCoV-$\Delta$CD Mouse 1 | 320 | 160 | 240 |
| MERS-HCoV-$\Delta$CD Mouse 2 | 160 | 80 | 120 |
| MERS-HCoV-$\Delta$CD Mouse 3 | 320 | 320 | 320 |
| MERS-HCoV-$\Delta$CD Mouse 4 | 640 | 320 | 480 |
| MERS-HCoV-$\Delta$CD Mouse 5 | 640 | 320 | 480 |
| MERS-HCoV-$\Delta$CD Mouse 6 | 640 | 640 | 640 |
| MERS-HCoV-$\Delta$CD Mouse 7 | 320 | 160 | 240 |
| MERS-HCoV-$\Delta$CD Mouse 8 | 160 | 160 | 160 |
| MERS-HCoV-$\Delta$CD Mouse 9 | 1280 | 640 | 960 |
| MERS-HCoV-$\Delta$CD Mouse 10 | 320 | 320 | 320 |
| pVAX1 Mouse 1 | CPE in all wells | | 0 |
| pVAX1 Mouse 2 | CPE in all wells | | 0 |
| pVAX1 Mouse 3 | CPE in all wells | | 0 |
| pVAX1 Mouse 4 | CPE in all wells | | 0 |
| pVAX1 Mouse 5 | CPE in all wells | | 0 |
| pVAX1 Mouse 6 | CPE in all wells | | 0 |
| pVAX1 Mouse 7 | CPE in all wells | | 0 |
| pVAX1 Mouse 8 | CPE in all wells | | 0 |
| pVAX1 Mouse 9 | CPE in all wells | | 0 |
| pVAX1 Mouse 10 | CPE in all wells | | 0 |

In summary, the data provided in the Examples herein demonstrated that the MERS-HCoV-WT and MERS-CoV-$\Delta$CD constructs were effective vaccines that significantly induced both humoral and cellular immune responses that were reactive to the MERS-CoV spike antigen. The induced humoral immune response included increased titers of IgG antibodies and neutralizing antibodies that were immunoreactive with the MERS-CoV spike antigen as compared to a construct lacking either consensus antigen (i.e., pVAX1). The induced cellular immune response included increased CD3$^+$CD4$^+$ and CD3$^+$CD8$^+$ T cell responses that produced IFN-$\gamma$, TNF-$\alpha$, IL-2, or both IFN-$\gamma$ and TNF-$\alpha$ as compared to the construct lacking either consensus antigen (i.e., pVAX1).

Example 9

Materials and Methods for Examples 10-19

Cell Culture, Plasmids, and Expression of MERS-HCoV-Spike Protein.

HEK293T cells (ATCC#: CRL-N268) and Vero-E6 cells (ATCC#: CRL-1586) were grown in DMEM with 10% FBS (DMEM). The MERS-HCoV-Spike WT and Spike$\Delta$CD plasmid DNA constructs encoded an optimized consensus sequence of the MERS Spike protein (S). In addition, the Ig heavy chain epsilon-1 signal peptide was fused to the N-terminus of each sequence, replacing the N-terminal methionine, which facilitated expression. Each gene was genetically optimized for expression in mice, including codon- and RNA-optimization. The optimized genes were then sub-cloned into modified pVax1 mammalian expression vectors under the control of the cytomegalovirus immediate-early (CMV) promoter (GenScript). Construction of these MERS-HCoV-Spike WT and SpikeΔCD plasmid DNA constructs is also described above in Examples 1 and 2.

For in vitro expression studies, transfection was carried out using TurboFectin 8.0 reagent, following the manufacturer's protocols (OriGene). Briefly, cells were grown to 80% confluence in a 35-mm dish and transfected with 3 μg of Spike plasmid. The cells were harvested 48 hours (h) post transfection, washed twice with phosphate-buffered saline (PBS), and then suspended in cell lysis buffer (Cell Signaling Technology) to verify the expression of Spike protein by Western blotting analysis.

Mice and Immunization.

Female C57BL-6 mice (6-8 weeks old; Jackson Laboratories) were used in these experiments and divided into three experimental groups. All animals were housed in a temperature-controlled, light-cycled facility in accordance with the guidelines of the National Institutes of Health (Bethesda) and the University of Pennsylvania (Philadelphia, Pa., USA) Institutional Animal Care and Use Committee (IACUC). All immunizations were delivered into the tibialis anterior (25 μg) in a total volume of 25 μl by in vivo minimally invasive EP delivery technologies (MID-EP).

Single-cell suspensions of spleens were prepared from the immunized mice. Briefly, spleens from freshly euthanized mice were collected individually in 10 ml of RPMI 1640 supplemented with 10% FBS (R10), then processed via a paddle blender (STOMACHER 80 paddle blender; A. J. Seward and Co. Ltd., London, England) for 60 seconds on high speed. Processed spleen samples were filtered through 45 μm nylon filters then centrifuged at 800×g for 10 minutes at room temperature. Cell pellets were resuspended in 5 ml ACK lysis buffer (Life Technology) for 5 minutes at room temperature, and PBS was then added to stop the reaction. Samples were again centrifuged at 800×g for 10 minutes at room temperature. Cell pellets were suspended in R10 at a concentration of $1\times10^7$ cells/ml then passed through a 45 μm nylon filter before use in enzyme-linked immunosorbent spot (ELISpot) assay and flow cytometric analysis.

ELISpot Analysis.

Antigen specific T cell responses were determined using IFN-γ ELISpot. Briefly, PVDF 96-well plates (Millipore) were coated with purified anti-mouse IFN-γ capture antibody and incubated for 24 h at 4° C. (R&D Systems). The following day, plates were washed and blocked for 2 h with 1% BSA and 5% Sucrose. Two hundred thousand splenocytes from the immunized mice were added to each well and stimulated overnight at 37° C. in 5% $CO_2$ in the presence of RPMI 1640 (negative control), Con A (5 ug/mL; positive control), or specific peptide antigens (Ag) (10 μg/ml; GenScript). Peptide pools consisted of 15-mer peptides overlapping by 11 amino acids (GenScript). After 24 h of stimulation, the cells were washed and incubated for 24 h at 4° C. with biotinylated anti-mouse IFN-γ Abs (R&D Systems). The plates were washed, and streptavidin-alkaline phosphatase (R&D Systems) was added to each well and incubated for 2 h at room temperature. The plates were washed, and 5-bromo-4-chloro-3'-indolylphosphate p-toluidine salt and nitro blue tetrazolium chloride (Chromogen color reagent; R&D Systems) were added to each well. The plates were then rinsed with distilled water and dried at room temperature overnight. Spots were counted by an automated ELISpot reader (CTL Limited).

Flow Cytometry and Intracellular Cytokine Staining (ICCS) Assay.

Splenocytes were added to a 96-well plate ($1\times10^6$/well) and were stimulated with pooled MERS antigen peptide for 5-6 h at 37 C/5% $CO_2$ in the presence of Protein Transport Inhibitor Cocktail (Brefeldin A and Monensin; eBioscience) according to the manufacturer's instructions. The Cell Stimulation Cocktail (plus protein transport inhibitors) (phorbol 12-myristate 13-acetate (PMA), ionomycin, brefeldin A and monensin; eBioscience) was used as a positive control and R10 media as negative control. All cells were then stained for surface and intracellular proteins as described by the manufacturer's instructions (BD). Briefly, the cells were washed in FACS buffer (PBS containing 0.1% sodium azide and 1% FCS) before surface staining with flourochrome-conjugated antibodies. Cells were washed with FACS buffer, fixed and permeabilized using the BD Cytofix/Ctyoperm™ (BD) according to the manufacturer's protocol followed by intracellular staining. The following antibodies were used for surface staining: LIVE/DEAD Fixable Violet Dead Cell stain kit (Invitrogen), CD19 (V450; clone 1D3; BD Biosciences) CD4 (FITC; clone RM4-5; ebioscience), CD8 (APC-Cy7; clone 53-6.7; BD Biosciences); CD44 (A700; clone IM7; Biolegend). For intracellular staining, the following antibodies were used: IFN-γ (APC; clone XMG1.2; Biolegend), TNF-α (PE; clone MP6-XT22; ebioscience), CD3 (PerCP/Cy5.5; clone 145-2C11; Biolegend); IL-2 (PeCy7; clone JES6-SH4; ebioscience). All data was collected using a LSRII flow cytometer (BD Biosciences) and analyzed using FlowJo software (Tree Star) and SPICE v5. Boolean gating was performed using FlowJo software to examine the polyfunctionality of the T cells from vaccinated animals.

Immungoen-Specific ELISA.

An enzyme-linked immunosorbent assay (ELISA) was used to determine the titers of mouse sera. Briefly, 5 μg/ml of purified recombinant human betacoronavirus-Spike protein 2c EMC/2012 (clade A) (Sino Biological Inc.) was used to coat 96-well microtiter plates (Nalgene Nunc International, Naperville, Ill.) at 4° C. overnight. After blocking with 10% FBS in PBS, plates were washed 4 times with 0.05% PBST (Tween20 in PBS). Serum samples from immunized mice were serially diluted in 1% FBS, 0.2% PBST, added to the plates, and then incubated for 1 h at room temperature. Plates were again washed 4 times in 0.05% PBST, and then incubated with HRP-conjugated anti-mouse IgG diluted according to the manufacturer's instructions (Sigma Aldrich) for 1 h at room temperature. Bound enzyme was detected by adding OPD (o-Phenylenediamine dihydrochloride) tablets according to the manufacturer's instructions (SIGMAFAST; Sigma Aldrich). The reaction was stopped after 15 minutes with the addition of 2N $H_2SO_4$. Plates were then read at an optical density of 450 nm on a 96 Microplate Luminometer (GLOMAX; Promega). All samples were plated in duplicate. End-point-titers were determined as the highest dilution with an absorbance value greater than the mean absorbance value from at least three normal sera plus three standard deviations.

Indirect Immunofluorescent Assay (IFA).

For cells transfected with MERS-HCoV-Spike plasmid, slides were fixed with ice-cold acetone for 5 min. Nonspecific binding was then blocked with 5% skim milk in PBS at 37° C. for 30 min. The slides were then washed in PBS for 5 min and subsequently incubated with sera from immunized mice at 1:100 dilutions. Following a 1 h incubation, slides were washed as described above and incubated with Alexa Fluor 488 goat anti-mouse IgG (Invitrogen) diluted in PBS containing 1 ug/mL and 4 6-diamidino-2-phenylindole (DAPI) at 37° C. for 30 min. After washing out the unbound antibodies, the coverslips were mounted with Prolong Gold antifade reagent (Invitrogen), and the slides were observed under a confocal microscope (LSM710; Carl Zeiss). The resulting images were analyzed using the Zen software (Carl Zeiss).

Preparation of MERS-HCoV-Spike Pseudo Viral Particles.

The codon-optimized consensus MERS-HCoV Spike gene was synthesized and sub-cloned into the pVax1 vector. MERS-HCoV-Spike pseudovirus were prepared. Specifically, $2\times10^6$ HEK293T cells were seeded in 10-cm tissue culture plates and transfected with plasmids expressing MERS-Spike or VSV-G protein using TurboFectin 8.0 (OriGene) transfection reagents at about 80% confluence. To produce HIV/MERS-Spike pseudoparticles, 10 μg pNL Luc E-R-(NIH-AIDS-Reagent Program) and 10 μg pVax1-MERS-Spike from various clades were co-transfected into cells. After 12 h twelve hours, transfection media was removed and replaced with fresh media for approximately 12 h and cells were incubated for 24-48 h at 37° C. The pseudovirion-containing media was collected, filtered, and pseudovirions were concentrated at 40,000 rpm in a SW41 rotor for 1 h through a 20% sucrose cushion prepared in TNE buffer (10 mM Tris, 135 mM NaCl, 2 mM EDTA, pH 8.0). The pellet was resuspended overnight in 500 μL TNE buffer, aliquoted and stored at −80° C.

Neutralization Assay.

The 50% tissue culture infectivity dose ($TCID_{50}$) was calculated and a standard concentration of virus (i.e. $100TCID_{50}$) was used for the neutralization test throughout the study, which was performed with the mouse sera from MERS-HCoV DNA immunized animals. Briefly, the mouse sera were serially diluted in MEM and incubated with 50 ul of DMEM containing 100 infectious HCoV-EMC/2012 (Human Coronavirus Erasmus Medical Center/2012) particles per well at 37° C. After 90 min, the virus-serum mixture was add to a monolayer of Vero cells (100,000 cells/per well) in a 96-well flat bottom plate and incubated for 5 days at 37° C. in a 5% $CO_2$ incubator. The titer of neutralizing antibody for each sample was reported as the highest dilution with which less than 50% of the cells show CPE. Values were reported as reciprocal dilutions. All the samples were run in duplicate so the final result was taken as the average of the two. The percent neutralization was calculated as follows: Percent neutralization={1-PFU mAb of interest (each concentration)/Mean PFU negative control (all concentrations)}. Neutralization curves were generated and analyzed using GraphPad Prism 5. Nonlinear regression fitting with sigmoidal dose-response (variable slope) was used to determine the $IC_{50}$ and $IC_{80}$. Positive and negative control sera were included to validate the assay.

For the neutralization tests, MERS-Spike pseudoparticles (50 ng) were pre-incubated with serially diluted mouse sera for 30 min at 4° C. and then added to cells in triplicate. CPE was read at three days post infection. The highest serum dilution that completely protected the cells from CPE in half of the wells was taken as the neutralizing antibody titer. For the luciferase-based assay, MERS-Spike pseudoparticels infected cells were lysed in 50 μl protein lysis buffer and 100 μl of luciferase substrate at two days post infection. Luciferase activity was measured in a 96 Microplate Luminometer (GLOMAX; Promega Corporation).

Cell Viability Assay and Annexin V/FITC Assay.

Cell viability was determined using 3-(4,5-dimethylthiazol-2-yl)-2,5-diphenyl-tetrazolium bromide (MTT, 5 mg/ml, Sigma). The cultures were initiated in 96-well plates at a density of $2.5\times10^3$ cells per well. After 48 h incubation, cells were infected with MERS-pesudovirus and cultured for 48 h. After incubation, 15 μl of MTT reagent was added to each well and incubated for 4 h at 37° C. in the dark. The supernatant was aspirated and formazan crystals were dissolved in 100 μl of DMSO at 37° C. for 15 min with gentle agitation. The absorbance per well was measured at 540 nm using the a Luminometer Reader (GLOMAX; Promega). Data was analyzed from three independent experiments and then normalized to the absorbance of wells containing media only (0%) and untreated cells (100%). $IC_{50}$ values were calculated from sigmoidal dose response curves with Prism GraphPad software.

The Annexin V-FITC binding assay was performed according to the manufacturer's instructions using the Annexin V-FITC detection kit I (BD Biosciences). The cells were infected with MERS-pseudovirus for 12 h. The cells were counted after trypsinization and washed twice with cold PBS. The cell pellet was resuspended in 100 μl of binding buffer at a density of $1\times10^3$ cells per ml and incubated with 5 μl of FITC-conjugated Annexin-V and 5 μl of PI for 15 min at room temperature in the dark. Four hundred microliters of 1× binding buffer was added to each sample tube, and the samples were immediately analyzed by flow cytometer (BD Biosciences). Data were analyzed using FlowJo software (Tree Star).

Non-Human Primate (NHP) Immunization and MERS Challenge.

Three groups of Rhesus macaques received 3 doses (prime and 2 boosts) administered 3 weeks apart (weeks 0, 3, 6). Group 1 and 2 macaque received a total of 0.5 mg and 2 mg/dose of a DNA vaccine expressing the MERS-Spike (N=4) vaccine by intramuscular immunizations with the EP device. Groups 1 and 2 received the full-length consensus MERS Spike antigen. Group 3 macaque received a total of 2 mg/dose of a control vaccine (pVax1). The dose and immunization regimen of DNA vaccine used in these studies were previously determined to be optimum in rhesus macaques. Blood was collected after each dose to analyze serum antibody, and neutralization and systemic T cell responses. Animals were anesthetized intramuscularly with ketamine HCL (10-30 mg/kg). The vaccine was administered to each thigh (one injection site per thigh per vaccination) and delivered by the intramuscular (IM) route. Immediately following the DNA injection, 3 pulses at 0.5 A constant current with 52 ms pulse length with is between pulses was applied for IM administration.

NHP Challenge.

Three groups of Rhesus macaques received 3 doses (prime and 2 boosts) administered 3 weeks apart (weeks 0, 3, 6). Group 1 and 2 macaque received a total of 0.5 mg and 2 mg/dose of a DNA vaccine expressing the MERS-Spike (N=4) vaccine by intramuscular immunizations over the with the EP device. Group in 3 macaque received a total of 2 mg/dose of a control vaccine (pVax1). The dose, immunization regimen of DNA vaccine to be used in these studies were previously determined to be optimum in rhesus macaques. Blood was collected after each dose to analyze serum antibody and Neutralization and systemic T cell responses. Animals were anesthetized intramuscularly with ketamine HCL (10-30 mg/kg). The vaccine was administered to each thigh (one injection site per thigh per vaccination) and delivered by the IM route. Immediately following the DNA injection, a 3 pulses at 0.5 A constant current with 52 ms pulse length with is between pulses was applied for IM administration.

Challenge: 12 healthy rhesus macaques (Macaca mulatta), aged 4-6 years, were inoculated with a total of 7×10⁶ TCID50 of MERS-CoV by combined intratracheal, intranasal, oral and ocular routes as previously established (Falzarano et al Nature Medicine 19, 1313-1317 (2013) Animals were randomly assigned to either the treated or untreated group in a nonblinded manner.

Statistical Analysis.

The animal experiments to evaluate immune responses were repeated at least three times and the response of each mouse was counted as an individual data point for statistical analysis. All data were presented as means±standard deviations. Data obtained from animal studies and various immune assays were examined by using one-way ANOVA from GraphPad; differences were considered significant at p<0.05. GraphPad Prism v. 5.0 (GraphPad Software, Inc.) was used for statistical analysis.

Example 10

Cloning and Expression of MERS-HCoV Spike and Spike ΔCD Proteins

Figure 19A:
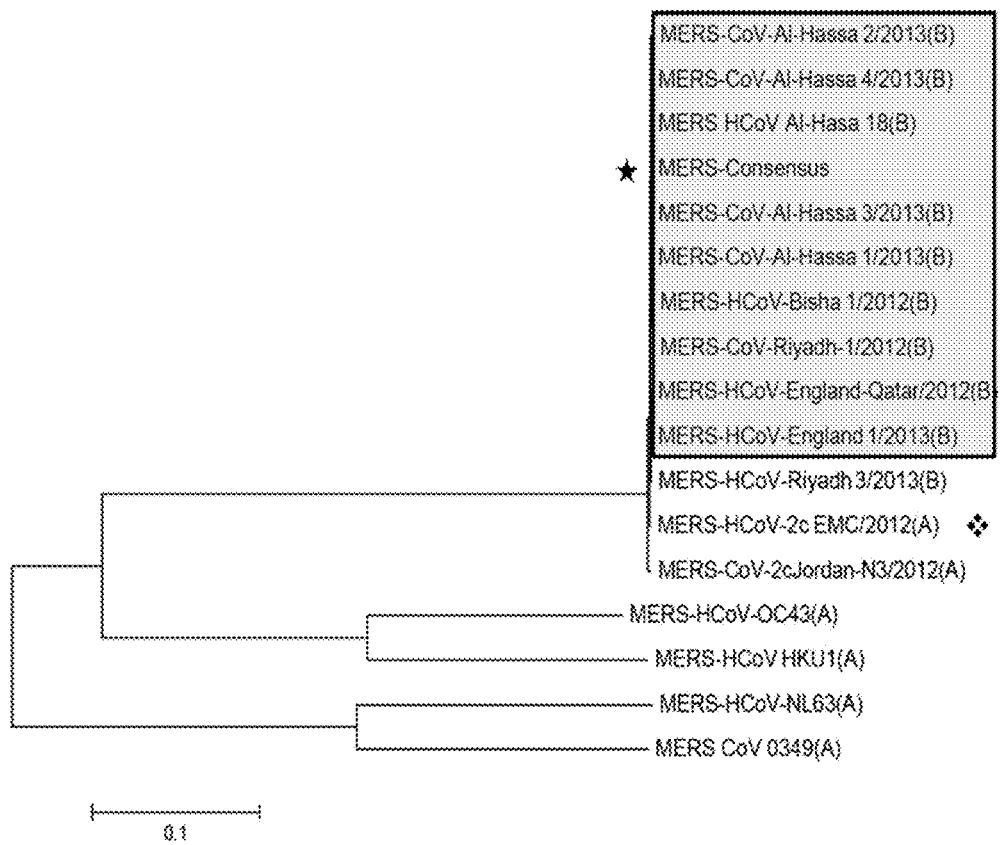
FIG. 19A through FIG. 19D, shows the construction and characterization of MERS-HCoV Spike DNA vaccine.
Figure 19B:
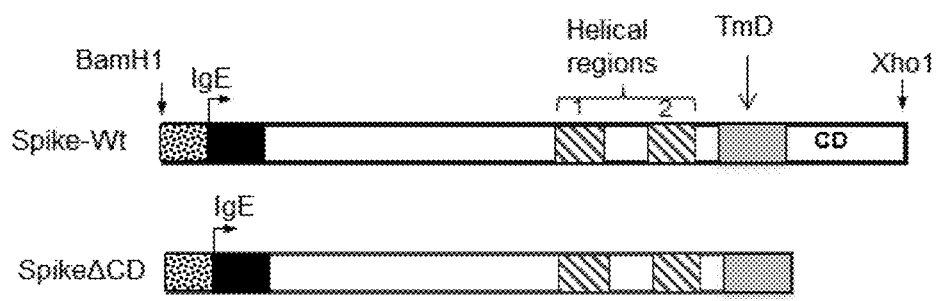

The consensus sequence for MERS-HCoV Spike gene was generated from 16 Spike genomic sequences deposited in the GenBank-NCBI database. For the immunogen design, sequences from both Clade A and B were included in the consensus sequence and the resulting consensus sequence was tested by measuring the neutralizing activity across clades A and B viral strains of MERS-HCoV. As shown in FIG. 19A, the phylogenetic position of the MERS-HCoV-Spike consensus sequence was centered in the Clade B quadrant, which was due to the multiple sequences that fall within this clade. Furthermore, two consensus sequences of the MERS Spike glycoprotein were designed, in which one construct's cytoplasmic domain sequence was fully intact and the second construct's cytoplasmic domain was truncated. These constructs were termed the MERS-HCoV Spike (Spike-Wt) and the cytoplasmic portion truncated (SpikeΔCD), respectively. For both immunogens, several modifications were made to enhance in vivo expression, including addition of a highly efficient IgE leader peptide sequence to facilitate expression and mRNA export. The inserts were then sub-cloned into the pVax1 vector (FIG. 19B). Construction of these Spike-Wt and SpikeΔCD DNA constructs is also described above in Examples 1 and 2.

Figure 19C:
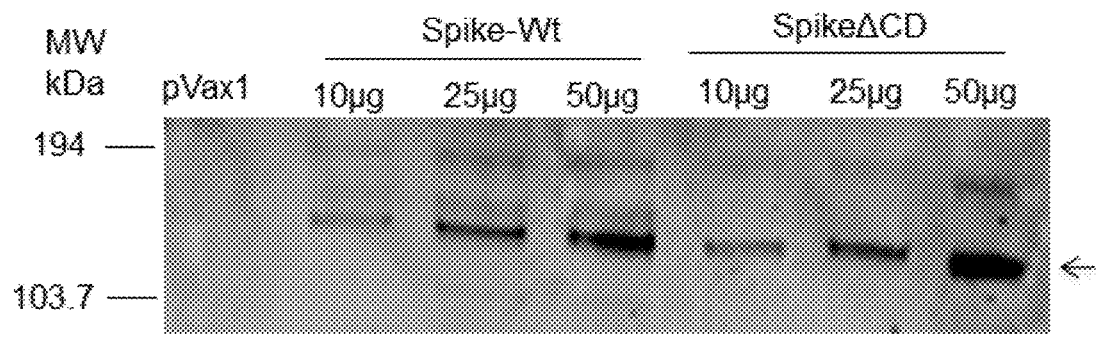

The plasmids were transfected into 293T cells separately, and the expression of Spike protein was evaluated by Western blotting. The mouse antiserum specific for Spike-Wt proteins from the immunized mice were used to detect the expression of Spike protein from the plasmid transfected cells lysates. At 48 hours post-transfection, protein lysates were extracted. Strong specific bands of MERS-Spike protein (140 kDa) was detected in Spike-Wt and SpikeΔCD transfected cells, but not in lysates from cells transfected with the control vector (an empty pVax1 plasmid) (FIG. 19C).

Figure 19D:
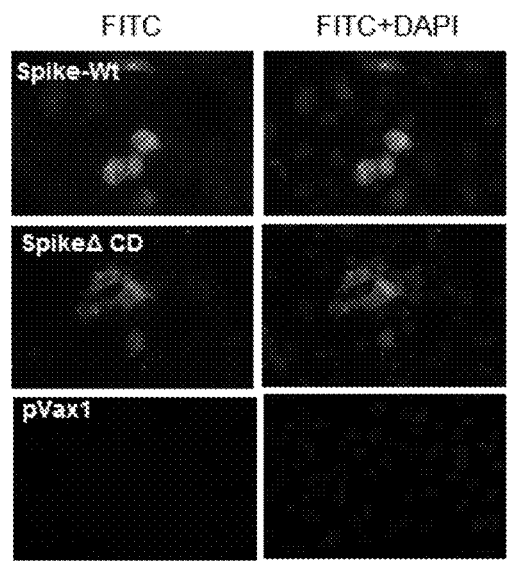

In addition, the expression and localization of Spike protein upon transfection was investigated using an immunoflorescent assay (IFA). The IFA using mouse Spike antiserum revealed a strong signal was present in the cytoplasm (FIG. 19D). The positive signal was not detected in intact cells transfected with pVax1 vector. Both full length construct (Spike-Wt) and the cytoplasmic domain mutant construct (SpikeΔCD) were localized similarly within transfected cells. These results demonstrate the ability of the MERS-HCoV constructs to express strongly in mammalian cells and that antibodies induced by these constructs can bind their target antigen.

Example 11

Functional Expression and Infection by MERS-HCoV DNA Constructs

Figure 20B:
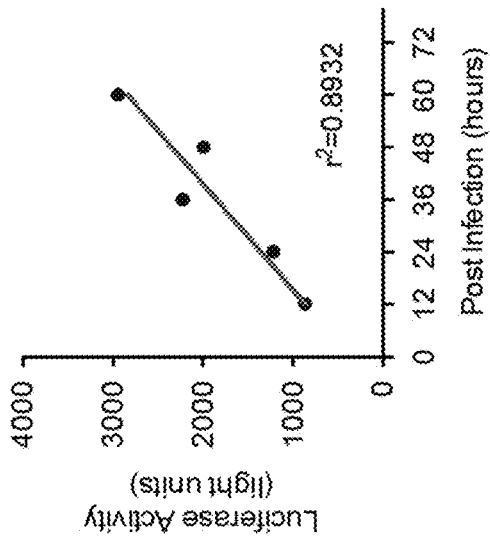
FIG. 20A through FIG. 20C, shows the construction and characterization of MERS-Spike pseudovirus.
Figure 20C:
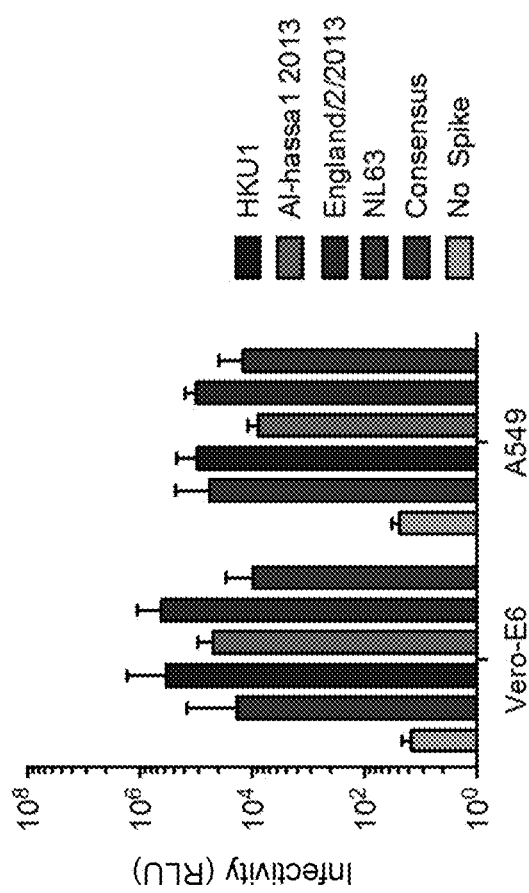
Figure 20A:
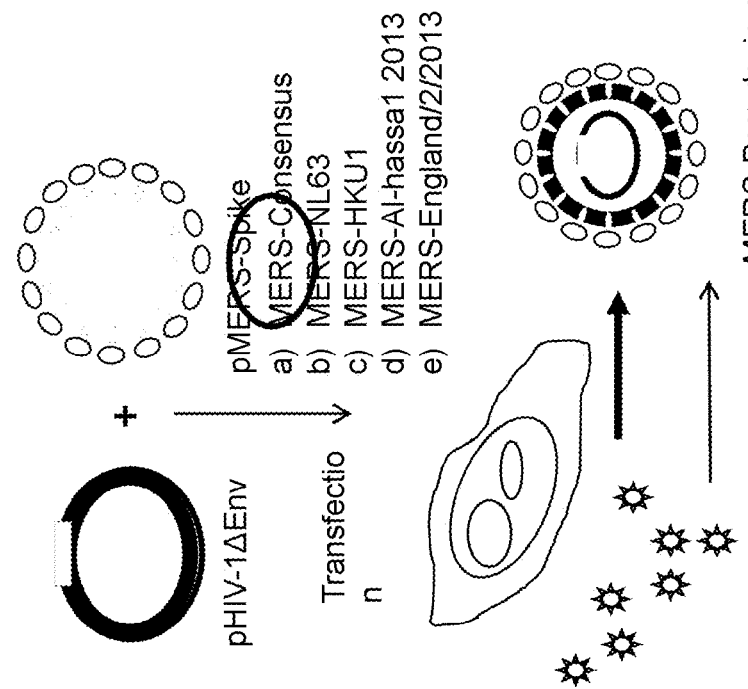

To determine the functionality of the consensus sequence immunogens (e.g., viral binding and entry), a pseudoviral expression system was developed to test the viral entry properties of the consensus constructs. Specifically, MERS-HCoV pseudoviral particles were produced by co-transfection of 293T cells with plasmids encoding the MERS-Spike antigen(s) and an HIV-1 luciferase reporter plasmid, which does not express HIV-1 envelope (FIG. 20A). Particles were produced by transfection of 293T cells with various MERS-Spike gene+lentiviral genome fragment. This generated robust viral particle formation. To characterize MERS-Spike mediated infection, a time course analysis was performed measuring the luciferase activity in cells synchronously infected with the consensus MERS-Spike pseudovirus (FIG. 20B). As seen in FIG. 20C, inoculation of Vero cells and A549 cells cell lines that expressed functional receptors for MERS-CoV with pseudoviral particles produced a strong luciferase signal, indicating productive infection with the pseudovirus. These experiments showed the development of MERS pseudovirions with Spike protein, which entered target cells and established a pseudovirus-based inhibition assay for the detection of neutralizing antibodies.

Example 12

Increased Immunogenicity of MERS-HCoV DNA Vaccines in Mice

Figure 21A:
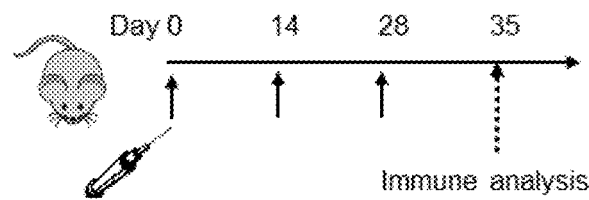
FIG. 21A through FIG. 21D, shows the functional profile of cellular immune responses elicited by MERS-HCoV vaccines.

To investigate the immunogenicity of the consensus and modified Spike glycoproteins, constructs were analyzed for their ability to elicit immune responses after intramuscular injection in C57BL/6 mice. Female C57BL/6 mice (n=9) were vaccinated with 25 µg of one of three DNA plasmids: Spike-Wt, SpikeΔCD or a control pVax1 vector. Immediately following each immunization, the adaptive electroporation (EP) system was used. Animals were vaccinated three times at two-week intervals, and immune responses were measured one week following the third immunization as described in FIG. 21A.

Figure 21B:
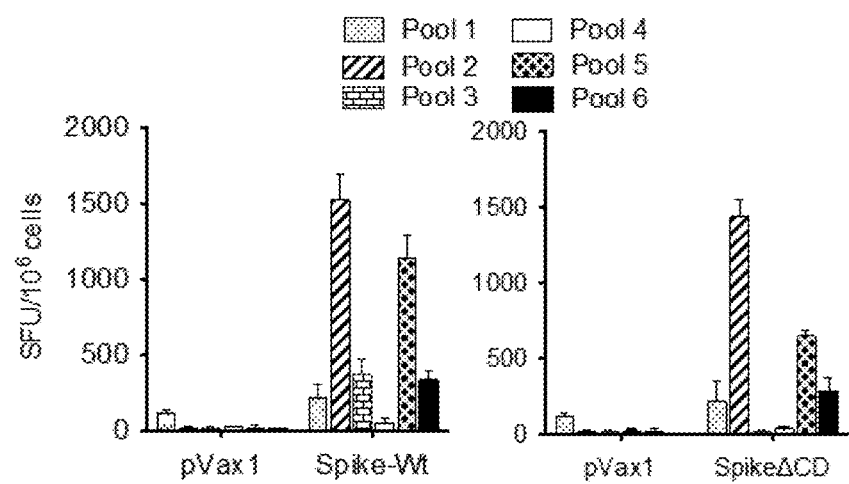

Cell-mediated immunity was evaluated by using a standard ELISpot assay to monitor the ability of splenocytes from the immunized mice to secrete cytokines after antigen specific in vitro restimulation with peptide pools encoding the entire protein region of the MERS-Spike glycoprotein. ELISpot assays were carried out one week following the third immunization. As shown in FIG. 21B, the splenocytes from Spike-Wt as well as immunized SpikeΔCD vaccination induced strong cellular immune responses against multiple peptide pools. Peptides in pools 2 and 5 appeared dominant with both constructs.

Figure 21C:
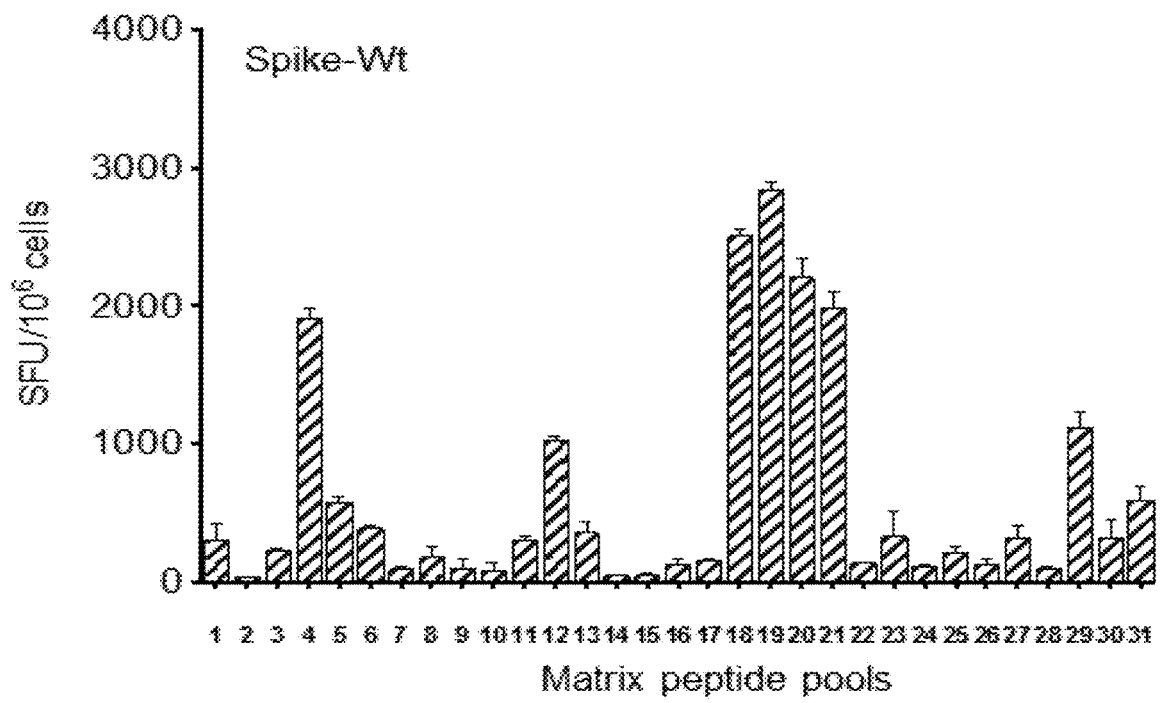
Figure 21D:
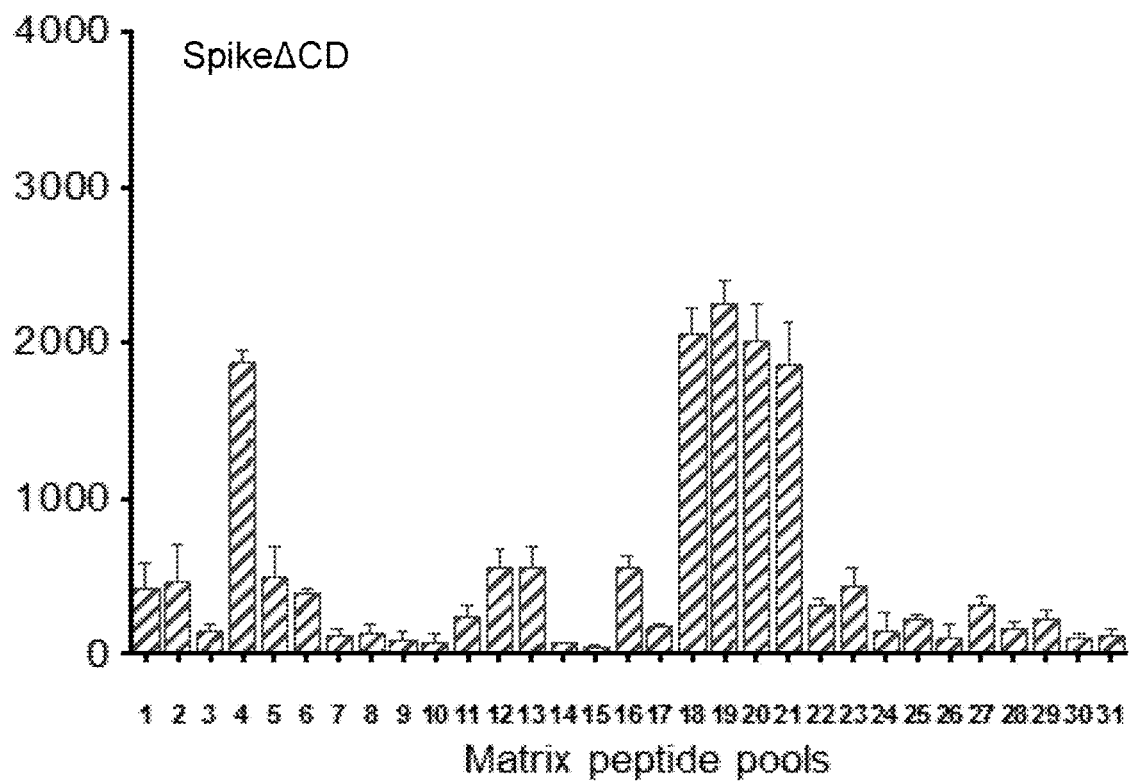

Based on these T cell responses, detailed mapping against 31 diverse pools spanning the entire MERS-Spike protein was performed. Two hundred twenty seven peptide pools, containing 15-mer peptides with 11 amino acid overlaps and spanning the residues of Spike protein, were generated. Thirty-one peptide pools were prepared using the matrix format and were tested. Following restimulation with the peptide, a strong CD8⁺ T cell response was detected against several regions on the Spike protein (FIG. 21C and FIG. 21D). There were fifteen matrix pools showing more than 100 spots, indicating that MERS-Spike elicited a broad range of cellular immune responses. Four-peptide-pools in the region from amino acid 301-334 were identified. Importantly the Spike-Wt as well as Spike-ΔCD immunogen reacted to 4 major regions spanning the peptide pools 4-6, 11-13, 18-21 and 29-31. However, the dominant pools appeared to span 18-21. These pools included a computer identified CD8+ T-lymphocyte immunodominant epitope at amino acids 307-321 (RKAWAAFYVYKLQPL (SEQ ID NO:7)), which may be a dominant response by both antigens (FIGS. 21C and 21D).

Example 13

MERS-Spike Vaccine-Induced T Cell Responses were Polyfunctional

Figure 25A:
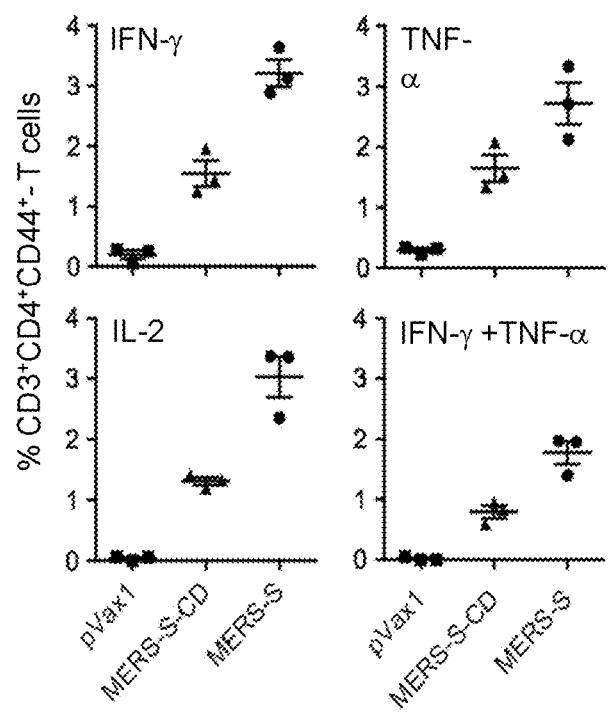
FIG. 25A through FIG. 25D, shows the functional profile of $CD4^+$ and $CD8^+$ T cell responses elicited by MERS-Spike vaccine. The cytokine profiles of specific $CD4^+$ T cells and $CD8^+$ T cells induced after vaccination are shown in FIG. 25A and FIG. 25B, respectively. Mouse splenocytes (n=3) were isolated one week after the final DNA immunization and were stimulated with pooled MERS-Spike peptide ex-vivo. Cells were stained for intracellular production of IFN-γ, TNF-α, and IL-2, and then analyzed by FACS.
Figure 25B:
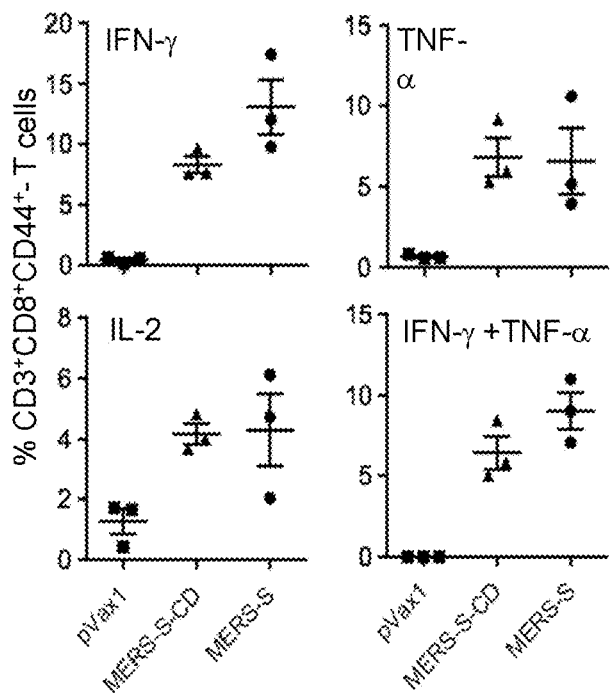

In order to further determine the phenotype of the induced T cell responses, the polyfunctional T cell responses were assessed. Polychromatic flow cytometry was employed to measure the production of IFN-γ, IL-2 and TNF-α induced in an antigen specific fashion in both CD4+ and CD8+ T cells. Representative flow cytometry profiles of MERS-Spike-specific IL-2, TNF-α and IFN-γ, secreting CD4+ and CD8+ T cells are shown in FIGS. 25A and 25B respectively. The constructs generated comparable responses from CD8+ T cells; the full-length construct induced significantly higher percentages of CD4+ T cells secreting IL-2, TNF-α and IFN-γ.

Figure 25C:
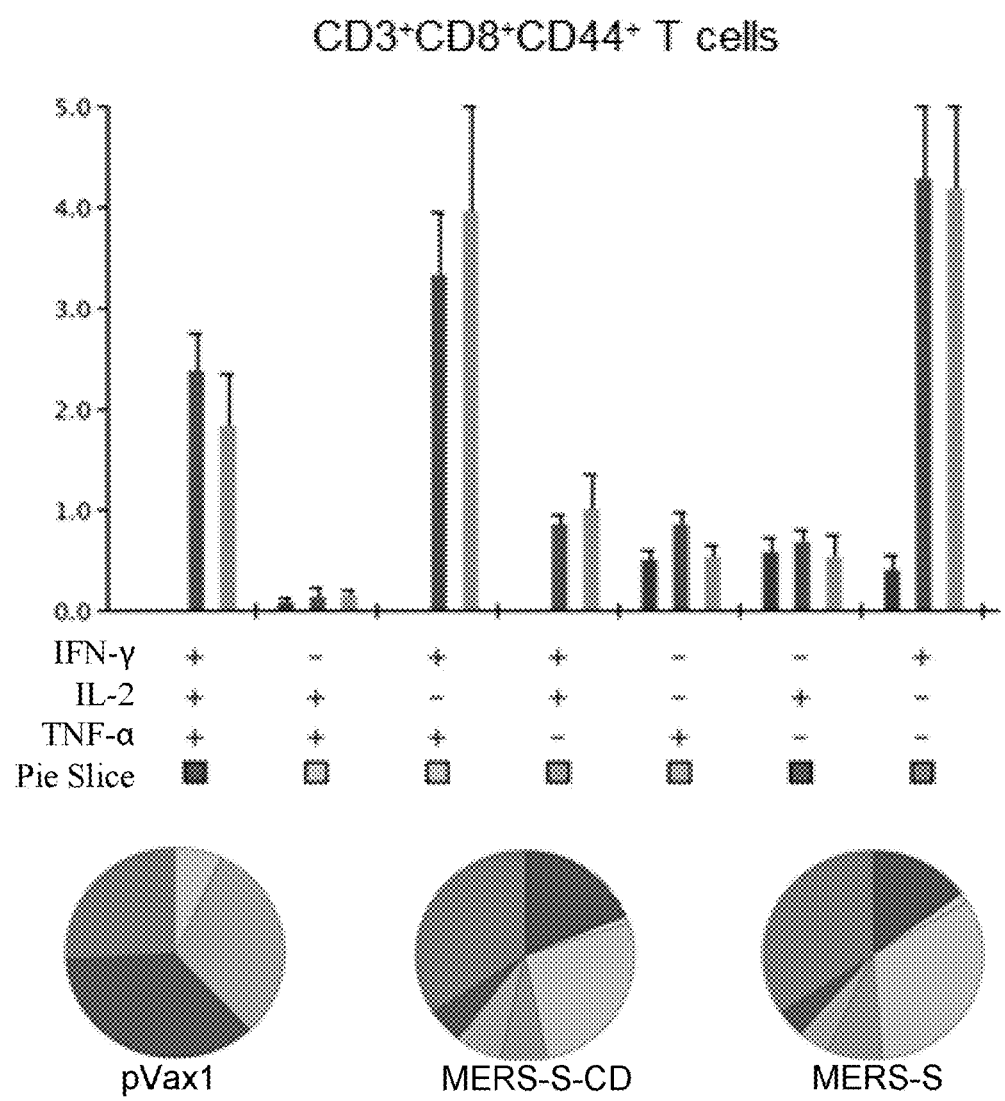
Figure 25D:
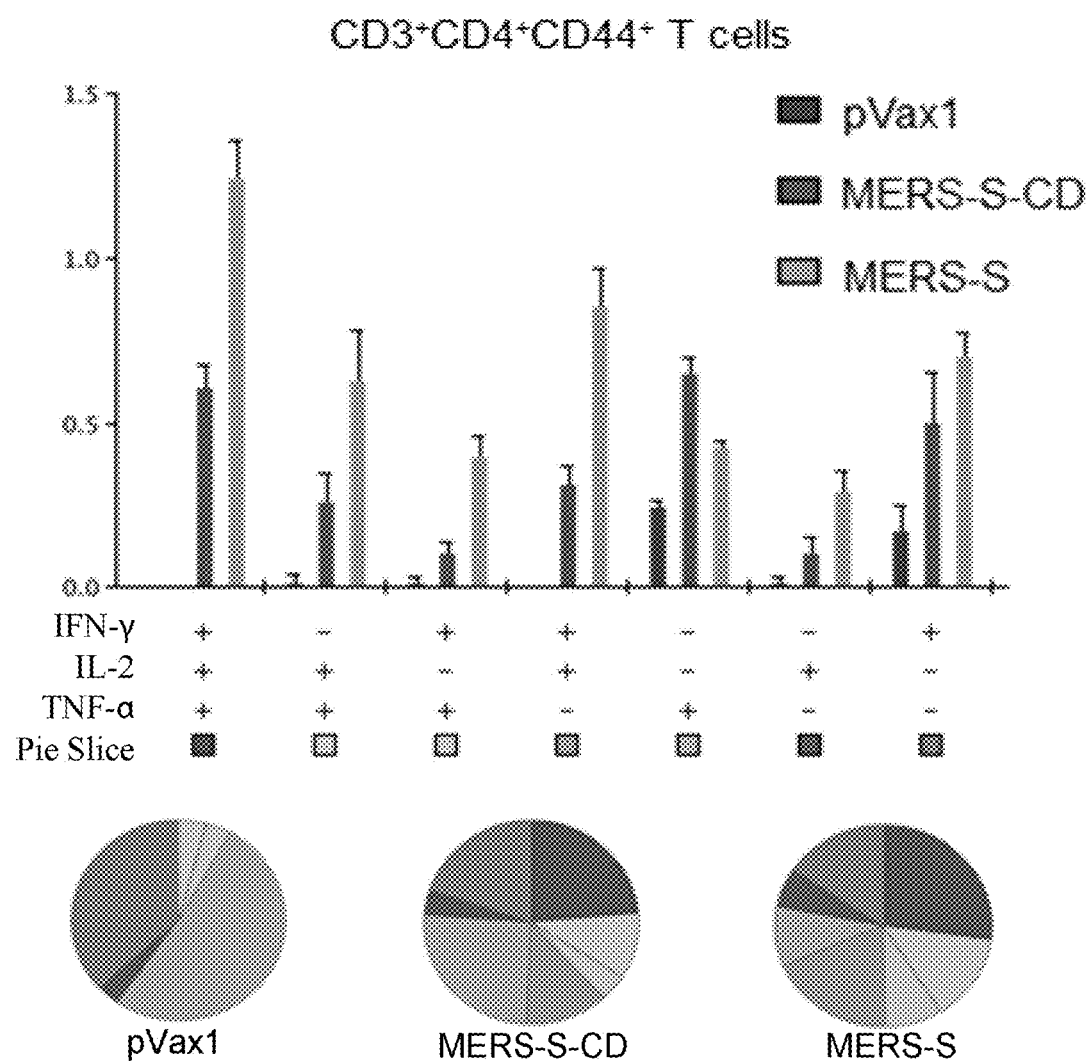
Figure 26A:
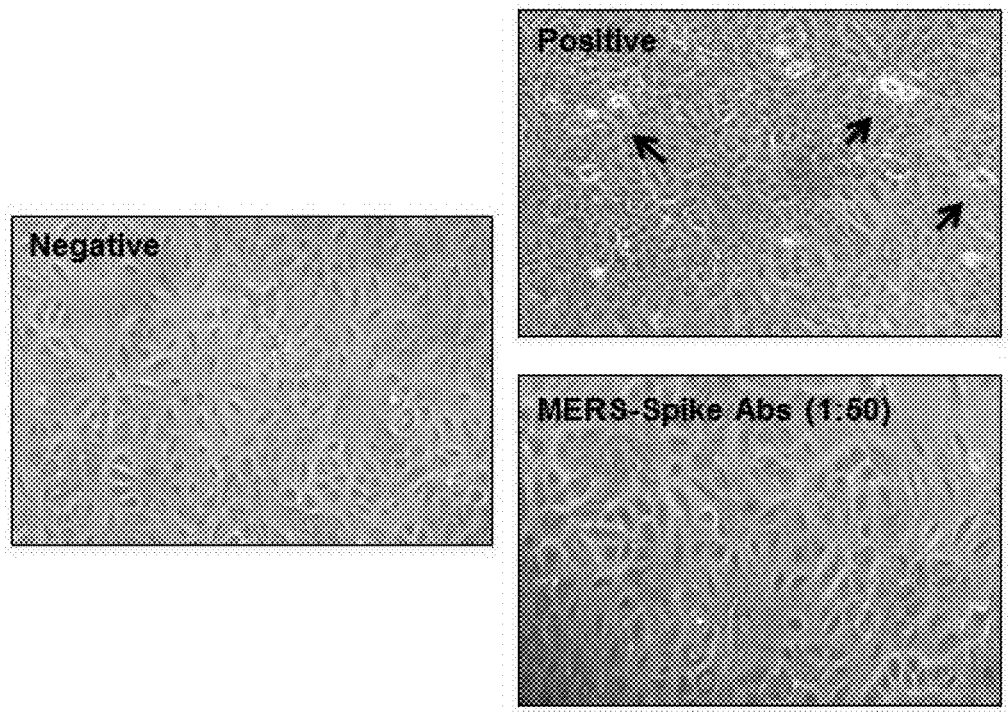
FIG. 26A through FIG. 26B, shows the inhibition of apoptosis induced by MERS-S pseudoviruses by Spike DNA immunized mouse immune sera.
Figure 26B:
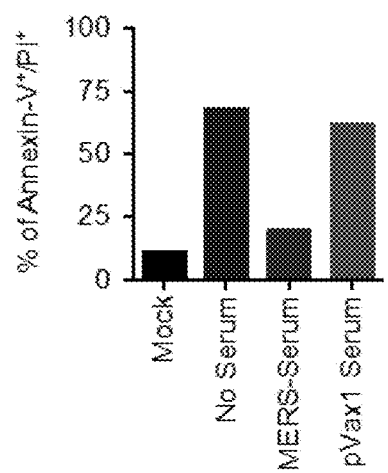

The magnitude of vaccine-induced CD4+ and CD8+ T cell responses for MERS—HCoV-Spike as well MERS-HCoVΔCD vaccine construct were compared. Using Boolean gating, the ability of individual cells to produce multiple cytokines, i.e. polyfunctionality of the vaccine-induced CD4+ and CD8+ T cell response, was assessed (FIGS. 25C and 25D). This analysis showed that the CD8+ T cell responses were similar in the full length or truncated Spike protein vaccine groups, however, the magnitude of the CD4+ T cell responses were greater in the full length Spike antigen vaccine group. Seven distinct Spike-specific CD4+ and CD8+ T-Cell populations were identified. Although the proportion of tri, bi-, and mono-functional cells varied slightly between these two vaccine groups, there were trends observed in both groups with overall magnitude favoring the full length construct in both CD4+ as well as CD8+ T cell response induction. When the responses were then further divided into their 7 possible functional combinations, it was observed that CD8+ T-cells in both of the vaccination groups were similar except for induction of CD8+ T cells that produce IFN-γ, which again favored the full length construct in magnitude (FIGS. 25C and 25D).

Example 14

Figure 18B:
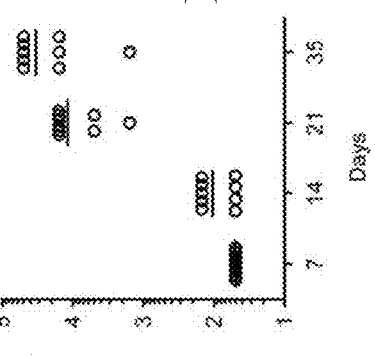
In FIG. 18B, the antibody response over time after vaccination with consensus MERS-Spike DNA vaccine (MERS-S) is shown.
Figure 18C:
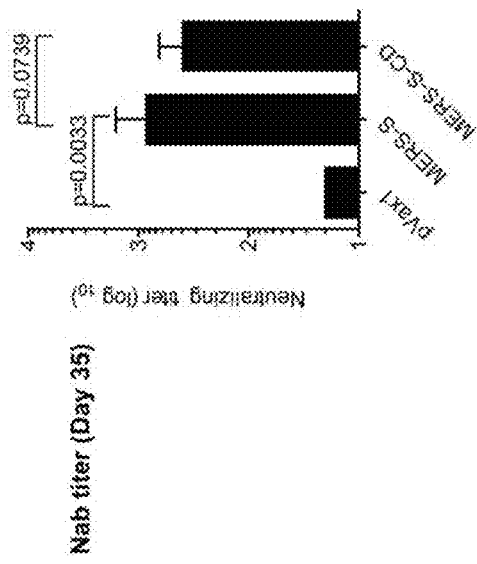
In FIG. 18C, the neutralizing antibody titer at day 35 is shown after vaccination with pVax1 DNA vector (negative control), MERS-S DNA vaccine, or MERS-S-CD DNA vaccine. Mouse sera were serially diluted in MEM and incubate with 50 ul of DMEM containing 100 infectious HCoV-EMC/2012 (Human Coronavirus Erasmus Medical Center/2012) particles per well at 37° C. After 90 min, the virus-serum mixture was add to a monolayer of Vero cells (100,000 cells/per well) in a 96-well flat bottom plate and incubate for 5 days at 37° C. in a 5% $CO_2$ incubator. The titer of neutralizing antibody for each sample is reported as the highest dilution with which less than 50% of the cells show CPE. Values are reported as reciprocal dilutions. All the samples were run in duplicate so the final result was taken as the average of the two. The percent neutralization was calculated as follows: Percent neutralization={1-PFU mAb of interest (each concentration)/Mean PFU negative control (all concentrations)}.
Figure 18A:
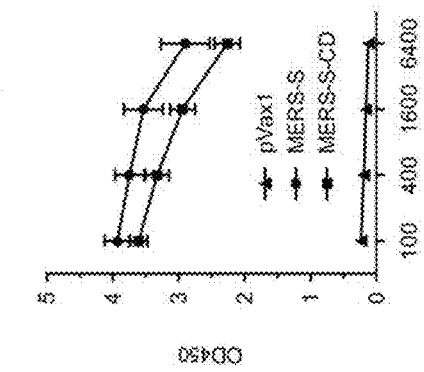
FIG. 18A shows the antibody response after vaccination with pVax1 DNA vector (negative control), consensus MERS-Spike DNA vaccine (MERS-S), or consensus MERS-Spike-ΔCD DNA vaccine (MERS-S-CD). The antibody response was measured by ELISA.
Figure 22A:
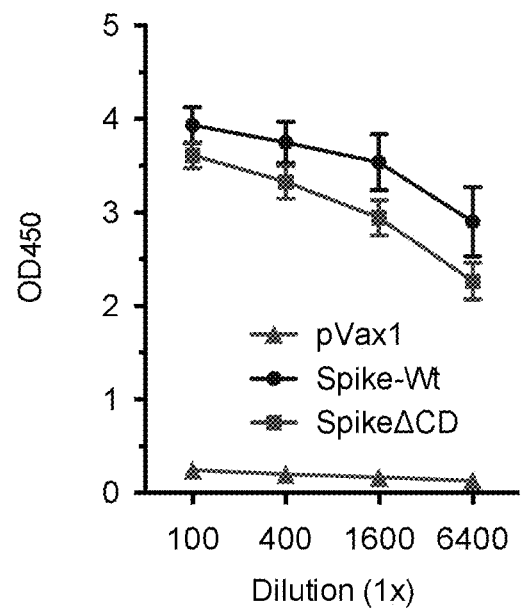
FIG. 22A through FIG. 22E, shows systemic anti-MERS-HCoV IgG levels after DNA immunization.
Figure 22B:
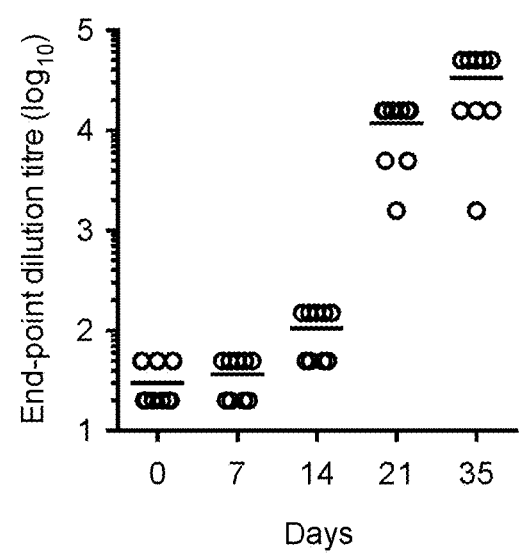
Figure 22C:
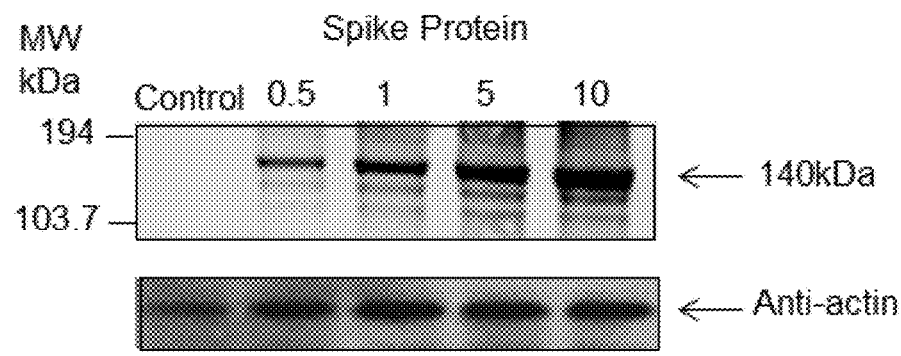

MERS-HCoV-Spike Vaccination Induced Sufficient Binding Antibody Responses as Well as Neutralizing Antibody (Nab) Responses in Mice The induction of humoral immunity by the two constructs was also examined. Serum samples were obtained before and after DNA immunization in mice. The anti-Spike humoral immune responses were analyzed for binding to recombinant Spike antigen as well as in functional antibody studies. As shown in FIGS. 18A and 22A, all vaccinated animals induced specific antibody responses compared to the control animals that were immunized with plasmid backbone. Similar to the CD4+ T cell responses, the binding antibody activity was stronger in the full-length immunized animals quantified as end point titer (FIGS. 18B and 22B). The antibodies generated from the immunized mice also bound to the MERS-Spike recombinant protein in Western blot assay (FIG. 22C). Collectively, these data indicated that the Spike DNA vaccine induced specific antibody production and antibodies that bound specifically to the target Spike antigen.

Example 15

Figure 22D:
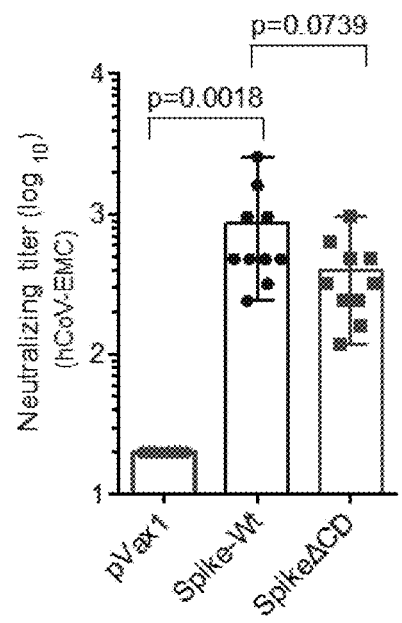

Antisera to MERS-HCoV-Spike Demonstrated Neutralization Activity Against MERS Virus The neutralizing activity of serum from mice immunized with either the Spike-Wt or SpikeΔCD vaccine was assessed via a viral neutralization assay with the Clade A strain virus, HCoV-EMC/2012 (Human Coronavirus Erasmus Medical Center/2012). Sera were collected from mice (n=9 per group) vaccinated with either Spike-Wt or SpikeΔCD and the negative control pVax1. As shown in FIGS. 18C and 22D, both vaccines induced neutralizing antibody titers that were significantly higher than sera titers from mice immunized with a control vector (pVax1) alone (p=0.0018). Similar to the antibody binding assays, though not significantly different, the truncated construct appeared to induce a lower level of neutralizing responses than the full-length construct.

Figure 22E:
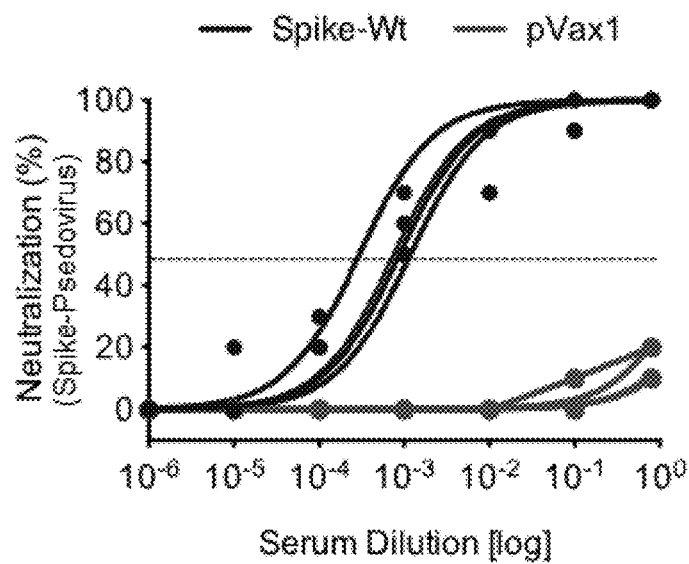
Figure 24A:
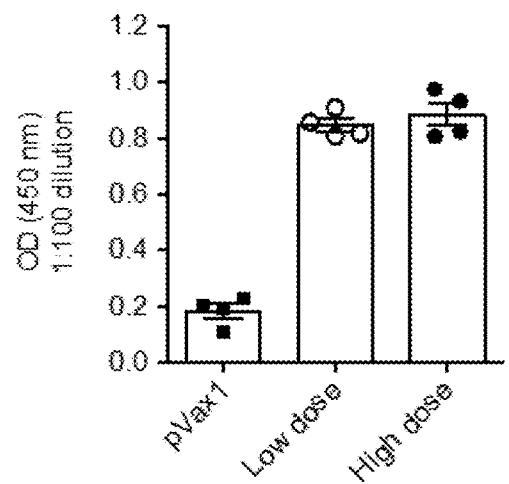
FIG. 24A through FIG. 24D, shows antibody binding titers and neutralizing antibody (Nab) response following MERS-Spike DNA vaccinations.
Figure 24B:
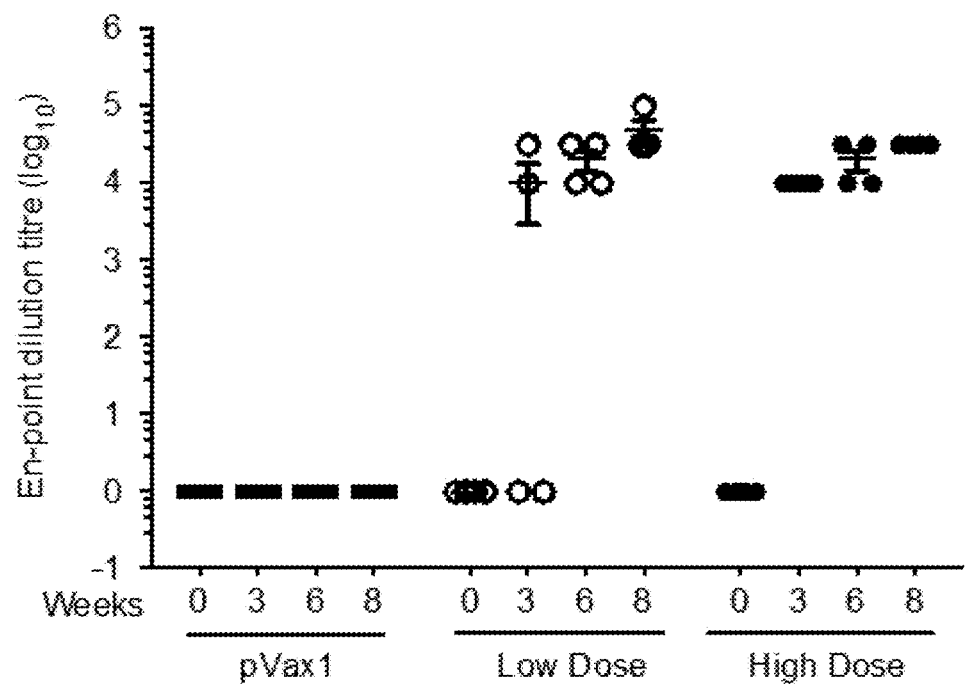
Figure 24C:
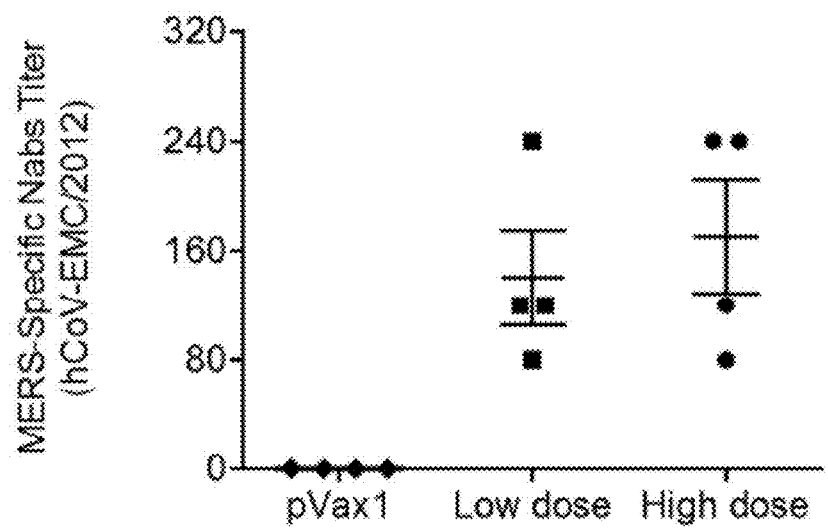
Figure 24D:
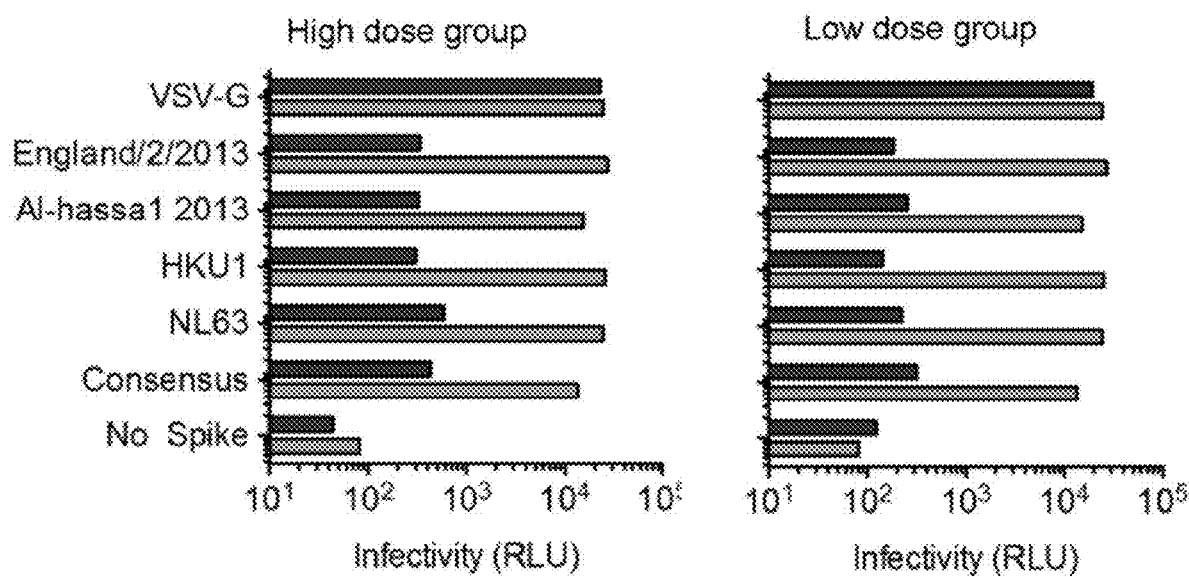

As the neutralization assay was limited due to the lack of available full-length virus at this time, the pseudoparticle neutralization assay described above was utilized to test the ability of the antisera to neutralize MERS-Spike pseudovirus. As shown in FIG. 22E, MERS-Spike-Wt vaccinated mouse (n=4) antisera efficiently inhibited infection of Vero cells by MERS-Spike pseudovirus with 50% neutralizing Abs titers ranging from 120 to 960 and higher. Further, the above sera were evaluated for neutralizing activity against different clade of MERS-CoV infection using MERS-pseudo virus based inhibition assay (See the FIG. 24D). FIG. 24D shows detection of neutralizing antibodies of vaccinated sera against MERS-CoV infection. Briefly, Macaque's sera, at two week after the third immunization, were collected from the vaccinated animals and MERS-CoV pseudovirus-based inhibition assay in Vero cells for both MERS-Low and high dose groups were performed. Pseudovirus entry was quantified by luciferase activity at 40 hrs post inoculation.

The results indicated that the neutralizing antibodies from these sera showed broader inhibition as tested by the pseudovirus inhibition assay. Overall, these results were consistent with the results obtained from the neutralizing assay using wild-type MERS-HCoV and further illustrated the cross protective nature of the antibody response induced by this vaccine.

Example 16

Generation of Multi-Functional T Cells in the Peripheral Blood of Macaques Following MERS-Spike DNA Vaccination Vaccine efficacy against MERS-challenge was also assessed in the preclinical non-human primates model. This study is outlined in Table 2 below.

TABLE 2

| Immunization | Group 1 | Group 2 | Group 3 |
| --- | --- | --- | --- |
| Week-0 | Control (pVax1) | pMERS-Spike Low | pMERS-Spike-High |
| Week-3 | Control (pVax1) | pMERS-Spike Low | pMERS-Spike-High |
| Week-6 | Control (pVax1) | pMERS-Spike Low | pMERS-Spike-High |
| Week 6-8 | Post Immunization T cell & nAbs Analysis | Post Immunization T cell & nAbs Analysis | Post Immunization T cell & nAbs Analysis |
| Week-8-9 | Transfer to NIH-BSL4 Lab | Transfer to NIH-BSL4 Lab | Transfer to NIH-BSL4 Lab |
| Week-10 | MERS-Challenge (intranasal (i.n.)) | MERS-Challenge (i.n.) | MERS-Challenge (i.n.) |
| Week 12 | Post Challenge Analysis | Post Challenge Analysis | Post Challenge Analysis |

Figure 23A:
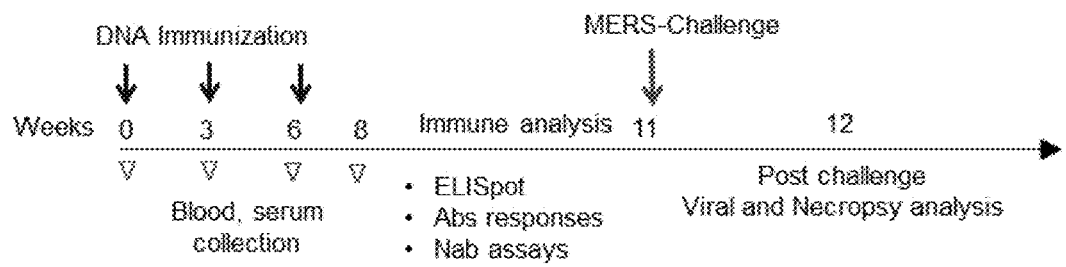
FIG. 23A through FIG. 23C, shows the analysis of interferon-gamma (IFN-γ) producing cells induced by MERS-Spike DNA vaccine in non-human primates (NHP).
Figure 23B:
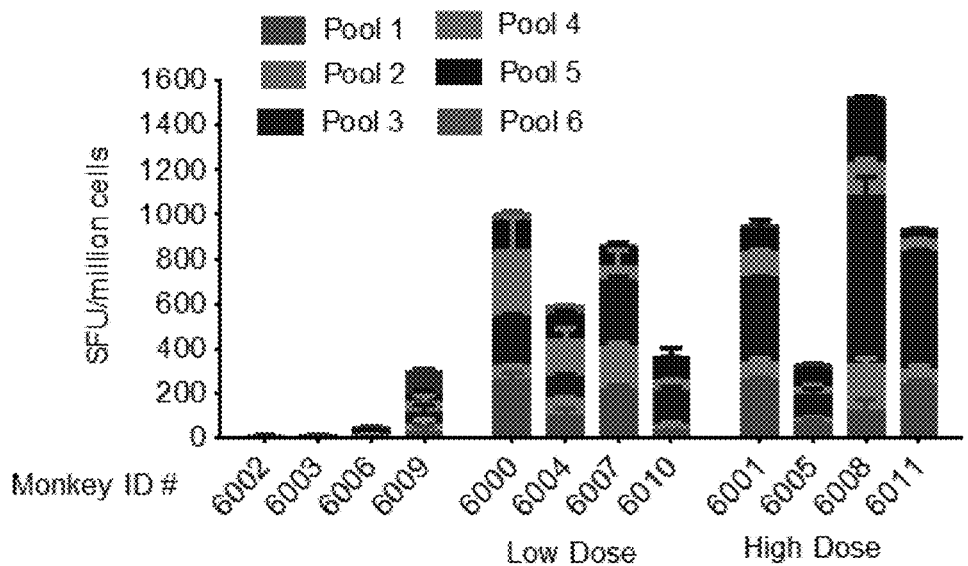
Figure 23C:
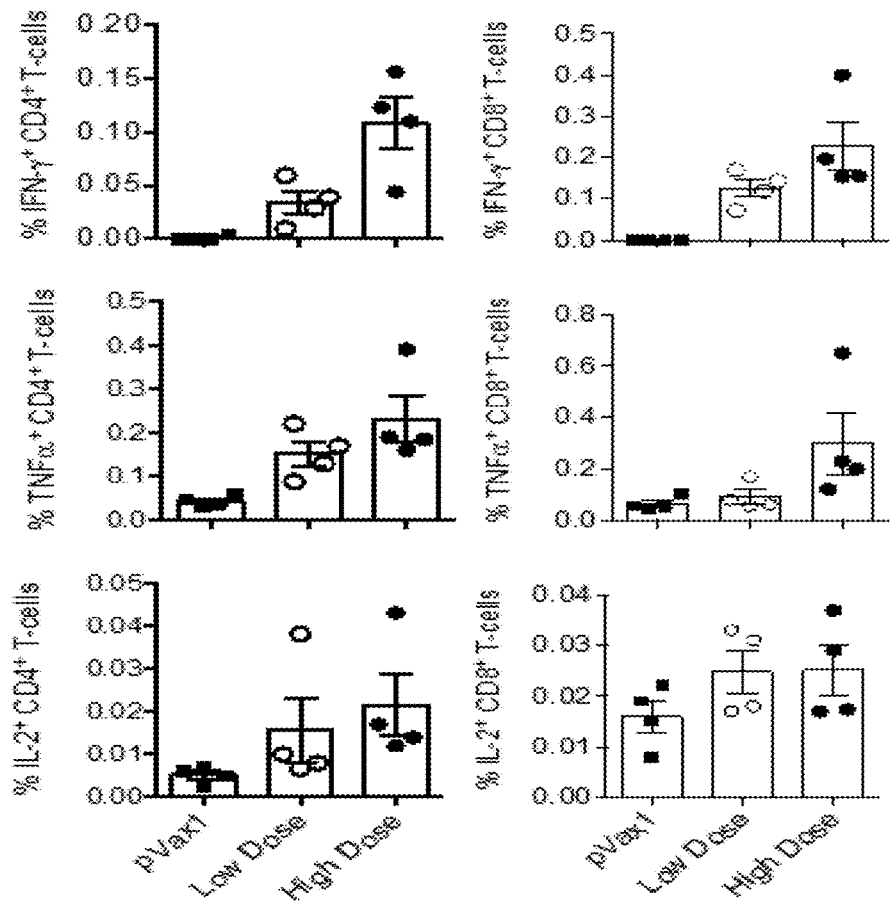

Three groups (low, high and control) of animals (four Indian Rhesus macaques per group) were immunized with MERS-Spike vaccine as described in Example 9 (FIG. 23A). To determine the impact of the MERS-Spike vaccine on T cell responses, an ELISpot assay was used to enumerate the T cells in the blood of vaccinated animals secreting IFN-γ in response to stimulation with pools of overlapping peptides derived from the full length of MERS-Spike protein. After three immunizations, the number of MERS-Spike specific T cells present in the blood of the vaccinated animals and the total vaccine response in low dose groups were between 600 and 1,100 SFU/million PBMCs, whereas the high dose group showed between 100- and 1500 SFU/million PBMCs except one animal and with most vaccinated animals having a positive IFN-γ response. Results were shown as stacked group mean responses±standard error of the mean (FIGS. 23B and 23C). These date indicated that the MERS-Spike vaccine induced a specific T cell response that was polyfunctional as compared to animals that did not receive the vaccine (i.e., the pVax1 control group).

Example 17

Detection of Humoral Immune Response

Figure 27A:
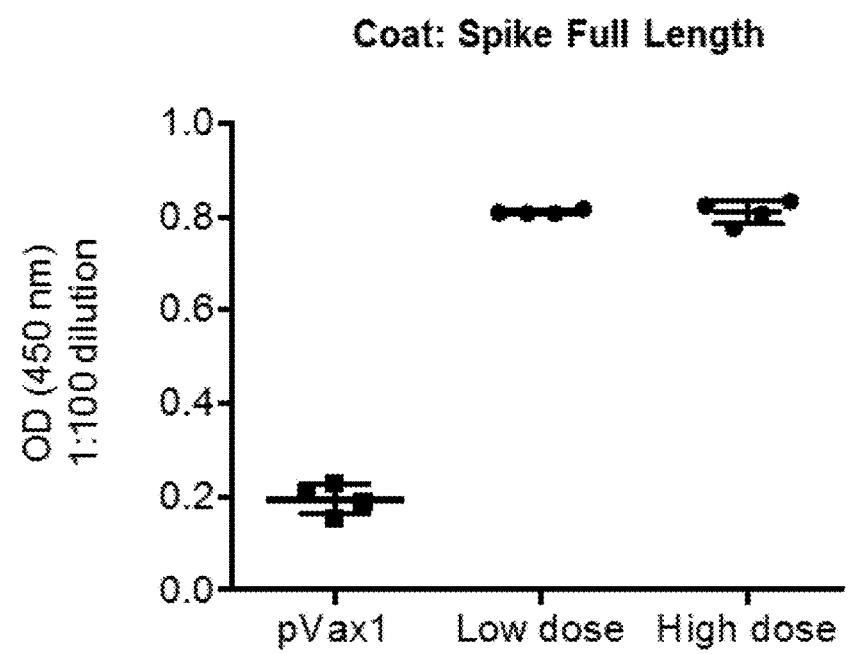
FIG. 27A through FIG. 27B, shows the antibody response after vaccination with MERS-Spike DNA vaccine in combination with electroporation. Sera from monkeys vaccinated with pVax1, pMERS-Spike (0.5 mg/animal; low dose), or pMERS-Spike (2 mg/animal; high dose) were collected two weeks after the third immunization. These sera were tested for antibodies that bound MERS-Spike protein. The results of this testing are shown in FIG. 27A and FIG. 27B.
Figure 27B:
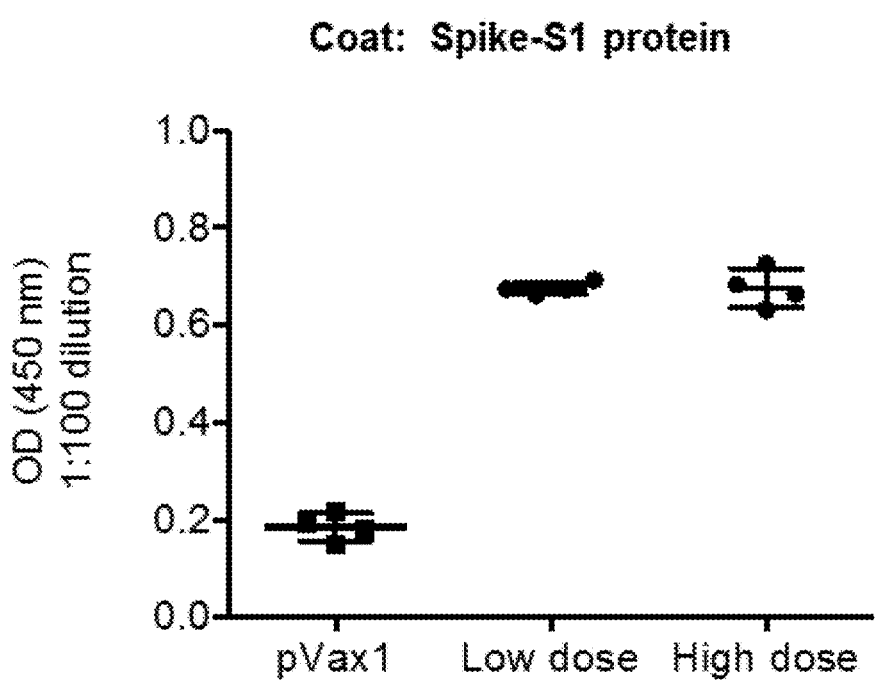

MERS-spike specific antibodies were detected in serum obtained from vaccinated animals two weeks after the third immunization. First, the MERS-Spike specific ELISA was performed utilizing full-length MERS-Spike protein. Binding ELISA results are shown in FIGS. 24A, 27A, and 27B. All pre-vaccination (day 0) sera were negative for MERS-Spike specific antibodies by ELISA. After the third vaccination with MERS-Spike, the low dose and high dose groups showed that high-titer antibodies were produced. Significant increases in endpoint MERS-spike specific antibody titers of greater than 10,000 were observed in both low and high dose vaccine immunized monkeys with MERS-Spike protein (FIG. 24B). Accordingly, animals receiving the vaccine has a MERS-Spike antigen specific humoral immune response unlike the animals that did not receive the vaccine (i.e., the pVax1 control group).

Example 18

Increased Capacity to Cross-Neutralizing Antibody Response in Non-Human Primates (NHP)

The neutralizing antibody (Nab) against a lab adapted stock of MERS-HCoV was also measured from both pre bleed and after the 3rd immunization. Monkeys were immunized three times with either 500 ug or 2 mg of total DNA by IM-EP and showed high levels of Nabs against live MERS-EMC/2012 isolates (Clade A) (FIG. 24C). MERS-CoV genomes were phylogenetically classified into 2 clades, clade A and B clusters. To test this cross clade neutralization activity, cross-neutralization was performed through the MERS-pseudovirus that expressed multiple clades of Spike protein and elicited neutralizing activity against all other MERS-CoV clades (FIG. 24D). Thus, vaccination with DNA expressing the consensus MERS-Spike led to the development of higher antibody titers and more durable Nab responses against MERS-CoV. Together, these findings demonstrated that the MERS-Spike DNA vaccination generated polyclonal antibodies that not only bound to MERS-Spike protein, but also were functionally active, and elicited MERS neutralizing antibodies.

Example 19

MERS Challenge Post-Vaccination and Pathobiology

Experiments were designed to assess clinical observations of rhesus macaques inoculated with MERS-CoV.
As shown above in Table 2, the NHPs were challenged with MERS intranasally (i.n.) at week 10, which was followed by analysis at week 12. This week 12 analysis included x-ray data/pathology analysis.
The control group, which was vaccinated with pVax1 DNA vector, had gross lesions throughout all the lung lobes and significant lesions in the lower lobe at day 5 after the challenge. This gross pathology in the control group was consistent with MERS infection. Table 3 summarizes the pathology of the animals. In summary, the MERS-Spike DNA vaccinated animals showed improved clinical parameters with absence of gross lesions as compared to the control group of animals, thereby indicating that the MERS-Spike DNA vaccine provided protection against MERS infection.

TABLE 3

Radiation image findings in lungs of rhesus macaques inoculated with MERS-CoV between 1 and 6 dpi. Images and clinical observations were made on days 1, 3, 5, and 6.

| | Day 1 | Day 3 | Day 5 | Day 6 |
| --- | --- | --- | --- | --- |
| hCoV50[1] | Interstitial infiltration present in both Caudal lobes | Diffuse interstitial infiltration present in both Caudal lobes; Bronchial pattern present in right middle lobe | Diffuse interstitial infiltration present in both Caudal lobes; Bronchial pattern present in right middle lobe | Serious diffuse interstitial infiltration present in both Caudal lobes; Bronchial pattern present in right middle lobe |
| hCoV51[1] | Interstitial infiltration | Diffuse interstitial infiltration present in | Diffuse interstitial infiltration present in | Diffuse interstitial infiltration present in |

TABLE 3-continued

Radiation image findings in lungs of rhesus macaques inoculated with MERS-CoV between 1 and 6 dpi. Images and clinical observations were made on days 1, 3, 5, and 6.

| | Day 1 | Day 3 | Day 5 | Day 6 |
|---|---|---|---|---|
| | present in both Caudal lobes | both Caudal lobes | both Caudal lobes and right middle lobe | both Caudal lobes and right middle lobe |
| hCoV52[1] | Normal | Interstitial infiltration present in both Caudal lobes; Small mass present in right Caudal lobe | Interstitial infiltration present in both Caudal lobes; Small mass in right Caudal lobe; Bronchial pattern present in both Caudal lobes | Interstitial infiltration present in both Caudal lobes; Small mass in right Caudal lobe; Bronchial pattern present in both Caudal lobes |
| hCoV53[1] | Interstitial infiltration present in both Caudal lobes; Air Bronchograms observed in right middle lobe | Interstitial infiltration present in both Caudal lobes; Air Bronchograms observed in left caudal, right caudal and middle lobes | Interstitial infiltration present in both Caudal lobes; Air Bronchograms observed in left caudal, right caudal and middle lobes | Interstitial infiltration present in both Caudal lobes; Air Bronchograms observed in left caudal, right caudal and middle lobes |
| hCoV54[2] | Normal | Normal | Normal | Normal |
| hCoV55[2] | Interstitial infiltration present in left caudal, right caudal and middle lobes | Interstitial infiltration present in left caudal, right caudal and middle lobes | Normal | Normal |
| hCoV56[2] | Normal | Normal | Normal | Normal |
| hCoV57[2] | Interstitial infiltration present in left caudal, right caudal and middle lobes | Interstitial infiltration present in left Caudal, right Caudal and middle lobes; Air Bronchograms observed in left caudal, right caudal and middle lobes | Normal | Normal |
| hCoV58[3] | Normal | Normal | Normal | Normal |
| hCoV59[3] | Normal | Normal | Normal | Normal |
| hCoV60[3] | Normal | Normal | Normal | Normal |
| hCoV61[3] | Normal | Normal | Normal | Normal |

[1]Vaccinated with pVax1.
[2]Vaccinated with MERS-Spike (high).
[3]Vaccinated with MERS-Spike (low)

6. CLAUSES

Clause 1. A vaccine comprising a nucleic acid molecule, wherein: (a) the nucleic acid molecule comprises a nucleic acid sequence having at least about 90% identity over an entire length of the nucleic acid sequence set forth in SEQ ID NO:1; or (b) the nucleic acid molecule comprises a nucleic acid sequence having at least about 90% identity over an entire length of the nucleic acid sequence set forth in SEQ ID NO:3.

Clause 2. The vaccine of clause 1, wherein the nucleic acid molecule comprises the nucleic acid sequence set forth in SEQ ID NO:1.

Clause 3. The vaccine of clause 1, wherein the nucleic acid molecule comprises the nucleic acid sequence set forth in SEQ ID NO:3.

Clause 4. The vaccine of clause 1, further comprising: (a) a peptide comprising an amino acid sequence having at least about 90% identity over an entire length of the amino acid sequence set forth in SEQ ID NO:2; or (b) a peptide comprising an amino acid sequence having at least about 90% identity over an entire length of the amino acid sequence set forth in SEQ ID NO:4.

Clause 5. The vaccine of clause 1, wherein the nucleic acid molecule comprises an expression vector.

Clause 6. The vaccine of clause 1, wherein the nucleic acid molecule is incorporated into a viral particle.

Clause 7. The vaccine of clause 1, further comprising a pharmaceutically acceptable excipient.

Clause 8. The vaccine of clause 1, further comprising an adjuvant.

Clause 9. A vaccine comprising a nucleic acid molecule, wherein: (a) the nucleic acid molecule encodes a peptide comprising an amino acid sequence having at least about 90% identity over an entire length of the amino acid sequence set forth in SEQ ID NO:2; or (b) the nucleic acid molecule encodes a peptide comprising an amino acid sequence having at least about 90% identity over an entire length of the amino acid sequence set forth in SEQ ID NO:4.

Clause 10. The vaccine of clause 9, wherein the nucleic acid molecule encodes the peptide comprising the amino acid sequence set forth in SEQ ID NO:2.

Clause 11. The vaccine of clause 9, wherein the nucleic acid molecule encodes the peptide comprising the amino acid sequence set forth in SEQ ID NO:4.

Clause 12. The vaccine of clause 9, further comprising: (a) a peptide comprising an amino acid sequence having at least about 90% identity over an entire length of the amino acid sequence set forth in SEQ ID NO:2; or (b) a peptide comprising an amino acid sequence having at least about 90% identity over an entire length of the amino acid sequence set forth in SEQ ID NO:4.

Clause 13. The vaccine of clause 9, wherein the nucleic acid molecule comprises an expression vector.

Clause 14. The vaccine of clause 9, wherein the nucleic acid molecule is incorporated into a viral particle.

Clause 15. The vaccine of clause 9, further comprising a pharmaceutically acceptable excipient.

Clause 16. The vaccine of clause 9, further comprising an adjuvant.

Clause 17. A nucleic acid molecule comprising the nucleic acid sequence set forth in SEQ ID NO:1.

Clause 18. A nucleic acid molecule comprising the nucleic acid sequence set forth in SEQ ID NO:3.

Clause 19. A peptide comprising the amino acid sequence set forth in SEQ ID NO:2.

Clause 20. A peptide comprising the amino acid sequence set forth in SEQ ID NO:4.

Clause 21. A vaccine comprising an antigen, wherein the antigen is encoded by SEQ ID NO:1 or SEQ ID NO:3.

Clause 22. The vaccine of clause 21, wherein the antigen is encoded by SEQ ID NO:1.

Clause 23. The vaccine of clause 21, wherein the antigen is encoded by SEQ ID NO:3.

Clause 24. The vaccine of clause 21, wherein the antigen comprises the amino acid sequence set forth in SEQ ID NO:2 or SEQ ID NO:4.

Clause 25. The vaccine of clause 24, wherein the antigen comprises the amino acid sequence set forth in SEQ ID NO:2.

Clause 26. The vaccine of clause 24, wherein the antigen comprises the amino acid sequence set forth in SEQ ID NO:4.

Clause 27. A vaccine comprising a peptide, wherein (a) the peptide comprises an amino acid sequence having at least about 90% identity over an entire length of the amino acid sequence set forth in SEQ ID NO:2; or (b) the peptide comprises an amino acid sequence having at least about 90% identity over an entire length of the amino acid sequence set forth in SEQ ID NO:4.

Clause 28. The vaccine of clause 27, wherein the peptide comprises the amino acid sequence set forth in SEQ ID NO:2.

Clause 29. The vaccine of clause 27, wherein the peptide comprises the amino acid sequence set forth in SEQ ID NO:4.

Clause 30. A method of inducing an immune response against a Middle East Respiratory Syndrome coronavirus (MERS-CoV) in a subject in need thereof, the method comprising administering a vaccine of clause 1, 9, 21, or 27 to the subject.

Clause 31. The method of clause 30, wherein administering includes at least one of electroporation and injection.

Clause 32. A method of protecting a subject in need thereof from infection with a Middle East Respiratory Syndrome coronavirus (MERS-CoV), the method comprising administering a vaccine of clause 1, 9, 21, or 27 to the subject.

Clause 33. The method of the clause 32, wherein administering includes at least one of electroporation and injection.

Clause 34. A method of treating a subject in need thereof against Middle East Respiratory Syndrome coronavirus (MERS-CoV), the method comprising administering a vaccine of clause 1, 9, 21, or 27 to the subject, wherein the subject is thereby resistant to one or more MERS-CoV strains.

Clause 35. The method of clause 34, wherein administering includes at least one of electroporation and injection.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An immunogenic composition comprising a nucleic acid molecule selected from the group consisting of:
   a) a nucleic acid molecule comprising a fragment of SEQ ID NO:1 encoding an immunogenic fragment of SEQ ID NO:2, wherein the fragment comprises a sequence having 100% identity to consecutive bases over at least 60% of the full length of SEQ ID NO:1; and
   b) a nucleic acid molecule comprising a fragment of SEQ ID NO:3 encoding an immunogenic fragment of SEQ ID NO:4, wherein the fragment comprises a sequence having 100% identity to consecutive bases over at least 60% of the full length of SEQ ID NO:3.

2. The immunogenic composition of claim 1, wherein the nucleic acid molecule comprises a fragment of SEQ ID NO:1 or SEQ ID NO:3, wherein the fragment comprises at least 90% of SEQ ID NO:1 or SEQ ID NO:3.

3. The immunogenic composition of claim 1, further comprising:
   (a) a peptide comprising an amino acid sequence having at least about 90% identity over an entire length of the amino acid sequence set forth in SEQ ID NO:2; or
   (b) a peptide comprising an amino acid sequence having at least about 90% identity over an entire length of the amino acid sequence set forth in SEQ ID NO:4.

4. The immunogenic composition of claim 1, wherein the nucleic acid molecule comprises an expression vector.

5. The immunogenic composition of claim 1, wherein the nucleic acid molecule is incorporated into a viral particle.

6. The immunogenic composition of claim 1, further comprising a pharmaceutically acceptable excipient.

7. The immunogenic composition of claim 1, further comprising an adjuvant.

8. A method of inducing an immune response against a Middle East Respiratory Syndrome coronavirus (MERS-CoV) in a subject in need thereof, the method comprising administering an immunogenic composition of claim 1 to the subject.

9. The method of claim 8, wherein administering includes at least one of electroporation and injection.

10. A method of protecting a subject in need thereof from infection with a Middle East Respiratory Syndrome coronavirus (MERS-CoV), the method comprising administering an immunogenic composition of claim 1 to the subject.

11. The method of the claim 10, wherein administering includes at least one of electroporation and injection.

12. A method of treating a subject in need thereof against Middle East Respiratory Syndrome coronavirus (MERS-CoV), the method comprising administering an immunogenic composition of claim 1 to the subject, wherein the subject is thereby resistant to one or more MERS-CoV strains.

13. The method of claim 12, wherein administering includes at least one of electroporation and injection.

\* \* \* \* \*

SEQUENCE LISTING

```
<160> NUMBER OF SEQ ID NOS: 7

<210> SEQ ID NO 1
<211> LENGTH: 4068
<212> TYPE: DNA
<213> ORGANISM: Artificial Sequence
<220> FEATURE:
<223> OTHER INFORMATION: MERS-CoV Consensus Spike Antigen

<400> SEQUENCE: 1
atggactgga cttggattct gttcctggtc gccgccgcaa ctcgcgtgca tagctacgtg      60
gatgtcggcc cagactctgt gaagagtgct tgcatcgagg tcgatattca gcagacattc     120
tttgacaaga cttggcctcg accaatcgac gtgagcaaag ccgacggcat catctacccc     180
cagggaagga cttatagtaa catcaccatt acataccagg gcctgttccc ttatcagggc     240
gaccacggag atatgtacgt gtattccgcc ggacatgcta ccgggaccac accacagaaa     300
ctgtttgtgg caaattattc tcaggacgtg aagcagttcg ccaacgggtt tgtggtcaga     360
atcggcgccg ctgcaaactc cactggcacc gtgatcattt cccctctac cagtgccaca     420 atccggaaaa tctaccctgc ttttatgctg ggcagctccg tgggaaactt ctctgatggg     480
aagatgggcc gcttctttaa tcacaccctg gtgctgctgc cagacggatg cgggacactg     540
ctgagggcct tctactgtat cctggagccc agaagcggaa atcactgccc tgctgggaac     600
```

```
tcatacacca gctttgccac ttatcatacc cctgctacag actgttccga tggcaattat    660
aaccggaatg cctccctgaa ctctttcaag gaatacttta atctgcgcaa ctgcacattc    720
atgtacactt ataatatcac cgaggatgaa attctggagt ggttcgggat cacacagact    780
gctcagggcg tgcacctgtt ttctagtcgc tacgtcgatc tgtatggcgg aaacatgttc    840
cagtttgcca ccctgccagt gtacgacaca attaagtact atagcatcat tccccatagt    900
atccgatcaa ttcagagcga caggaaggct tgggccgctt tctacgtgta taaactgcag    960
cccctgacct tcctgctgga ttttctgtg gacggataca tcaggagagc cattgattgc   1020
gggtttaacg acctgagcca gctgcactgt tcctatgaat ctttcgatgt ggagtccggg   1080
gtgtactctg tctcaagctt tgaggctaag ccatcaggga gcgtggtcga gcaggcagaa   1140
ggcgtggagt gcgacttcag tcccctgctg tcaggcacac ccctcaggt gtacaatttc   1200
aaaagactgg tctttactaa ctgtaattac aacctgacca agctgctgag tctgttctca   1260
gtgaacgact ttacctgcag ccagatctcc cctgcagcca ttgccagcaa ttgttattcc   1320
tctctgatcc tggattactt ctcctatccc ctgtctatga aaagtgacct gtcagtgagt   1380
tcagcaggcc ctatctctca gtttaattac aagcagtcct tctctaaccc cacttgcctg   1440
attctggcca ccgtgcctca aacctgact accatcacaa agccactgaa atactcctat   1500
attaacaagt gcagcagact gctgtccgac gatcggactg aagtgcctca gctggtcaat   1560
gccaaccagt actctccatg cgtgagcatc gtccccctca ccgtgtggga agacggagat   1620
tactatcgga agcagctgag ccccctggag ggcggcggct ggctggtggc aagtgggtca   1680
acagtcgcca tgactgagca gctgcagatg ggcttcggaa tcaccgtgca gtacggcacc   1740
gatacaaatt ctgtctgtcc taagctggaa tttgctaacg acacaaaaat tgcaagtcag   1800
ctgggcaatt gcgtggagta ctctctgtat ggagtgagtg ggagaggcgt cttccagaac   1860
tgtacagccg tgggcgtccg acagcagagg ttcgtgtacg atgcttatca gaacctggtc   1920
ggctactatt ccgacgatgg aaattactat tgcctgcgag catgcgtgag cgtcccagtg   1980
tccgtcatct acgacaagga aactaaaacc cacgcaaccc tgttcggctc agtggcctgc   2040
gagcatatta gctccaccat gagccagtat agcagatcca cacggtccat gctgaaacgg   2100
cgcgactcta catacggacc cctgcagact cctgtggggt gcgtgctggg cctggtgaac   2160
tctagtctgt tcgtcgaaga ttgcaagctg ccactgggac agtctctgtg cgcactgcca   2220
gacacaccca gtacactgac tccacgcagc gtgcgatccg tcccaggaga gatgagactg   2280
gcaagcatcg ccttcaatca ccctattcag gtggatcagc tgaactcaag ctactttaag   2340
ctgtcaatcc caacaaactt cagctttggc gtgactcagg agtatatcca gacaactatt   2400
cagaaggtga ccgtcgactg caaacagtac gtgtgcaatg gattccagaa atgcgaacag   2460
ctgctgcggg agtatgggca gttttgttcc aagatcaatc aggcactgca tggcgccaac   2520
ctgcgccagg acgatagtgt gcgaaacctg ttcgcctcag tcaagtcctc tcagagttca   2580
cctatcattc cagggttcgg cggcgacttc aacctgaccc tgctggaacc cgtgagcatc   2640
agtaccggca gcaggagcgc cagaagcgca atcgaggatc tgctgtttga caaagtgacc   2700
attgccgacc caggatacat gcaggggtat gacgattgca tgcagcaggg accagcatcc   2760
gctcgcgatc tgatctgtgc tcagtacgtg gcagggtata aggtcctgcc accctgatg    2820
gacgtgaaca tggaagctgc atatactagc tccctgctgg ggagcattgc aggagtggga   2880
tggaccgctg gactgtctag tttcgccgct atcccatttg ctcagagcat tttctacagg   2940
ctgaacggcg tgggaatcac tcagcaggtc ctgtccgaga tcagaagct gattgccaac   3000
```

```
aagttcaacc aggccctggg agctatgcag accgggttta ccacaactaa cgaagctttc    3060
cgcaaagtgc aggacgcagt caacaataac gcacaggccc tgtccaagct ggcttctgag    3120
ctgagtaata cattcggagc aatctccgcc tctattgggg atatcattca gaggctggac    3180
gtgctggagc aggatgccca gatcgaccgg ctgattaatg acgcctgac cacactgaac    3240 gcttttgtgg cacagcagct ggtccgaagt gaatcagcag ccctgtctgc ccagctggct    3300
aaggacaaag tgaacgagtg cgtcaaggct cagtcaaaac ggagcggctt ttgtgggcag    3360
ggcacccaca tcgtgagctt cgtggtcaat gcacctaacg gcctgtactt tatgcacgtg    3420
ggatactatc aagcaacca tatcgaggtg gtctccgctt atggcctgtg cgatgctgca    3480
aatcctacaa actgtattgc accagtgaac ggatacttca tcaaaactaa caacaccagg    3540
attgtggacg aatggtcata cactggctca agcttttatg cacccgagcc tatcacctcc    3600
ctgaacacaa agtacgtggc cccacatgtc acctatcaga atatctccac aaacctgcct    3660
ccacccctgc tgggcaattc taccggaatt gacttccagg atgaactgga cgagttcttt    3720
aagaatgtga gcacatccat ccccaacttt ggaagcctga ctcagattaa cactaccctg    3780
ctggatctga cctacgagat gctgagtctg cagcaggtgg tcaaggccct gaatgaatca    3840
tacatcgacc tgaaagagct ggggaattat acatactata caagtggcc ctggtacatc    3900 tggctggggt tcattgcagg actggtggct ctggcactgt cgtcttctt tatcctgtgc    3960 tgtactggat gcgggaccaa ctgtatgggc aagctgaaat gtaatcggtg ttgtgatcgc    4020
tacgaagaat acgacctgga gccccataaa gtgcatgtcc actaatga              4068

<210> SEQ ID NO 2
<211> LENGTH: 1354
<212> TYPE: PRT
<213> ORGANISM: Artificial Sequence
<220> FEATURE:
<223> OTHER INFORMATION: MERS-CoV Consensus Spike Antigen

<400> SEQUENCE: 2

Met Asp Trp Thr Trp Ile Leu Phe Leu Val Ala Ala Thr Arg Val
1               5                   10                  15

His Ser Tyr Val Asp Val Gly Pro Asp Ser Val Lys Ser Ala Cys Ile
                20                  25                  30

Glu Val Asp Ile Gln Gln Thr Phe Phe Asp Lys Thr Trp Pro Arg Pro
            35                  40                  45

Ile Asp Val Ser Lys Ala Asp Gly Ile Ile Tyr Pro Gln Gly Arg Thr
        50                  55                  60

Tyr Ser Asn Ile Thr Ile Thr Tyr Gln Gly Leu Phe Pro Tyr Gln Gly
65                  70                  75                  80

Asp His Gly Asp Met Tyr Val Tyr Ser Ala Gly His Ala Thr Gly Thr
                85                  90                  95

Thr Pro Gln Lys Leu Phe Val Ala Asn Tyr Ser Gln Asp Val Lys Gln
            100                 105                 110

Phe Ala Asn Gly Phe Val Val Arg Ile Gly Ala Ala Ala Asn Ser Thr
        115                 120                 125

Gly Thr Val Ile Ile Ser Pro Ser Thr Ser Ala Thr Ile Arg Lys Ile
    130                 135                 140

Tyr Pro Ala Phe Met Leu Gly Ser Ser Val Gly Asn Phe Ser Asp Gly
145                 150                 155                 160

Lys Met Gly Arg Phe Phe Asn His Thr Leu Val Leu Leu Pro Asp Gly
                165                 170                 175
```

```
Cys Gly Thr Leu Leu Arg Ala Phe Tyr Cys Ile Leu Glu Pro Arg Ser
            180                 185                 190

Gly Asn His Cys Pro Ala Gly Asn Ser Tyr Thr Ser Phe Ala Thr Tyr
            195                 200                 205

His Thr Pro Ala Thr Asp Cys Ser Asp Gly Asn Tyr Asn Arg Asn Ala
            210                 215                 220

Ser Leu Asn Ser Phe Lys Glu Tyr Phe Asn Leu Arg Asn Cys Thr Phe
225                 230                 235                 240

Met Tyr Thr Tyr Asn Ile Thr Glu Asp Glu Ile Leu Glu Trp Phe Gly
                245                 250                 255

Ile Thr Gln Thr Ala Gln Gly Val His Leu Phe Ser Ser Arg Tyr Val
            260                 265                 270

Asp Leu Tyr Gly Gly Asn Met Phe Gln Phe Ala Thr Leu Pro Val Tyr
            275                 280                 285

Asp Thr Ile Lys Tyr Tyr Ser Ile Ile Pro His Ser Ile Arg Ser Ile
            290                 295                 300

Gln Ser Asp Arg Lys Ala Trp Ala Ala Phe Tyr Val Tyr Lys Leu Gln
305                 310                 315                 320

Pro Leu Thr Phe Leu Leu Asp Phe Ser Val Asp Gly Tyr Ile Arg Arg
                325                 330                 335

Ala Ile Asp Cys Gly Phe Asn Asp Leu Ser Gln Leu His Cys Ser Tyr
            340                 345                 350

Glu Ser Phe Asp Val Glu Ser Gly Val Tyr Ser Val Ser Ser Phe Glu
            355                 360                 365

Ala Lys Pro Ser Gly Ser Val Val Glu Gln Ala Glu Gly Val Glu Cys
            370                 375                 380

Asp Phe Ser Pro Leu Leu Ser Gly Thr Pro Pro Gln Val Tyr Asn Phe
385                 390                 395                 400

Lys Arg Leu Val Phe Thr Asn Cys Asn Tyr Asn Leu Thr Lys Leu Leu
                405                 410                 415

Ser Leu Phe Ser Val Asn Asp Phe Thr Cys Ser Gln Ile Ser Pro Ala
            420                 425                 430

Ala Ile Ala Ser Asn Cys Tyr Ser Ser Leu Ile Leu Asp Tyr Phe Ser
            435                 440                 445

Tyr Pro Leu Ser Met Lys Ser Asp Leu Ser Val Ser Ser Ala Gly Pro
            450                 455                 460

Ile Ser Gln Phe Asn Tyr Lys Gln Ser Phe Ser Asn Pro Thr Cys Leu
465                 470                 475                 480

Ile Leu Ala Thr Val Pro His Asn Leu Thr Thr Ile Thr Lys Pro Leu
                485                 490                 495

Lys Tyr Ser Tyr Ile Asn Lys Cys Ser Arg Leu Leu Ser Asp Asp Arg
            500                 505                 510

Thr Glu Val Pro Gln Leu Val Asn Ala Asn Gln Tyr Ser Pro Cys Val
            515                 520                 525

Ser Ile Val Pro Ser Thr Val Trp Glu Asp Gly Asp Tyr Tyr Arg Lys
            530                 535                 540

Gln Leu Ser Pro Leu Glu Gly Gly Gly Trp Leu Val Ala Ser Gly Ser
545                 550                 555                 560

Thr Val Ala Met Thr Glu Gln Leu Gln Met Gly Phe Gly Ile Thr Val
                565                 570                 575

Gln Tyr Gly Thr Asp Thr Asn Ser Val Cys Pro Lys Leu Glu Phe Ala
            580                 585                 590
```

```
Asn Asp Thr Lys Ile Ala Ser Gln Leu Gly Asn Cys Val Glu Tyr Ser
            595                 600                 605

Leu Tyr Gly Val Ser Gly Arg Gly Val Phe Gln Asn Cys Thr Ala Val
610                 615                 620

Gly Val Arg Gln Gln Arg Phe Val Tyr Asp Ala Tyr Gln Asn Leu Val
625                 630                 635                 640

Gly Tyr Tyr Ser Asp Asp Gly Asn Tyr Tyr Cys Leu Arg Ala Cys Val
                645                 650                 655

Ser Val Pro Val Ser Val Ile Tyr Asp Lys Glu Thr Lys Thr His Ala
                660                 665                 670

Thr Leu Phe Gly Ser Val Ala Cys Glu His Ile Ser Ser Thr Met Ser
            675                 680                 685

Gln Tyr Ser Arg Ser Thr Arg Ser Met Leu Lys Arg Arg Asp Ser Thr
            690                 695                 700

Tyr Gly Pro Leu Gln Thr Pro Val Gly Cys Val Leu Gly Leu Val Asn
705                 710                 715                 720

Ser Ser Leu Phe Val Glu Asp Cys Lys Leu Pro Leu Gly Gln Ser Leu
                725                 730                 735

Cys Ala Leu Pro Asp Thr Pro Ser Thr Leu Thr Pro Arg Ser Val Arg
                740                 745                 750

Ser Val Pro Gly Glu Met Arg Leu Ala Ser Ile Ala Phe Asn His Pro
            755                 760                 765

Ile Gln Val Asp Gln Leu Asn Ser Ser Tyr Phe Lys Leu Ser Ile Pro
            770                 775                 780

Thr Asn Phe Ser Phe Gly Val Thr Gln Glu Tyr Ile Gln Thr Thr Ile
785                 790                 795                 800

Gln Lys Val Thr Val Asp Cys Lys Gln Tyr Val Cys Asn Gly Phe Gln
                805                 810                 815

Lys Cys Glu Gln Leu Leu Arg Glu Tyr Gly Gln Phe Cys Ser Lys Ile
                820                 825                 830

Asn Gln Ala Leu His Gly Ala Asn Leu Arg Gln Asp Asp Ser Val Arg
            835                 840                 845

Asn Leu Phe Ala Ser Val Lys Ser Ser Gln Ser Ser Pro Ile Ile Pro
850                 855                 860

Gly Phe Gly Gly Asp Phe Asn Leu Thr Leu Leu Glu Pro Val Ser Ile
865                 870                 875                 880

Ser Thr Gly Ser Arg Ser Ala Arg Ser Ala Ile Glu Asp Leu Leu Phe
                885                 890                 895

Asp Lys Val Thr Ile Ala Asp Pro Gly Tyr Met Gln Gly Tyr Asp Asp
                900                 905                 910

Cys Met Gln Gln Gly Pro Ala Ser Ala Arg Asp Leu Ile Cys Ala Gln
            915                 920                 925

Tyr Val Ala Gly Tyr Lys Val Leu Pro Pro Leu Met Asp Val Asn Met
            930                 935                 940

Glu Ala Ala Tyr Thr Ser Ser Leu Leu Gly Ser Ile Ala Gly Val Gly
945                 950                 955                 960

Trp Thr Ala Gly Leu Ser Ser Phe Ala Ala Ile Pro Phe Ala Gln Ser
                965                 970                 975

Ile Phe Tyr Arg Leu Asn Gly Val Gly Ile Thr Gln Val Leu Ser
                980                 985                 990

Glu Asn Gln Lys Leu Ile Ala Asn Lys Phe Asn Gln Ala Leu Gly Ala
            995                 1000                1005

Met Gln Thr Gly Phe Thr Thr Thr Asn Glu Ala Phe Arg Lys Val
```

| | | | | | | | | | |
|---|---|---|---|---|---|---|---|---|---|
| | | 1010 | | | 1015 | | | 1020 | |
| Gln | Asp | Ala | Val | Asn | Asn | Ala | Gln | Ala | Leu | Ser | Lys | Leu | Ala |
| | | 1025 | | | 1030 | | | 1035 | |

Gln Asp Ala Val Asn Asn Ala Gln Ala Leu Ser Lys Leu Ala
    1025                1030                1035

Ser Glu Leu Ser Asn Thr Phe Gly Ala Ile Ser Ala Ser Ile Gly
    1040                1045                1050

Asp Ile Ile Gln Arg Leu Asp Val Leu Glu Gln Asp Ala Gln Ile
    1055                1060                1065

Asp Arg Leu Ile Asn Gly Arg Leu Thr Thr Leu Asn Ala Phe Val
    1070                1075                1080

Ala Gln Gln Leu Val Arg Ser Glu Ser Ala Ala Leu Ser Ala Gln
    1085                1090                1095

Leu Ala Lys Asp Lys Val Asn Glu Cys Val Lys Ala Gln Ser Lys
    1100                1105                1110

Arg Ser Gly Phe Cys Gly Gln Gly Thr His Ile Val Ser Phe Val
    1115                1120                1125

Val Asn Ala Pro Asn Gly Leu Tyr Phe Met His Val Gly Tyr Tyr
    1130                1135                1140

Pro Ser Asn His Ile Glu Val Val Ser Ala Tyr Gly Leu Cys Asp
    1145                1150                1155

Ala Ala Asn Pro Thr Asn Cys Ile Ala Pro Val Asn Gly Tyr Phe
    1160                1165                1170

Ile Lys Thr Asn Asn Thr Arg Ile Val Asp Glu Trp Ser Tyr Thr
    1175                1180                1185

Gly Ser Ser Phe Tyr Ala Pro Glu Pro Ile Thr Ser Leu Asn Thr
    1190                1195                1200

Lys Tyr Val Ala Pro His Val Thr Tyr Gln Asn Ile Ser Thr Asn
    1205                1210                1215

Leu Pro Pro Pro Leu Leu Gly Asn Ser Thr Gly Ile Asp Phe Gln
    1220                1225                1230

Asp Glu Leu Asp Glu Phe Phe Lys Asn Val Ser Thr Ser Ile Pro
    1235                1240                1245

Asn Phe Gly Ser Leu Thr Gln Ile Asn Thr Thr Leu Leu Asp Leu
    1250                1255                1260

Thr Tyr Glu Met Leu Ser Leu Gln Gln Val Val Lys Ala Leu Asn
    1265                1270                1275

Glu Ser Tyr Ile Asp Leu Lys Glu Leu Gly Asn Tyr Thr Tyr Tyr
    1280                1285                1290

Asn Lys Trp Pro Trp Tyr Ile Trp Leu Gly Phe Ile Ala Gly Leu
    1295                1300                1305

Val Ala Leu Ala Leu Cys Val Phe Phe Ile Leu Cys Cys Thr Gly
    1310                1315                1320

Cys Gly Thr Asn Cys Met Gly Lys Leu Lys Cys Asn Arg Cys Cys
    1325                1330                1335

Asp Arg Tyr Glu Glu Tyr Asp Leu Glu Pro His Lys Val His Val
    1340                1345                1350

His

<210> SEQ ID NO 3
<211> LENGTH: 4074
<212> TYPE: DNA
<213> ORGANISM: Artificial Sequence
<220> FEATURE:
<223> OTHER INFORMATION: MERS-CoV Consensus Spike Antigen lacking
      Cytoplasmic Domain

<400> SEQUENCE: 3

```
atggactgga cttggattct gttcctggtc gccgccgcaa ctcgcgtgca tagctacgtg      60
gatgtcggcc cagactctgt gaagagtgct tgcatcgagg tcgatattca gcagacattc     120
tttgacaaga cttggcctcg accaatcgac gtgagcaaag ccgacggcat catctacccc     180
cagggaagga cttatagtaa catcaccatt acataccagg gcctgttccc ttatcagggc     240
gaccacggag atatgtacgt gtattccgcc ggacatgcta ccgggaccac accacagaaa     300
ctgtttgtgg caaattattc tcaggacgtg aagcagttcg ccaacgggtt tgtggtcaga     360
atcggcgccg ctgcaaactc cactggcacc gtgatcattt cccctctac cagtgccaca      420
atccggaaaa tctaccctgc ttttatgctg ggcagctccg tgggaaactt ctctgatggg     480
aagatgggcc gcttctttaa tcacaccctg gtgctgctgc agacggatg cgggacactg      540
ctgagggcct tctactgtat cctggagccc agaagcggaa tcactgccc tgctgggaac      600
tcatacacca gctttgccac ttatcatacc cctgctacag actgttccga tggcaattat     660
aaccggaatg cctccctgaa ctctttcaag gaatacttta tctgcgcaa ctgcacattc      720
atgtacactt ataatatcac cgaggatgaa attctggagt ggttcgggat cacacagact     780
gctcagggcg tgcacctgtt ttctagtcgc tacgtcgatc tgtatggcgg aaacatgttc     840
cagtttgcca ccctgccagt gtacgacaca attaagtact atagcatcat tccccatagt     900
atccgatcaa ttcagagcga caggaaggct tgggccgctt tctacgtgta taaactgcag     960
cccctgacct cctgctgga ttttttctgtg acggataca tcaggagagc cattgattgc    1020
gggtttaacg acctgagcca gctgcactgt tcctatgaat ctttcgatgt ggagtccggg    1080
gtgtactctg tctcaagctt tgaggctaag ccatcaggga gcgtggtcga gcaggcagaa    1140
ggcgtggagt gcgacttcag tcccctgctg tcaggcacac cccctcaggt gtacaatttc    1200
aaaagactgg tctttactaa ctgtaattac aacctgacca agctgctgag tctgttctca    1260
gtgaacgact ttacctgcag ccagatctcc cctgcagcca ttgccagcaa ttgttattcc    1320
tctctgatcc tggattactt ctcctatccc ctgtctatga aaagtgacct gtcagtgagt    1380
tcagcaggcc ctatctctca gtttaattac aagcagtcct tctctaaccc cacttgcctg    1440
attctggcca ccgtgcctca aacctgact accatcacaa agccactgaa atactcctat    1500
attaacaagt gcagcagact gctgtccgac gatcggactg aagtgcctca gctggtcaat    1560
gccaaccagt actctccatg cgtgagcatc gtccctcaa ccgtgtggga agacggagat    1620
tactatcgga agcagctgag ccccctggag ggcggcggct ggctggtggc aagtgggtca    1680
acagtcgcca tgactgagca gctgcagatg ggcttcggaa tcaccgtgca gtacggcacc    1740
gatacaaatt ctgtctgtcc taagctggaa tttgctaacg acacaaaaat tgcaagtcag    1800
ctgggcaatt gcgtggagta ctctctgtat ggagtgagtg ggagaggcgt cttccagaac    1860
tgtacagccg tgggcgtccg acagcagagg ttcgtgtacg atgcttatca gaacctggtc    1920
ggctactatt ccgacgatgg aaattactat tgcctgcgag catgcgtgag cgtcccagtg    1980
tccgtcatct acgacaagga aactaaaacc cacgcaaccc tgttcggctc agtggcctgc    2040
gagcatatta gctccaccat gagccagtat agcagatcca cacggtccat gctgaaacgg    2100
cgcgactcta catacggacc cctgcagact cctgtggggt gcgtgctggg cctggtgaac    2160
tctagtctgt tctcgaaga ttgcaagctg ccactgggac agtctctgtg cgcactgcca    2220
gacacaccca gtacactgac tccacgcagc gtgcgatccg tcccaggaga gatgagactg    2280
gcaagcatcg ccttcaatca ccctattcag gtggatcagc tgaactcaag ctactttaag    2340
```

```
ctgtcaatcc caacaaactt cagctttggc gtgactcagg agtatatcca gacaactatt    2400
cagaaggtga ccgtcgactg caaacagtac gtgtgcaatg gattccagaa atgcgaacag    2460
ctgctgcggg agtatgggca gttttgttcc aagatcaatc aggcactgca tggcgccaac    2520
ctgcgccagg acgatagtgt gcgaaacctg ttcgcctcag tcaagtcctc tcagagttca    2580
cctatcattc cagggttcgg cggcgacttc aacctgaccc tgctggaacc cgtgagcatc    2640
agtaccggca gcaggagcgc cagaagcgca atcgaggatc tgctgtttga caaagtgacc    2700
attgccgacc caggatacat gcaggggtat gacgattgca tgcagcaggg accagcatcc    2760
gctcgcgatc tgatctgtgc tcagtacgtg cagggtata aggtcctgcc accccctgatg    2820 gacgtgaaca tggaagctgc atatactagc tccctgctgg ggagcattgc aggagtggga    2880
tggaccgctg gactgtctag tttcgccgct atcccatttg ctcagagcat tttctacagg    2940
ctgaacggcg tgggaatcac tcagcaggtc ctgtccgaga atcagaagct gattgccaac    3000
aagttcaacc aggccctggg agctatgcag accgggttta ccacaactaa cgaagctttc    3060
cgcaaagtgc aggacgcagt caacaataac gcacaggccc tgtccaagct ggcttctgag    3120
ctgagtaata cattcggagc aatctccgcc tctattgggg atatcattca gaggctggac    3180
gtgctggagc aggatgccca gatcgaccgg ctgattaatg gacgcctgac cacactgaac    3240
gcttttgtgg cacagcagct ggtccgaagt gaatcagcag ccctgtctgc ccagctggct    3300
aaggacaaag tgaacgagtg cgtcaaggct cagtcaaaac ggagcggctt tgtgggcag    3360 ggcacccaca tcgtgagctt cgtggtcaat gcacctaacg gcctgtactt tatgcacgtg    3420
ggatactatc caagcaacca tatcgaggtg gtctccgctt atggcctgtg cgatgctgca    3480
aatcctacaa actgtattgc accagtgaac ggatacttca tcaaaactaa caacaccagg    3540
attgtggacg aatggtcata cactggctca agcttttatg cacccgagcc tatcacctcc    3600
ctgaacacaa agtacgtggc cccacatgtc acctatcaga atatctccac aaacctgcct    3660 ccaccccctgc tgggcaattc taccggaatt gacttccagg atgaactgga cgagttcttt    3720
aagaatgtga gcacatccat ccccaacttt ggaagcctga ctcagattaa cactaccctg    3780
ctggatctga cctacgagat gctgagtctg cagcaggtgg tcaaggccct gaatgaatca    3840
tacatcgacc tgaaagagct ggggaattat acatactata acaagtggcc ctggtacatc    3900
tggctggggt tcattgcagg actggtggct ctggcactgt gcgtcttctt tatctaatga    3960
ctgtgctgta ctggatgcgg gaccaactgt atgggcaagc tgaaatgtaa tcggtgttgt    4020
gatcgctacg aagaatacga cctggagccc cataaagtgc atgtccacta atga         4074

<210> SEQ ID NO 4
<211> LENGTH: 1318
<212> TYPE: PRT
<213> ORGANISM: Artificial Sequence
<220> FEATURE:
<223> OTHER INFORMATION: MERS-CoV Consensus Spike Antigen lacking
      Cytoplasmic Domain

<400> SEQUENCE: 4

Met Asp Trp Thr Trp Ile Leu Phe Leu Val Ala Ala Thr Arg Val
 1               5                  10                  15

His Ser Tyr Val Asp Val Gly Pro Asp Ser Val Lys Ser Ala Cys Ile
                20                  25                  30

Glu Val Asp Ile Gln Gln Thr Phe Phe Asp Lys Thr Trp Pro Arg Pro
                35                  40                  45
```

-continued

```
Ile Asp Val Ser Lys Ala Asp Gly Ile Ile Tyr Pro Gln Gly Arg Thr
 50                  55                  60

Tyr Ser Asn Ile Thr Ile Thr Tyr Gln Gly Leu Phe Pro Tyr Gln Gly
 65                  70                  75                  80

Asp His Gly Asp Met Tyr Val Tyr Ser Ala Gly His Ala Thr Gly Thr
                 85                  90                  95

Thr Pro Gln Lys Leu Phe Val Ala Asn Tyr Ser Gln Asp Val Lys Gln
            100                 105                 110

Phe Ala Asn Gly Phe Val Val Arg Ile Gly Ala Ala Ala Asn Ser Thr
            115                 120                 125

Gly Thr Val Ile Ile Ser Pro Ser Thr Ser Ala Thr Ile Arg Lys Ile
130                 135                 140

Tyr Pro Ala Phe Met Leu Gly Ser Ser Val Gly Asn Phe Ser Asp Gly
145                 150                 155                 160

Lys Met Gly Arg Phe Phe Asn His Thr Leu Val Leu Pro Asp Gly
                165                 170                 175

Cys Gly Thr Leu Leu Arg Ala Phe Tyr Cys Ile Leu Glu Pro Arg Ser
            180                 185                 190

Gly Asn His Cys Pro Ala Gly Asn Ser Tyr Thr Ser Phe Ala Thr Tyr
            195                 200                 205

His Thr Pro Ala Thr Asp Cys Ser Asp Gly Asn Tyr Asn Arg Asn Ala
210                 215                 220

Ser Leu Asn Ser Phe Lys Glu Tyr Phe Asn Leu Arg Asn Cys Thr Phe
225                 230                 235                 240

Met Tyr Thr Tyr Asn Ile Thr Glu Asp Glu Ile Leu Glu Trp Phe Gly
                245                 250                 255

Ile Thr Gln Thr Ala Gln Gly Val His Leu Phe Ser Ser Arg Tyr Val
            260                 265                 270

Asp Leu Tyr Gly Gly Asn Met Phe Gln Phe Ala Thr Leu Pro Val Tyr
            275                 280                 285

Asp Thr Ile Lys Tyr Tyr Ser Ile Ile Pro His Ser Ile Arg Ser Ile
290                 295                 300

Gln Ser Asp Arg Lys Ala Trp Ala Ala Phe Tyr Val Tyr Lys Leu Gln
305                 310                 315                 320

Pro Leu Thr Phe Leu Leu Asp Phe Ser Val Asp Gly Tyr Ile Arg Arg
                325                 330                 335

Ala Ile Asp Cys Gly Phe Asn Asp Leu Ser Gln Leu His Cys Ser Tyr
            340                 345                 350

Glu Ser Phe Asp Val Glu Ser Gly Val Tyr Ser Val Ser Ser Phe Glu
            355                 360                 365

Ala Lys Pro Ser Gly Ser Val Val Glu Gln Ala Glu Gly Val Glu Cys
370                 375                 380

Asp Phe Ser Pro Leu Leu Ser Gly Thr Pro Pro Gln Val Tyr Asn Phe
385                 390                 395                 400

Lys Arg Leu Val Phe Thr Asn Cys Asn Tyr Asn Leu Thr Lys Leu Leu
                405                 410                 415

Ser Leu Phe Ser Val Asn Asp Phe Thr Cys Ser Gln Ile Ser Pro Ala
            420                 425                 430

Ala Ile Ala Ser Asn Cys Tyr Ser Ser Leu Ile Leu Asp Tyr Phe Ser
            435                 440                 445

Tyr Pro Leu Ser Met Lys Ser Asp Leu Ser Val Ser Ser Ala Gly Pro
450                 455                 460

Ile Ser Gln Phe Asn Tyr Lys Gln Ser Phe Ser Asn Pro Thr Cys Leu
```

```
            465                 470                 475                 480
        Ile Leu Ala Thr Val Pro His Asn Leu Thr Thr Ile Thr Lys Pro Leu
                        485                 490                 495
        Lys Tyr Ser Tyr Ile Asn Lys Cys Ser Arg Leu Leu Ser Asp Asp Arg
                        500                 505                 510
        Thr Glu Val Pro Gln Leu Val Asn Ala Asn Gln Tyr Ser Pro Cys Val
                        515                 520                 525
        Ser Ile Val Pro Ser Thr Val Trp Glu Asp Gly Asp Tyr Tyr Arg Lys
                        530                 535                 540
        Gln Leu Ser Pro Leu Glu Gly Gly Trp Leu Val Ala Ser Gly Ser
        545                 550                 555                 560
        Thr Val Ala Met Thr Glu Gln Leu Gln Met Gly Phe Gly Ile Thr Val
                        565                 570                 575
        Gln Tyr Gly Thr Asp Thr Asn Ser Val Cys Pro Lys Leu Glu Phe Ala
                        580                 585                 590
        Asn Asp Thr Lys Ile Ala Ser Gln Leu Gly Asn Cys Val Glu Tyr Ser
                        595                 600                 605
        Leu Tyr Gly Val Ser Gly Arg Gly Val Phe Gln Asn Cys Thr Ala Val
            610                 615                 620
        Gly Val Arg Gln Gln Arg Phe Val Tyr Asp Ala Tyr Gln Asn Leu Val
        625                 630                 635                 640
        Gly Tyr Tyr Ser Asp Asp Gly Asn Tyr Tyr Cys Leu Arg Ala Cys Val
                        645                 650                 655
        Ser Val Pro Val Ser Val Ile Tyr Asp Lys Glu Thr Lys Thr His Ala
                        660                 665                 670
        Thr Leu Phe Gly Ser Val Ala Cys Glu His Ile Ser Ser Thr Met Ser
                        675                 680                 685
        Gln Tyr Ser Arg Ser Thr Arg Ser Met Leu Lys Arg Arg Asp Ser Thr
                        690                 695                 700
        Tyr Gly Pro Leu Gln Thr Pro Val Gly Cys Val Leu Gly Leu Val Asn
        705                 710                 715                 720
        Ser Ser Leu Phe Val Glu Asp Cys Lys Leu Pro Leu Gly Gln Ser Leu
                        725                 730                 735
        Cys Ala Leu Pro Asp Thr Pro Ser Thr Leu Thr Pro Arg Ser Val Arg
                        740                 745                 750
        Ser Val Pro Gly Glu Met Arg Leu Ala Ser Ile Ala Phe Asn His Pro
                        755                 760                 765
        Ile Gln Val Asp Gln Leu Asn Ser Ser Tyr Phe Lys Leu Ser Ile Pro
        770                 775                 780
        Thr Asn Phe Ser Phe Gly Val Thr Gln Glu Tyr Ile Gln Thr Thr Ile
        785                 790                 795                 800
        Gln Lys Val Thr Val Asp Cys Lys Gln Tyr Val Cys Asn Gly Phe Gln
                        805                 810                 815
        Lys Cys Glu Gln Leu Leu Arg Glu Tyr Gly Gln Phe Cys Ser Lys Ile
                        820                 825                 830
        Asn Gln Ala Leu His Gly Ala Asn Leu Arg Gln Asp Asp Ser Val Arg
                        835                 840                 845
        Asn Leu Phe Ala Ser Val Lys Ser Ser Gln Ser Ser Pro Ile Ile Pro
                        850                 855                 860
        Gly Phe Gly Gly Asp Phe Asn Leu Thr Leu Leu Glu Pro Val Ser Ile
        865                 870                 875                 880
        Ser Thr Gly Ser Arg Ser Ala Arg Ser Ala Ile Glu Asp Leu Leu Phe
                        885                 890                 895
```

```
Asp Lys Val Thr Ile Ala Asp Pro Gly Tyr Met Gln Gly Tyr Asp Asp
            900                 905                 910

Cys Met Gln Gln Gly Pro Ala Ser Ala Arg Asp Leu Ile Cys Ala Gln
            915                 920                 925

Tyr Val Ala Gly Tyr Lys Val Leu Pro Pro Leu Met Asp Val Asn Met
            930                 935                 940

Glu Ala Ala Tyr Thr Ser Ser Leu Leu Gly Ser Ile Ala Gly Val Gly
945                 950                 955                 960

Trp Thr Ala Gly Leu Ser Ser Phe Ala Ala Ile Pro Phe Ala Gln Ser
                965                 970                 975

Ile Phe Tyr Arg Leu Asn Gly Val Gly Ile Thr Gln Asn Val Leu Ser
            980                 985                 990

Glu Asn Gln Lys Leu Ile Ala Asn Lys Phe Asn Gln Ala Leu Gly Ala
            995                 1000                1005

Met Gln Thr Gly Phe Thr Thr Thr Asn Glu Ala Phe Arg Lys Val
       1010                1015                1020

Gln Asp Ala Val Asn Asn Asn Ala Gln Ala Leu Ser Lys Leu Ala
       1025                1030                1035

Ser Glu Leu Ser Asn Thr Phe Gly Ala Ile Ser Ala Ser Ile Gly
       1040                1045                1050

Asp Ile Ile Gln Arg Leu Asp Val Leu Glu Gln Asp Ala Gln Ile
       1055                1060                1065

Asp Arg Leu Ile Asn Gly Arg Leu Thr Thr Leu Asn Ala Phe Val
       1070                1075                1080

Ala Gln Gln Leu Val Arg Ser Glu Ser Ala Ala Leu Ser Ala Gln
       1085                1090                1095

Leu Ala Lys Asp Lys Val Asn Glu Cys Val Lys Ala Gln Ser Lys
       1100                1105                1110

Arg Ser Gly Phe Cys Gly Gln Gly Thr His Ile Val Ser Phe Val
       1115                1120                1125

Val Asn Ala Pro Asn Gly Leu Tyr Phe Met His Val Gly Tyr Tyr
       1130                1135                1140

Pro Ser Asn His Ile Glu Val Val Ser Ala Tyr Gly Leu Cys Asp
       1145                1150                1155

Ala Ala Asn Pro Thr Asn Cys Ile Ala Pro Val Asn Gly Tyr Phe
       1160                1165                1170

Ile Lys Thr Asn Asn Thr Arg Ile Val Asp Glu Trp Ser Tyr Thr
       1175                1180                1185

Gly Ser Ser Phe Tyr Ala Pro Glu Pro Ile Thr Ser Leu Asn Thr
       1190                1195                1200

Lys Tyr Val Ala Pro His Val Thr Tyr Gln Asn Ile Ser Thr Asn
       1205                1210                1215

Leu Pro Pro Pro Leu Leu Gly Asn Ser Thr Gly Ile Asp Phe Gln
       1220                1225                1230

Asp Glu Leu Asp Glu Phe Phe Lys Asn Val Ser Thr Ser Ile Pro
       1235                1240                1245

Asn Phe Gly Ser Leu Thr Gln Ile Asn Thr Thr Leu Leu Asp Leu
       1250                1255                1260

Thr Tyr Glu Met Leu Ser Leu Gln Gln Val Val Lys Ala Leu Asn
       1265                1270                1275

Glu Ser Tyr Ile Asp Leu Lys Glu Leu Gly Asn Tyr Thr Tyr Tyr
       1280                1285                1290
```

```
Asn Lys Trp Pro Trp Tyr Ile Trp Leu Gly Phe Ile Ala Gly Leu
    1295            1300            1305

Val Ala Leu Ala Leu Cys Val Phe Phe Ile
    1310            1315

<210> SEQ ID NO 5
<211> LENGTH: 54
<212> TYPE: DNA
<213> ORGANISM: Artificial Sequence
<220> FEATURE:
<223> OTHER INFORMATION: IgE leader sequence

<400> SEQUENCE: 5
atggactgga cttggattct gttcctggtc gccgccgcaa ctcgcgtgca tagc       54

<210> SEQ ID NO 6
<211> LENGTH: 18
<212> TYPE: PRT
<213> ORGANISM: Artificial Sequence
<220> FEATURE:
<223> OTHER INFORMATION: IgE leader sequence

<400> SEQUENCE: 6

Met Asp Trp Thr Trp Ile Leu Phe Leu Val Ala Ala Thr Arg Val
1               5                   10                  15

His Ser

<210> SEQ ID NO 7
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 7

Arg Lys Ala Trp Ala Ala Phe Tyr Val Tyr Lys Leu Gln Pro Leu
1               5                   10                  15
```